US012246047B2

(12) United States Patent
Fiedler et al.

(10) Patent No.: US 12,246,047 B2
(45) Date of Patent: Mar. 11, 2025

(54) ADENO-ASSOCIATED VIRUS PURIFICATION METHODS

(71) Applicant: TAKEDA PHARMACEUTICAL COMPANY LIMITED, Osaka (JP)

(72) Inventors: Christian Fiedler, Vienna (AT); Leopold Grillberger, Winchester, MA (US); Meinhard Hasslacher, Vienna (AT); Barbara Kraus, Obersdorf (AT); Dominik Mittergradnegger, Vienna (AT); Stefan Reuberger, Vienna (AT); Horst Schafhauser, Vienna (AT); Marian Bendik, Bratislava (SK)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 157 days.

(21) Appl. No.: 17/227,527

(22) Filed: Apr. 12, 2021

(65) Prior Publication Data
US 2021/0338752 A1 Nov. 4, 2021

Related U.S. Application Data

(62) Division of application No. 16/347,082, filed as application No. PCT/US2017/059967 on Nov. 3, 2017, now Pat. No. 11,000,561.

(60) Provisional application No. 62/417,775, filed on Nov. 4, 2016.

(51) Int. Cl.
*C12N 7/02* (2006.01)
*A61K 35/761* (2015.01)
*C12N 7/00* (2006.01)

(52) U.S. Cl.
CPC .............. *A61K 35/761* (2013.01); *C12N 7/00* (2013.01); *C12N 2750/14133* (2013.01); *C12N 2750/14151* (2013.01)

(58) Field of Classification Search
None
See application file for complete search history.

(56) References Cited

U.S. PATENT DOCUMENTS

| 4,158,054 A | 6/1979 | Furminger et al. |
| 4,217,418 A | 8/1980 | McAleer et al. |
| 7,399,840 B2 | 7/2008 | Burt et al. |
| 8,969,533 B2 | 3/2015 | Reiter |

(Continued)

FOREIGN PATENT DOCUMENTS

| CN | 1739801 A | 3/2006 |
| EP | 0005408 A2 | 11/1979 |

(Continued)

OTHER PUBLICATIONS

Tomlinson et al., "The Use of Density Gradient Centrifugation in a Zonal Centrifuge Rotor During the Purification of a Pear Virus," J. Gen. Virol 3: 153-156 (Year: 1968).*

(Continued)

*Primary Examiner* — M Franco G Salvoza
(74) *Attorney, Agent, or Firm* — TROUTMAN PEPPER LOCKE LLP

(57) ABSTRACT

Provided herein are methods of producing an adeno-associated virus (AAV) product, methods of purifying adeno-associated virus, and methods of purifying full AAV capsids from a concentrated AAV fraction comprising empty AAV capsids and full AAV capsids.

51 Claims, 27 Drawing Sheets

(56) References Cited

U.S. PATENT DOCUMENTS

| | | | |
|---|---|---|---|
| 9,732,327 B2 | 8/2017 | Reiter | |
| 2003/0220270 A1* | 11/2003 | Hilgers | A61P 35/00 514/23 |
| 2004/0121444 A1* | 6/2004 | Zolotukhin | C12N 7/00 435/239 |
| 2015/0374803 A1* | 12/2015 | Wolfe | C12N 15/86 424/93.2 |
| 2017/0369853 A1 | 12/2017 | Reiter | |

FOREIGN PATENT DOCUMENTS

| | | | |
|---|---|---|---|
| JP | S5415417 A | 12/1979 | |
| JP | H06247995 A | 9/1994 | |
| JP | 2003522802 A | 7/2003 | |
| JP | 2007068401 A | 3/2007 | |
| WO | WO-03039459 A2 * | 5/2003 | C07K 16/081 |
| WO | WO-03097797 A2 * | 11/2003 | C12N 15/86 |
| WO | 2004087760 A1 | 10/2004 | |
| WO | 2004113494 A2 | 12/2004 | |
| WO | 2008135229 A2 | 11/2008 | |
| WO | 2011094198 A1 | 8/2011 | |
| WO | 2016128407 A1 | 8/2016 | |
| WO | 2016128408 | 8/2016 | |

OTHER PUBLICATIONS

Brakke, Dispersion of aggregated barley stripe mosaic virus by detergents, Virology 9:506-21 D (1959).

Burrage et al. Structural differences between foot-and-mouth disease and poliomyelitis viruses D influence their inactivation by aziridines, Vaccine, 18(22):2464-61 (2000).

Cavanagh, et al. Pneumovirus-like characteristics of the mRNA and proteins of turkey D rhinotracheitis virus, Virus Res. 11 :241-56 (1988).

Clément et al., Manufacturing of recombinant adeno-associated viral vectors for clinical trials. Molecular Therapy-Methods & Clinical Development 3 (16002): published online Mar. 16, 2016.

Croyle et al., Development of a Highly Efficient Purification Process for Recombinant Adenoviral Vectors for Oral Gene Delivery, Pharmaceutical Development and Technology, 1998; 3(3): 365-372.

Darros-Barbosa et al., "Temperature and Concentration Dependence of Density of Model Liquid Foods", Internet J. Food Properties, 2003; 6(2): 195.

Dea et al., Antigenic variant of swine influenza virus causing proliferative and necrotizing D pneumonia in pigs, J. Vet. Diagn. Invest. 4:380-92 (1992).

Dorin et al., Principles of continuous flow centrifugation, Technical Information, pp. 1-15 (2004).

English Language Translation of Notice of Reasons for Rejection of Japanese Patent Application No. 2014-258342, dated Nov. 11, 2015.

English translations of Examination and Search Reports Issued in connection with Taiwanese Patent Application No. 097116163, dated Dec. 21, 2012.

Floyd et al., Aggregation of poliovirus and reovirus by dilution in water, Appl. Environ. Microbial. 33(1):159-67 (1977).

Gordon et al., Purification of maize dwarf mosaic virus by continuous-flow centrifugation, D Phytopathol. 63:1386-92 (1973).

Grandgenett et al., Large-scale purification of ribonucleic acid tumor viruses by use of continuous—D flow density gradient centrifugation, Appl. Microbial. 26(3):452-4 (1973).

Griffith, O.M., "Practical Techniques for Centrifugal Separations", Thermo Scientific. 2010.

Harrap et al., The properties of three baculoviruses from closely related hosts, Virology, 79: 14-31 D (1977).

Hutomojs et al., "Comparison of ultracentrifugation methods for concentration of recombinant alphaviruses: sucrose and iodixanol cushions", Environ. Exper. Bio. 2012; 10: 117-123.

Imahori and Yamakawa, Seikagaku Jiten [Biochemistry Dictionary], Mar. 1, 2000, Third Ed., p. 161. discussion of "Cited Reference 1" in English Language Translation of Notice of Reasons for Rejection for JP Appl. No.2014-258342, mailed Nov. 11, 2015.

International Preliminary Report on Patentability from PCT/US17/059967 dated May 7, 2019.

International Search Report from PCT/US17/059967 dated Jun. 15, 2018.

International Preliminary Report on Patentability and Written Opinion from PCT/EP08/003531 dated Nov. 10, 2009.

International Search Report from PCT/EP08/003531 dated Dec. 31, 2008. (mailed Oct. 30, 2008).

Klingmuller et al., Hepadnavirus infection requires interaction between the viral pre-S domain and D a specific hepatocellular receptor, J. Virol. 67(12): 7414-22 (1993).

Kretzschmar et al., Membrane association of influenza virus matrix protein does not require D specific hydrophobic domains or the viral Qlycoproteins, Virology, Qy, 220:37-45 (1996).

McAleer et al., High-resolution flow-zone centrifuge system, Biotechnol. Bioeng. 21(2): 317-22 D (1979).

Mistretta, et al., Purification and concentration of influenza inactivated viruses by continuous-flow zonal centrifugation, Bollettino Dell'istituto Sieroterapico Milanese, Istituto Sierterapico Milanese, DMilan, IT, 54(1):45-56 (1975).

Muys et al., Cellular transfer and AFM imaging of cancer cells using Bioimprint. J. Nanobiotechnol. vol. 4(2): 1-11 (2006).

Nettleton and Rweyemamu, "The Association of Calf Serum with the Contamination of BIIK21 Clone 13 Suspension Cells by a Parvovirus Serologically Related to the Minute Virus of Mice (MVM)" Arch. Virol. 1980; 64: 359-374.

Poiesz et al., Detection and isolation of type C retrovirus particles from fresh and cultured lymphocytes of a patient with cutaneous T-cell lymphoma. Proc. Natl. Acad. Sci. USA, 77(12): D 7415-9 (1980).

Putnak et al. Development of a purified, inactivated, Dengu-2 virus vaccine prototype in vero cells: D Immunogenicity and protection in mice and rhesus monkeys. J. Infect Dis. 174: 1176-84 (1996).

Pyke et al., Sucrose density gradient centrifugation and cross-flow filtration methods for the production of arbovirus antigens inactivated by binary ethylenimine, BMC Micrabiology, 4(3):1-8 (2004).

Reimer et al., Purification of large quantities of influenza virus by density gradient centrifugation, J. Viral. 1(6): 1207-16 (1967).

Scholz et al., Acid stability of hepatitis A virus, J. Gen. Viral. 70:2481-5 (1989).

Toplin et al., "Large-vol. Purification of Tumor Viruses by Use of Zonal Centrifuges". Applied Microbiology, May 1972. 23(5): 1010-1014, vol. 1, No. 6.

Trudel et al., Purification of infectious rubella virus by gel filtration on sepharose 2B compared to gradient centrifugation in sucrose, sodium metrizoate and metrizamide, J. Viral. Methods vol. 2. pp. 141-8 (1981).

Uyeda et al., Purification and serology of bean yellow mosaic virus, Ann. Phytopath. Soc. Japan, 41 :192-203 (1975).

Wright; Product-Related Impurities in Clinical-Grade Recombinant AAV Vectors: Characterization and Risk Assessment; Biomedicines 2: 80-97 (2014).

Zwerner et al., Harvesting the products of cell growth, Meth. Enzymol. 58: 221-9 (1979).

Office Action mailed Aug. 25, 2021 in connection with Japanese Application No. 2019-520408.

Manual of Aquatic Viral Ecology, Chapter 17, 2010, pp. 166-181.

* cited by examiner

FIGURE 16A
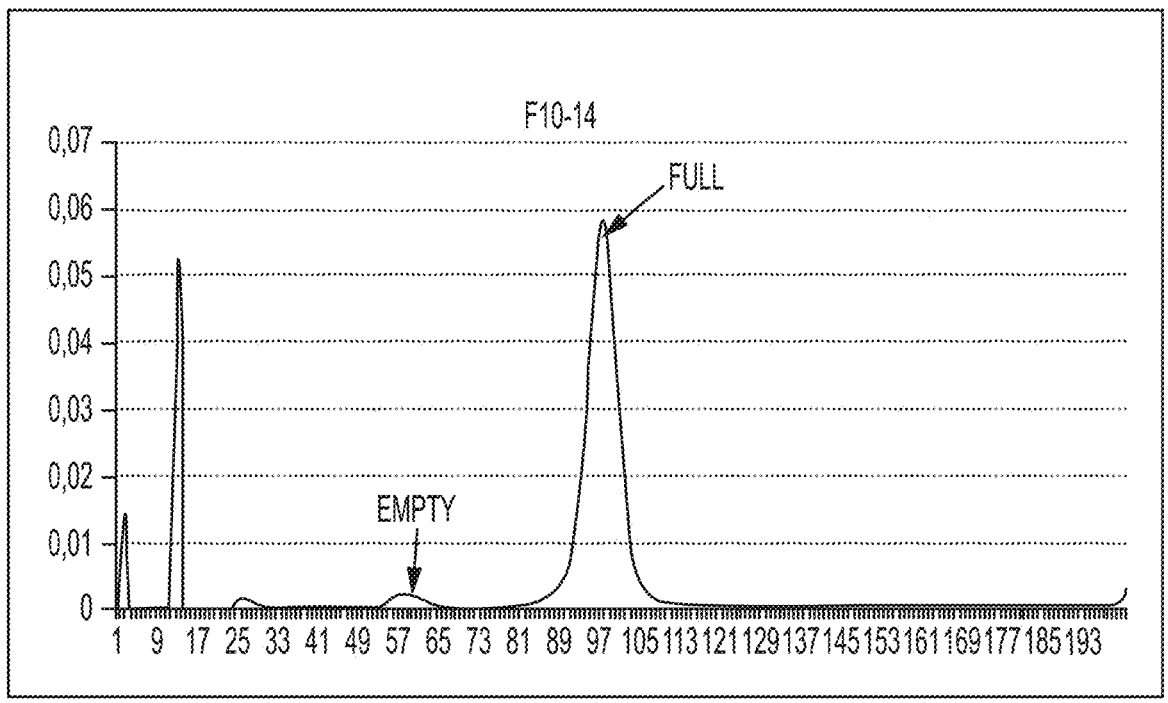
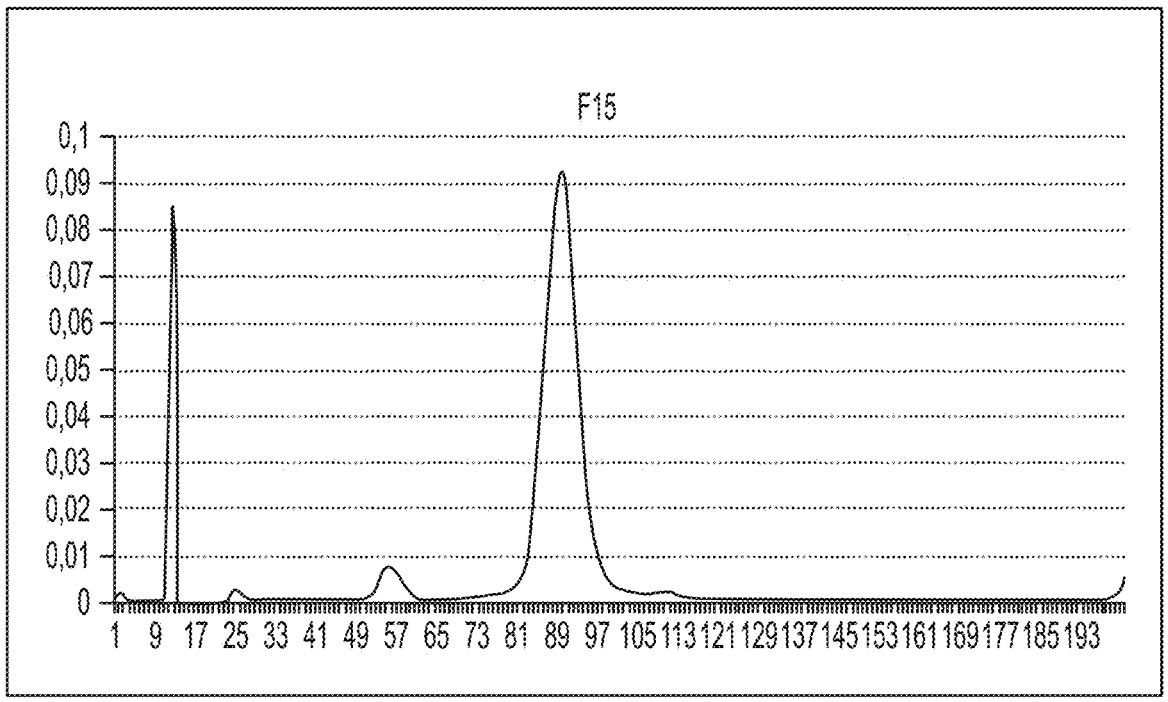

FIGURE 16A
(CONTINUED)
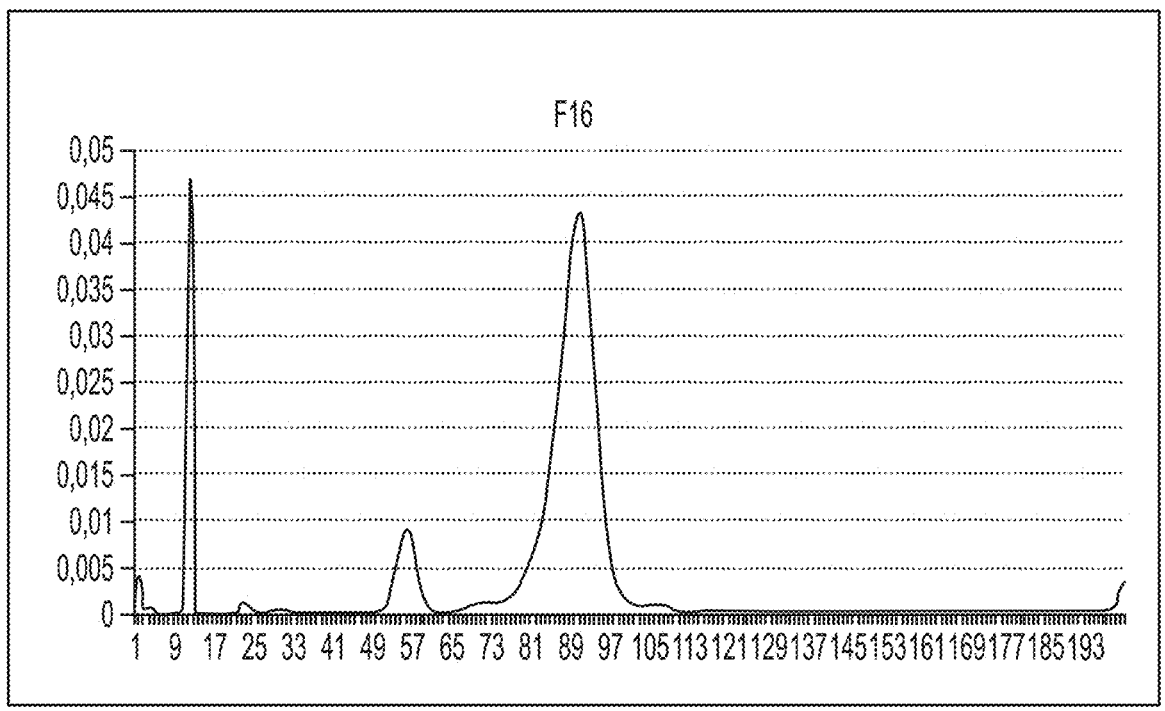
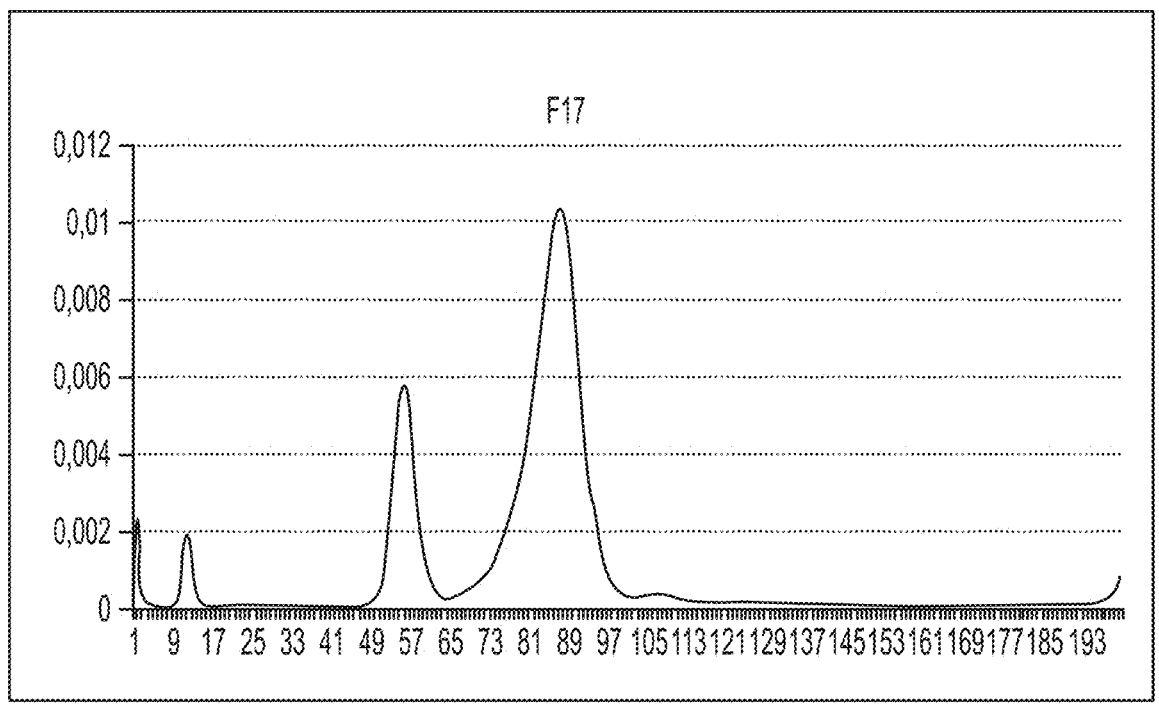

FIGURE 16A
(CONTINUED)
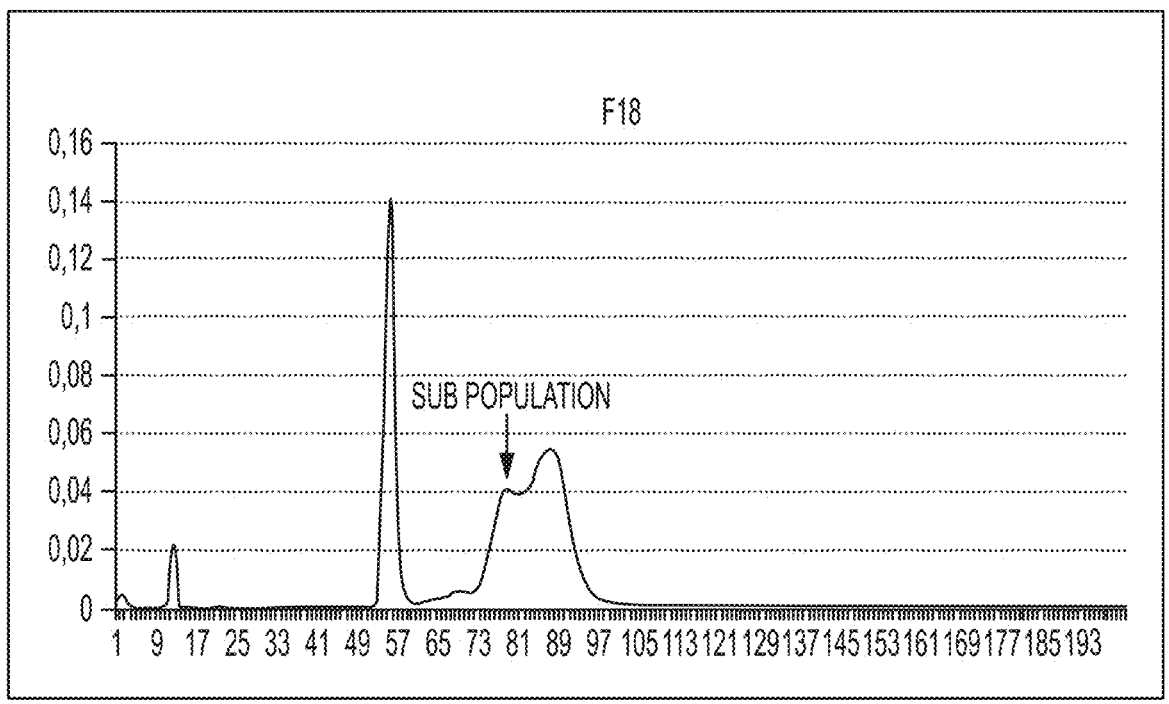
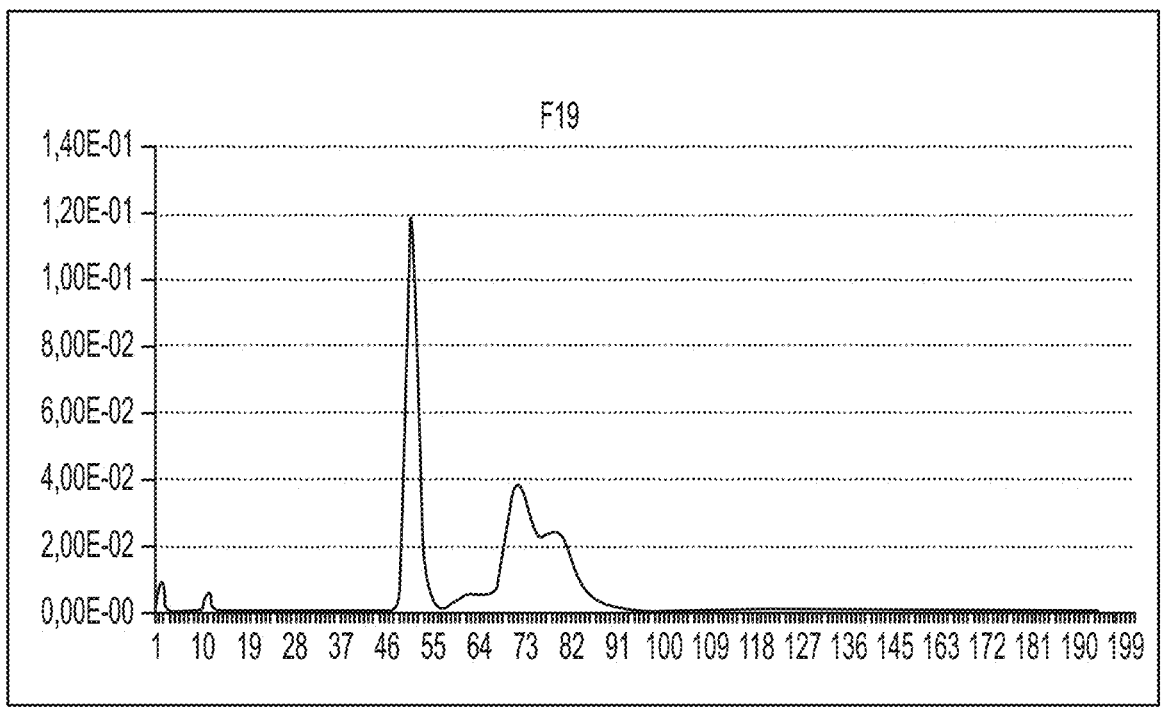

FIG. 16B
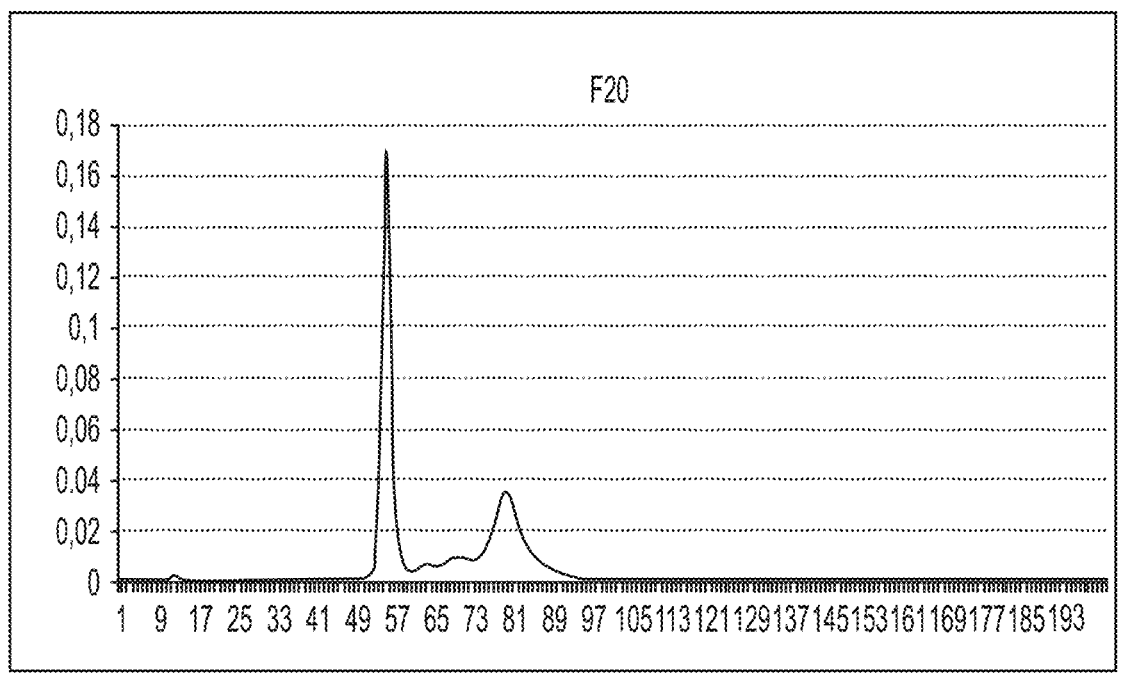
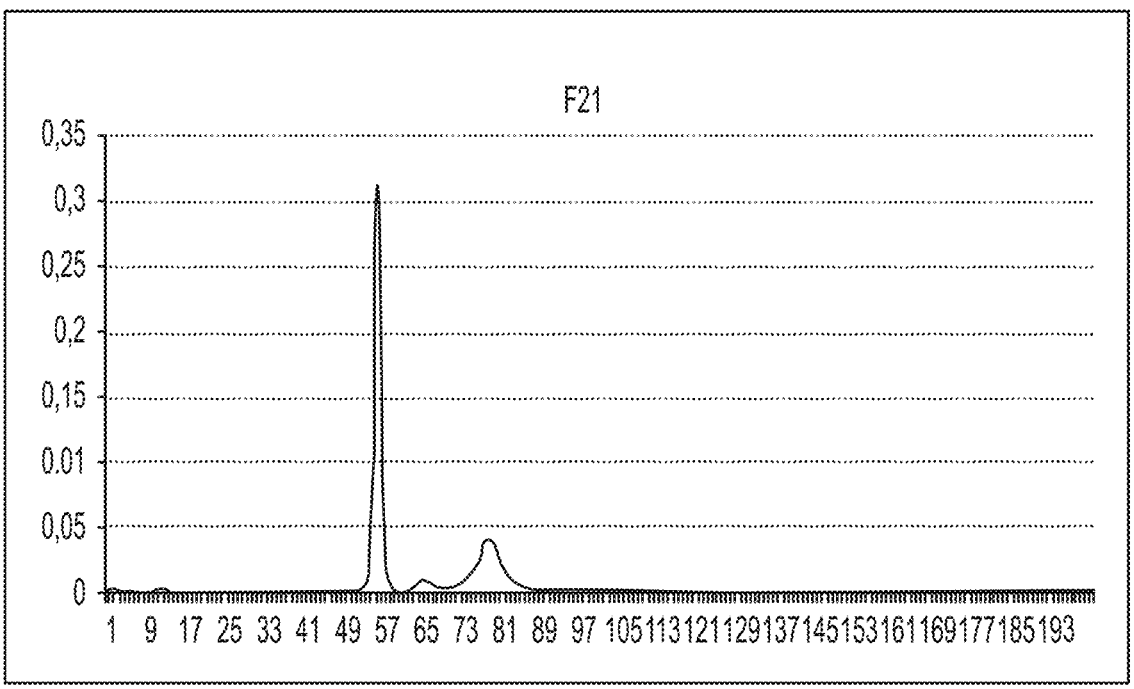

FIGURE 16B
(CONTINUED)
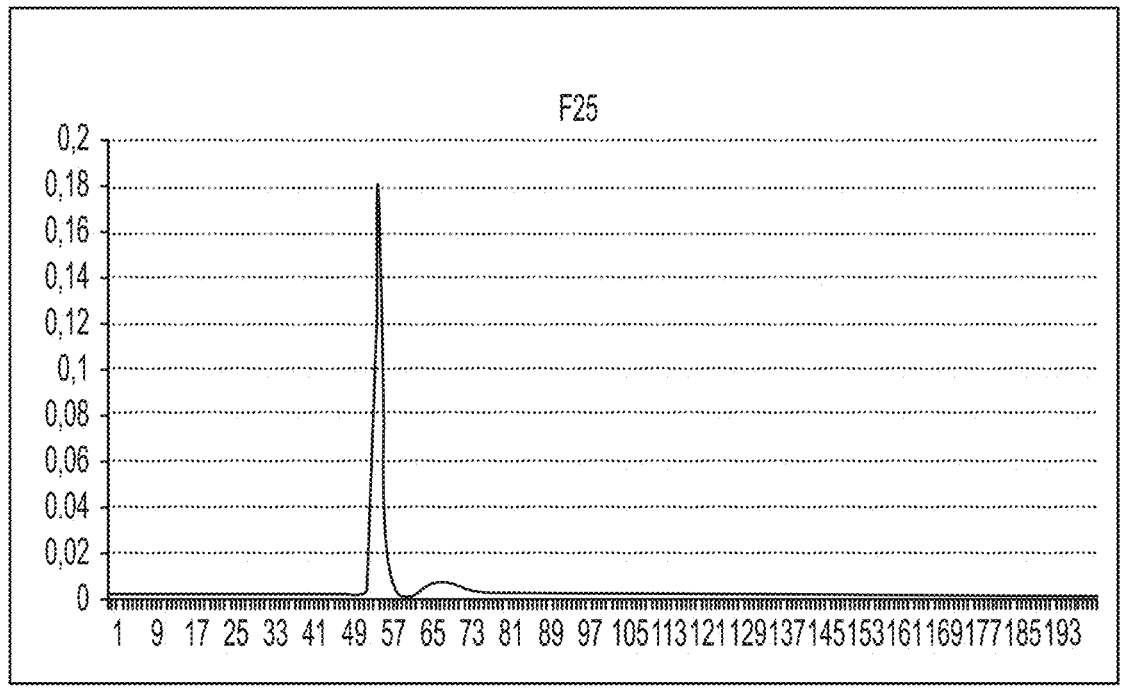
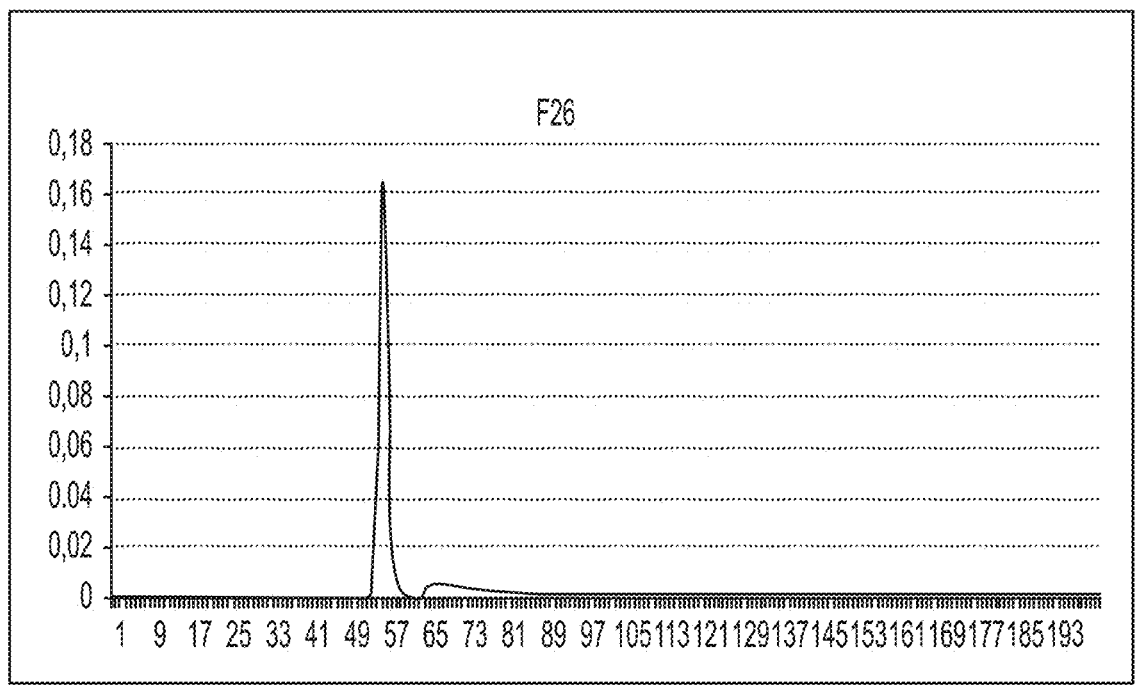

ADENO-ASSOCIATED VIRUS PURIFICATION METHODS

RELATED APPLICATIONS

This application is a divisional of U.S. patent application Ser. No. 16/347,082, filed May 2, 2019, based on PCT/US17/59967, filed Nov. 3, 2017, which claims priority to U.S. Provisional Patent Application No. 62/417,775, filed Nov. 4, 2016, which are each hereby incorporated by reference in their entirety.

TECHNICAL FIELD

The invention relates to materials and methods of purifying adeno-associated virus (AAV).

BACKGROUND

Adeno-associated virus (AAV) is a small, non-enveloped virus that packages a linear single-stranded DNA genome. AAV belongs to the family Parvoviridae and the genus Dependovirus, since productive infection by AAV occurs only in the presence of a helper virus, such as, for example, adenovirus or herpes virus. Even in the absence of a helper virus, AAV (serotype 2) can achieve latency by integrating into chromosome 19q13.4 of a host human genome. It is the only mammalian DNA virus known to be capable of site-specific integration (Daya and Berns, Clinical Microbiology Reviews, pages 583-593 (2008)).

For AAV to be safely used in the clinic, AAV has been genetically modified at several locations within its genome. For example, the Rep gene, which is required for viral replication, and the element required for site-specific integration have been eliminated from the AAV genome in many viral vectors. These recombinant AAV (rAAV), exists in an extrachromosomal state and have very low integration efficiency into the genomic DNA. The possibility of rAAV inducing random mutagenesis in a host cell is thus reduced, if not eliminated altogether. Because of these properties and the lack of pathogenicity, rAAV has shown great promise as a gene therapy vector in multiple aspects of pre-clinical and clinical applications. New serotypes and self-complementary vectors are being tested in the clinic. Alongside these ongoing vector developments, continued effort has focused on scalable manufacturing processes that can efficiently generate high titer quantities of rAAV vectors with high purity and potency.

Though the effort to design efficient, large-scale methods to purify an AAV product suitable for human administration has been great, there still remains a need for better AAV purification methods. For example, current methods of generating AAV in cell culture result in the formation of "empty" capsids which have been shown to lead to T-cell-mediated immune responses against capsid antigen, leading to low-grade hepatotoxicity and partial loss of expression (Wright, *Molec Therapy* 22(1): 1-2 (2014)). AAV purification methods which include steps for removing empty AAV capsids from the final AAV product are therefore desired.

SUMMARY

A feature of AAV vector generation in cell culture is the formation of an excess of "empty" capsids, which lack the vector genome. Such empty capsids are unable to provide a therapeutic benefit associated with transgene production. The effect of the empty capsids on clinical outcome is not clear. However, there is a potential for increasing innate or adaptive immune responses to the vector, which then renders empty capsids a concern in gene therapy contexts. Wright, Molecular Therapy 22: 1-2 (2014).

Provided herein are methods of producing an adeno-associated virus (AAV) product, methods of purifying AAV, and methods of purifying full AAV capsids from a concentrated AAV fraction comprising empty AAV capsids and full AAV capsids. The methods of the present disclosure are advantageous over those known in the art, as the methods provided here are suitable for large-scale production of AAV and provide a highly pure, potent product suitable for clinical use. In exemplary aspects, the methods described herein provide an AAV product comprising AAV particles of a homogenous population and high purity. In exemplary aspects, the methods described herein provide an AAV product comprising full-length vector DNA. In exemplary embodiments, the methods described herein provide an AAV product that is substantially free of unwanted contaminants, including but not limited to, empty AAV particles (including containing truncated or incomplete vector DNA), AAV particles with incomplete protein composition and oligomerized structures, or contaminating viruses, e.g., non AAV, lipid enveloped viruses. In exemplary embodiments, the methods described herein provide an AAV product containing a high amount of DNA (cDNA) encoding of the protein of interest.

In exemplary embodiments, the methods of the present disclosure comprise an ultracentrifugation step to separate full AAV capsids from empty AAV capsids. In exemplary aspects, the methods comprise (i) loading into a rotor a concentrated AAV fraction with at least two sugar solutions, each of which has a different sugar concentration, (ii) operating an ultracentrifuge comprising the loaded rotor in batch mode to form a sugar gradient, and (iii) obtaining a fraction of the sugar gradient to obtain an AAV fraction comprising full AAV capsids. In exemplary aspects, the rotor is a zonal rotor.

In exemplary aspects, the at least two sugar solutions each comprises a sugar at a concentration equivalent to a sucrose concentration ranging from about 45% (w/w) to about 65% (w/w) sucrose. In exemplary aspects, one sugar solution comprises a sugar at a concentration equivalent to a sucrose concentration ranging from about 52% (w/w) to about 58% (w/w) sucrose and another sugar solution comprises a sugar at a concentration equivalent to a sucrose concentration ranging from about 57% (w/w) to about 63% (w/w) sucrose. Optionally, there is another sugar solution comprising a sugar at a concentration equivalent to a sucrose concentration ranging from about 47% (w/w) to about 53% (w/w) sucrose. When loading to the bottom of the rotor or compartment, the order of loading sequence can be first the sugar solution comprising a sugar at a concentration equivalent to a sucrose concentration ranging from about 47% (w/w) to about 53% (w/w) sucrose, if present, then the sugar solution comprising a sugar at a concentration equivalent to a sucrose concentration ranging from about 52% (w/w) to about 58% (w/w) sucrose, and then the sugar solution comprising a sugar at a concentration equivalent to a sucrose concentration ranging from about 57% (w/w) to about 63% (w/w) sucrose.

In certain embodiments, the sample to be processed is added prior to the addition of the sugar solutions. In certain embodiments, ultracentrifugation is conducted in a continuous flow manner and the sample is loaded after a density gradient is achieved during centrifugation.

In certain embodiments, the methods of the present disclosure comprise an ultracentrifugation step to separate full AAV capsids from empty AAV capsids. In exemplary aspects, the methods comprise (i) loading into a rotor a concentrated AAV fraction with at least two sugar solutions, each of which has a different sugar concentration and each of which comprises a sugar at a concentration equivalent to a sucrose concentration ranging from about 45% (w/w) to about 65% (w/w) sucrose, (ii) operating an ultracentrifuge comprising the loaded rotor in batch mode to form a sugar gradient, and (iii) obtaining a fraction of the sugar gradient to obtain an AAV fraction wherein at least or about 60% of the AAV particles in the AAV fraction are full AAV capsids. In exemplary aspects, the rotor is a zonal rotor. In certain embodiments, the volume of the sugar solutions is greater than or equal to about 50% of the volume of the zonal rotor. In certain embodiments, the total volume of the sugar solutions and the AAV fraction is less than or equal to the volume of the zonal rotor. In certain embodiments, the ratio of the volume of the sugar solutions to the volume of the AAV fraction is less than or equal to one.

In certain embodiments, each sugar solution comprises a sugar at a concentration equivalent to a sucrose concentration ranging from about 50% (w/w) to about 60% (w/w) sucrose. In certain embodiments, each sugar solution comprises a sugar at a concentration equivalent to a sucrose concentration ranging from about 55% (w/w) to about 60% (w/w) sucrose. In certain embodiments, at least one of the sugar solutions comprises sugar at a concentration equivalent to a sucrose concentration greater than about 50% (w/w) sucrose. In certain embodiments, at least one of the sugar solutions comprises sugar at a concentration equivalent to a sucrose concentration greater than about 55% (w/w) sucrose. In certain embodiments, at least one of the sugar solutions comprises sugar at a concentration equivalent to a sucrose concentration ranging from about 60% (w/w) to about 65% (w/w) sucrose.

In certain embodiments, one sugar solution comprises a sugar at a concentration equivalent to a sucrose concentration ranging from about 52% (w/w) to about 58% (w/w) sucrose, wherein a second sugar solution comprises a sugar at a concentration equivalent to a sucrose concentration ranging from about 57% (w/w) to about 63% (w/w) sucrose, and optionally wherein a third sugar solution comprises a sugar at a concentration equivalent to a sucrose concentration ranging from about 47% (w/w) to about 53% (w/w) sucrose.

In certain aspects, two sugar solutions are loaded into the zonal rotor. In certain embodiments, two sugar solutions are loaded into the zonal rotor and wherein one sugar solution comprises a sugar at a concentration equivalent to a sucrose concentration ranging from about 52% (w/w) to about 58% (w/w) sucrose and a second sugar solution comprises a sugar at a concentration equivalent to a sucrose concentration ranging from about 57% (w/w) to about 63% (w/w) sucrose.

In certain aspects, at least three sugar solutions are loaded into the zonal rotor. In certain embodiments, three sugar solutions are loaded into the zonal rotor. In certain embodiments, three sugar solutions are loaded into the zonal rotor and wherein one sugar solution comprises a sugar at a concentration equivalent to a sucrose concentration ranging from about 47% (w/w) to about 53% (w/w) sucrose, a second sugar solution comprises a sugar at a concentration equivalent to a sucrose concentration ranging from about 52% (w/w) to about 58% (w/w) sucrose, and a third sugar solution comprises a sugar at a concentration equivalent to a sucrose concentration ranging from about 57% (w/w) to about 63% (w/w) sucrose.

In certain embodiments, the concentrated AAV fraction is loaded before a sugar solution comprising a sugar at a concentration equivalent to a sucrose concentration ranging from about 52% (w/w) to about 58% (w/w) sucrose, and wherein the sugar solution comprising a sugar at a concentration equivalent to a sucrose concentration ranging from about 52% (w/w) to about 58% (w/w) sucrose is loaded before a sugar solution comprising a sugar at a concentration equivalent to a sucrose concentration ranging from about 57% (w/w) to about 63% (w/w) sucrose.

In certain embodiments, the concentrated AAV fraction is loaded before a sugar solution comprising a sugar at a concentration equivalent to a sucrose concentration ranging from about 47% (w/w) to about 53% (w/w) sucrose, wherein the sugar solution comprising a sugar at a concentration equivalent to a sucrose concentration ranging from about 47% (w/w) to about 53% (w/w) sucrose is loaded before a sugar solution comprising a sugar at a concentration equivalent to a sucrose concentration ranging from about 52% (w/w) to about 58% (w/w) sucrose, and wherein the sugar solution comprising a sugar at a concentration equivalent to a sucrose concentration ranging from about 52% (w/w) to about 58% (w/w) sucrose is loaded before a sugar solution comprising a sugar at a concentration equivalent to a sucrose concentration ranging from about 57% (w/w) to about 63% (w/w) sucrose.

In certain embodiments, each sugar solution is loaded in the zonal rotor at equal volumes. In certain embodiments, the sugar solution with the smallest sugar concentration is loaded in the zonal rotor at a volume which is twice the volume of at least one of the other sugar solutions in the zonal rotor. In certain embodiments, wherein the sugar solution with the smallest sugar concentration is loaded in the zonal rotor at a volume which is at least the volume of all other sugar solutions combined in the zonal rotor. In certain embodiments, the sugar solution with the smallest sugar concentration is loaded in the zonal rotor at a volume which is at least twice the volume of the sugar solution with the largest sugar concentration, optionally, wherein the volume of the sugar solution with the largest sugar concentration is equal to the volume of the sugar solution with the intermediate sugar concentration. In certain embodiments, at least two sugar solutions are loaded into the zonal rotor, wherein the sugar solution with the smallest sugar concentration is loaded in the zonal rotor at a volume which is at least twice the volume of at least one other sugar solution in the zonal rotor. In certain embodiments, at least two sugar solutions are loaded into the zonal rotor, wherein the sugar solution with the smallest sugar concentration is loaded in the zonal rotor at a volume which is the same volume of at least one other sugar solution in the zonal rotor. In certain embodiments, the sugar solution with the smallest sugar concentration is loaded in the zonal rotor at a volume which is half the volume of the concentrated AAV fraction. In certain embodiments, where in the ratio of the volume of the total sugar gradient to the volume of the AAV fraction loaded in the zonal rotor is from about 1:1 to about 1:5.

In certain aspects, the AAV fraction comprises a buffered solution. In certain embodiments, the buffered solution includes, without limitation, phosphate buffers, histidine (e.g., L-histidine), sodium citrate, HEPES, Tris, Bicine, glycine, N-glycylglycine, sodium acetate, sodium carbonate, glycyl glycine, lysine, arginine, sodium phosphate, and mixtures thereof. In certain embodiments, the AAV fraction comprises TrisHCl and NaCl. In certain embodiments, the TrisHCl is at a concentration of about 20 to about 50 mM and the NaCl is at a concentration of about 150 mM to about 900 mM. In certain embodiments, the NaCl is at a concentration of about 500 mM to about 750 mM. In certain embodiments, the buffered solution has a pH of about 7.4 to about 9.0. In certain embodiments, the buffer comprises about 50 mM TrisHCl and about 500 mM NaCl with a pH of 8.5. In certain embodiments, the buffer comprises about 50 mM TrisHCl and about 750 mM NaCl with a pH of 8.0. In certain embodiments, the buffered solution comprises 45-55% (w/w) ethylene glycol.

In certain embodiments, each sugar solution comprises a disaccharide or trisaccharide. In certain embodiments, the disaccharide comprises sucrose, maltose, lactose, and combinations thereof. In certain embodiments, each sugar solution comprises sucrose. In certain embodiments, each of the sugar solutions further comprises TrisHCl and NaCl. In certain embodiments, the TrisHCl is at a concentration of about 20 to about 50 mM and the NaCl is at a concentration of about 150 mM to about 500 mM. In certain embodiments, the buffered solution has a pH of about 7.4 to about 8.5. In certain embodiments, the buffer comprises 20 mM TrisHCl and 8 g/L NaCl with a pH of 7.4.

In certain aspects, the methods comprise operating the ultracentrifuge at a first rotational speed of less than 10,000 rpm for less than 60 minutes, and at a second rotational speed within the range of about 30,000 to about 40,000 rpm for at least 4 hours.

In certain aspects, the methods comprise operating the ultracentrifuge at a first rotational speed of less than 10,000 rpm for less than 60 minutes, and at a second rotational speed within the range of about 30,000 to about 40,000 rpm for at least 12 hours.

In certain embodiments, the first rotational speed is about 3,000 rpm to about 6,000 rpm, optionally, about 4,000 rpm. In certain embodiments, the second rotational speed is about 35,000 rpm and optionally is maintained for about 4 to about 6 hours. In certain embodiments, the second rotational speed is maintained for at least about 16 hours or at least 20 hours. In certain embodiments, the second rotational speed is about 35,000 rpm and optionally is maintained for about 16 to about 20 hours.

In certain embodiments, the concentrated AAV fraction loaded into the zonal rotor comprises at least $1 \times 10^{12}$ AAV capsids per mL. In certain embodiments, the methods comprise harvesting a supernatant from a cell culture comprising HEK293 cells transfected with a triple plasmid system. In certain embodiments, the methods comprise (i) harvesting the supernatant about 3 to about 5 days after transfection of the HEK293 cells or (ii) when the cell culture has a cell density of greater than or about $5 \times 10^6$ cells/mL and has a cell viability of greater than 50%. In certain embodiments, the methods comprise filtering the harvested supernatant via depth filtration. In certain embodiments, the methods comprise filtering the harvested supernatant through a filter comprising cellulose and perlites and having a minimum permeability of about 500 L/m². In certain embodiments, the methods comprise filtering the harvested supernatant through a filter with a minimum pore size of about 0.2 μm. In certain embodiments, the methods comprise concentrating an AAV fraction using an ultra/diafiltration system. In certain embodiments, the methods comprise concentrating an AAV fraction using an ultra/diafiltration system before, after, or before and after a step comprising applying an AAV fraction to an anion exchange (AEX) chromatography column under conditions that allow for the AAV to flow through the AEX chromatography column. In certain embodiments, the methods comprise inactivating lipid enveloped viruses of an AAV fraction with a solvent detergent. In certain embodiments, the methods comprise nanofiltration of an AAV fraction to remove viruses greater than 35 nm. In certain embodiments, the methods comprise a polish step comprising performing AEX chromatography with a column comprising tentacle gel.

In certain embodiments, the methods comprise (i) applying an AAV fraction to an anion exchange (AEX) chromatography column under conditions that allow for the AAV to flow through the AEX chromatography column and (ii) collecting the flow-through comprising the AAV. In certain embodiments, the AAV fraction is applied to the AEX chromatography column with a loading buffer comprising about 100 mM to about 150 mM NaCl, optionally, wherein the pH of the loading buffer is about 8 to about 9. In certain embodiments, the loading buffer comprises about 115 mM to about 130 mM NaCl, optionally, the loading buffer comprises about 120 mM to about 125 mM NaCl.

In certain embodiments, host cell proteins are removed. In certain embodiments, host cell proteins are HSP70 and/or LDH.

In exemplary aspects, at least or about 55% of the AAV particles in the fraction obtained from the sugar gradient are full AAV capsids. In exemplary aspects, greater than or about 60% of the AAV particles in the fraction obtained from the sugar gradient are full AAV capsids. In exemplary aspects, greater than or about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the AAV particles in the fraction obtained from the sugar gradient are full AAV capsids.

In certain embodiments, the methods comprise testing an AAV fraction via an AAV-specific ELISA. In certain embodiments, the AAV specific ELISA is a sandwich ELISA specific for AAV. In certain embodiments, the methods do not include a step of measuring potency via quantitative PCR.

In certain embodiments, the AAV is AAV1, AAV2, AAV3, AAV4, AAV5, AAV6, AAV7, AAV8, AAV9, or AAV10. In certain embodiments, the AAV is AAV8.

Provided herein are also AAV products produced by the methods described above and herein.

BRIEF DESCRIPTION OF THE DRAWINGS

FIG. 16A-16B represents the Fractogel TMAE elution profiles derived from the indicated fractions of the analytical ultracentrifugation (AUC) as starting material. The full and empty capsids are identified with arrows. A subpopulation of capsids containing incomplete vector DNA (also defined herein as empty) is also identified. Data are also represented in Table 17. See FIG. 12 regarding the fractions.

DETAILED DESCRIPTION

Figure 1:
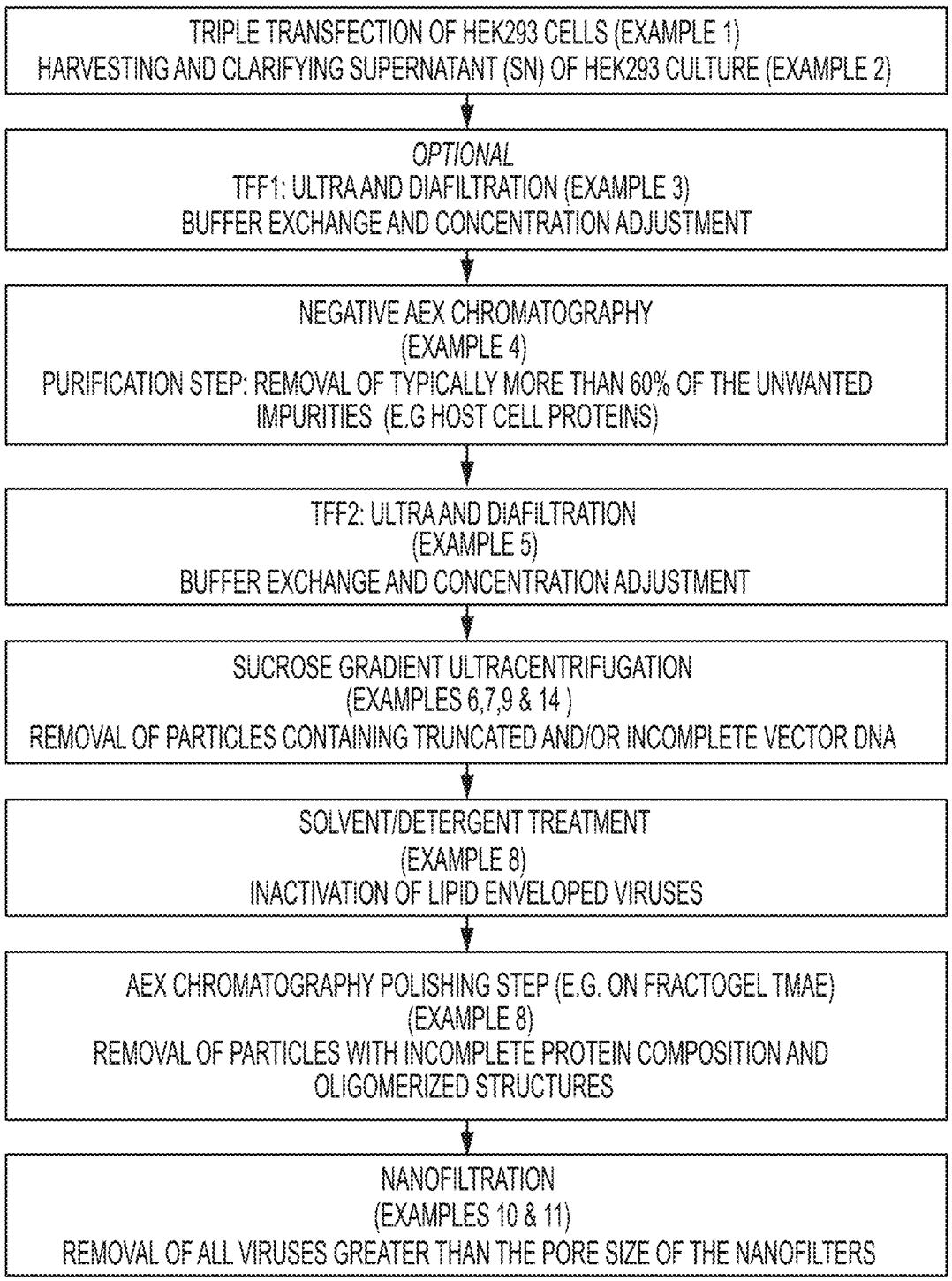
FIG. 1 is a schematic of an exemplary method of the present disclosure.

Provided herein are methods of producing an adeno-associated virus (AAV) product, methods of purifying AAV, and methods of purifying full AAV capsids from a concentrated AAV fraction comprising empty AAV capsids and full AAV capsids.

Advantageously, the methods are scalable to large volumes of starting material, e.g., cell culture. In certain embodiments, the methods provided herein are large-scale methods capable of purifying AAV from volumes of at least or about 150 L, at least or about 250 L, at least or about 500 L, at least or about 600 L, at least or about 700 L, at least or about 800 L, at least or about 900 L, or at least or about 1000 L. In certain embodiments, the methods are scalable to a minimum volume of starting material (e.g., cell culture) of at least or about 1250 L, at least or about 1500 L, at least or about 2000 L, at least or about 2500 L, at least or about 3000 L, at least or about 4000 L, at least or about 5000 L, at least or about 6000 L, at least or about 7000 L, at least or about 8000 L, at least or about 9000 L, at least or about 10,000 L, or more. For example, the methods are carried out with a minimum volume of about 1000 L or about 10,000 L or 25,000 L or more cell culture producing AAV.

The methods of producing and purifying AAV described herein are also advantageous, because the methods result in high titer AAV production. In certain embodiments, an AAV product comprising at least about $10^{10}$ virus particles (vp) is produced from about 1000 L of starting material (e.g., cell culture). In certain embodiments, an AAV product comprising at least about $10^{11}$ virus particles (vp) is produced from about 1000 L of starting material (e.g., cell culture). In certain embodiments, an AAV product comprising at least about $10^{12}$ virus particles (vp) is produced from about 1000 L of starting material (e.g., cell culture). In certain embodiments, an AAV product comprising at least about $10^{13}$ virus particles (vp) is produced from about 1000 L of starting material (e.g., cell culture). In certain embodiments, an AAV product comprising at least about $10^{14}$ virus particles (vp) is produced from about 1000 L of starting material (e.g., cell culture). In certain embodiments, an AAV product comprising at least about $10^{15}$ virus particles (vp) is produced from about 1000 L of starting material (e.g., cell culture). In certain embodiments, an AAV product comprising at least about $2 \times 10^{15}$ virus particles (vp) is produced from about 1000 L of starting material (e.g., cell culture). In certain embodiments, an AAV product comprising at least about $5 \times 10^{15}$ virus particles (vp) is produced from about 1000 L of starting material (e.g., cell culture).

The methods of the present disclosure which provide high yields of AAV, include, in certain embodiments, a nanofiltration step to remove viruses larger than the exclusion specification of the filter used in the nanofiltration step. This filtration step allows for the final AAV product to be a safer product for human administration, compared to those AAV products achieved by other methods. The nanofiltration step is an effective virus reduction step for viruses larger than the exclusion specification of the filter used in the nanofiltration step, which, in certain embodiments, means that the method has the ability to remove more than 4 logs of contaminant viruses from the AAV product via nanofiltration, as further described herein.

Another advantage of the methods described herein is that the methods yield a highly pure AAV product. In certain embodiments, the AAV product produced through the methods of the present disclosure is substantially free of one or more contaminants: host cell proteins, host cell nucleic acids (e.g., host cell DNA), plasmid DNA, empty viral vectors (including containing truncated or incomplete vector DNA), AAV particles with incomplete protein composition and oligomerized structures, or contaminating viruses, e.g., non AAV, lipid enveloped viruses, Heat shock protein 70 (HSP70), Lactate dehydrogenase (LDH), proteasomes, contaminant non-AAV viruses (e.g., lipid-enveloped viruses), host cell culture components (e.g., peptides, antibiotics), process related components (e.g. 0.3% Tri-n-butylphosphate; 1.0% Triton X100, polyethylenimine), mycoplasma, pyrogens, bacterial endotoxins, and adventitious agents. AAV products can be determined to be substantially free if they appear free of the impurity as determined by standard methods of analysis, such as, but not limited to, thin layer chromatography (TLC), gel electrophoresis and high performance liquid chromatography (HPLC), enzyme-linked immunosorbent assay (ELISA), or ITR qPCR, used by those of skill in the art to assess such purity, or sufficiently pure such that further purification would not detectably alter the physical and chemical properties, such as enzymatic and biological activities, of the substance. In one embodiment, the term "substantially free of an impurity" includes preparations of AAV having less than about 50% (by dry weight), 45%, 40%, 35%, 30%, 25%, 20%, 15%, 10%, 5%, 4%, 3%, 2%, or 1% of non-full capsid AAV material. In another embodiment, the term "substantially free of an impurity" includes preparations of AAV wherein the impurity represents less than about or at 50%, 45%, 40%, 35%, 30%, 25%, 20%, 15%, 10%, 5%, 4%, 3%, 2% or 1% of the volume of the AAV product.

In exemplary embodiments, the methods of the present disclosure provide a purified AAV product wherein at least or about 50% of the contaminant found in the starting material (e.g., cell culture) is removed. In exemplary embodiments, the methods of the present disclosure provide a purified AAV product wherein at least or about 60% of the contaminant found in the starting material (e.g., cell culture) is removed. In exemplary embodiments, the methods of the present disclosure provide a purified AAV product wherein at least or about 70% of the contaminant found in the starting material (e.g., cell culture) is removed. In exemplary embodiments, the methods of the present disclosure provide a purified AAV product wherein at least or about 80% of the contaminant found in the starting material (e.g., cell culture) is removed. In exemplary embodiments, the methods of the present disclosure provide a purified AAV product wherein at least or about 90% of the contaminant found in the starting material (e.g., cell culture) is removed.

In certain embodiments, the AAV product produced through the methods of the present disclosure is suitable for administration to a human. In certain embodiments, the AAV is a recombinant AAV (rAAV). In certain embodiments, the AAV product produced through the methods of the present disclosure is sterile and/or of good manufacturing practice (GMP) grade. In certain embodiments, the AAV product produced through the methods of the present disclosure conforms to the requirements set forth in the U.S. Pharmacopeia Chapter 1046 or the European Pharmacopoeia on gene therapy medicinal products or as mandated by the U.S. Food and Drug Administration (USFDA) or the European Medicines Agency (EMA).

Additionally, the AAV products produced from the methods described herein are highly potent. The potency of an AAV product, e.g., AAV8 product, can be described in terms of (1) in vivo biopotency (e.g., production of active protein in mice) which is given as units (FIX or FVIII) per mL of mouse plasma; or (2) in vitro biopotency. The in vitro biopotency test measures the potential of AAV vectors to transduce cells, e.g., HepG2 cells, which express and secrete the protein of interest into the medium, and determine the amount by ELISA techniques and/or enzyme activity. Suitable methods of measuring in vivo and in vitro biopotency are known in the art and are also described herein as Example 12.

In further embodiments, the AAV product produced from the methods described herein demonstrate superior DNA/AAV ratio. In exemplary embodiments, the AAV product produced from the methods described herein demonstrate a superior ratio of vector genomes per μg of AAV demonstrating that the AAV product has a high amount of full virus particles. In certain embodiments, the methods of the present disclosure comprise testing an AAV fraction via an AAV-specific ELISA. In certain embodiments, the AAV-specific ELISA is sufficient to provide a representative reading on potency of the AAV fraction, because the majority of the capsids in the AAV fraction are full capsids.

Sugar Gradient Ultracentrifugation

In exemplary embodiments, the methods of the present disclosure comprise an ultracentrifugation step during which a density gradient is formed. Though not wishing to be bound to a theory, it is believed that the ultracentrifugation step allows for full AAV capsids to be separated from empty AAV capsids. As used herein, the term "full AAV capsids" with regard to AAV or AAV capsids or AAV particles refer to those containing the complete vector genome. Full AAV capsids can provide a therapeutic benefit to recipient patients. As used herein, the term "empty" with regard to AAV or AAV capsids or AAV particles refer to those that lack the complete (i.e., full) vector genome. In certain embodiments, "empty" can also include "incomplete vector DNA" or "truncated vector DNA". Such empty AAV or empty AAV capsids or empty AAV particles may lack the vector genome in part or in whole, i.e., they may be partially empty or completely empty, and, as such, are unable to provide a therapeutic benefit.

Accordingly, the present disclosure provides a method of separating full AAV capsids from empty AAV capsids or a method of purifying full AAV capsids from a concentrated AAV fraction comprising full AAV capsids and empty AAV capsids. In exemplary aspects, the methods of the present disclosure comprise (i) loading into a rotor an AAV fraction (e.g., a solution comprising AAV) with at least two sugar solutions, each sugar solution of which has a different sugar concentration, (ii) operating an ultracentrifuge comprising the loaded rotor in batch mode to form a sugar gradient, and (iii) obtaining a fraction of the sugar gradient to obtain an AAV fraction comprising full AAV capsids. In certain embodiments, at least three, at least four, at least five, or at least six sugar solutions are loaded. In certain embodiments, two sugar solutions are loaded. In certain embodiments, three sugar solutions are loaded.

The order of loading sequence can be first the AAV fraction (e.g., a solution comprising AAV) followed by the lowest concentration of sugar solution, then followed by the next more concentrated sugar solution, and so on.

In exemplary aspects, the method comprises loading into a rotor an AAV fraction (e.g., a solution comprising AAV) with at least two sugar solutions, each sugar solution of which (a) has a different sugar concentration and (b) comprises a sugar at a concentration equivalent to a sucrose concentration ranging from about 45% (w/w) to about 65% (w/w) sucrose. In certain embodiments, the method comprises a sugar at a concentration equivalent to a sucrose concentration ranging from about 50% (w/w) to about 60% (w/w) sucrose or about 55% (w/w) to about 60% (w/w) sucrose.

In certain embodiments, at least one sugar solution comprises sugar at a concentration equivalent to a sucrose concentration between 52-58% (w/w) sucrose, at least another sugar solution comprises sugar at a concentration equivalent to a sucrose concentration between 57-63% (w/w) sucrose, and optionally, another sugar solution comprising a sugar at a concentration equivalent to a sucrose concentration between 47-53% (w/w) sucrose.

In certain embodiments, at least one sugar solution comprises sugar at a concentration equivalent to a sucrose concentration between 54-56% (w/w) sucrose, at least another sugar solution comprises sugar at a concentration equivalent to a sucrose concentration between 59-61% (w/w) sucrose, and optionally, another sugar solution comprising a sugar at a concentration equivalent to a sucrose concentration between 49-51% (w/w) sucrose.

In certain embodiments, at least one sugar solution comprises sugar at a concentration equivalent to a sucrose concentration greater than about 54% (w/w) sucrose, at least another sugar solution comprises sugar at a concentration equivalent to a sucrose concentration greater than about 59% (w/w) sucrose, and optionally, another sugar solution at a concentration equivalent to a sucrose concentration greater than about 49% (w/w) sucrose.

In certain embodiments, at least one sugar solution comprises sugar at a concentration equivalent to a sucrose concentration equal to or greater than about 55% (w/w) sucrose, at least another sugar solution comprises sugar at a concentration equivalent to a sucrose concentration equal to or greater than about 60% (w/w) sucrose, and optionally, another sugar solution at a concentration equivalent to a sucrose concentration equal to or greater than about 50% (w/w) sucrose.

In certain embodiments, at least one sugar solution comprises sugar at a concentration equivalent to a sucrose concentration of about 55% (w/w) sucrose, and at least another sugar solution comprises sugar at a concentration equivalent to a sucrose concentration of about 60% (w/w) sucrose, and optionally, another sugar solution at a concentration equivalent to a sucrose concentration of about 50% (w/w) sucrose.

The order of loading sequence can be first the AAV fraction (e.g., a solution comprising AAV) followed by the lowest concentration of sugar solution, then followed by the next more concentrated sugar solution (e.g., first the sugar solution comprising a sugar at a concentration equivalent to a sucrose concentration between 47-53% (w/w) sucrose, if present, then the sugar solution comprising a sugar at a concentration equivalent to a sucrose concentration between 52-58% (w/w) sucrose, and then the sugar solution comprising a sugar at a concentration equivalent to a sucrose concentration between 57-63% (w/w) sucrose).

An advantage of embodiments with at least one sugar solution comprising sugar at a concentration equivalent to a sucrose concentration of 52-58% (w/w) sucrose, 53-57% (w/w) sucrose or about 55% (w/w) sucrose, and at least another sugar solution comprises sugar at a concentration equivalent to a sucrose concentration of 57-63% (w/w) sucrose, 58-62% (w/w) sucrose or about 60% (w/w) sucrose, is that gradients formed of such sugar solutions can provide improved separation of AAV capsids.

In exemplary aspects, the method comprises loading into a rotor an AAV fraction (e.g., a solution comprising AAV) with at least three sugar solutions, each sugar solution of which (a) has a different sugar concentration and (b) comprises a sugar at a concentration equivalent to a sucrose concentration ranging from about 45% (w/w) to about 65% (w/w) sucrose. In certain embodiments, the method comprises a sugar at a concentration equivalent to a sucrose concentration ranging from about 50% (w/w) to about 60% (w/w) sucrose.

In certain embodiments, at least one sugar solution comprises sugar at a concentration equivalent to a sucrose concentration between 47-53% (w/w) sucrose, at least another sugar solution comprises sugar at a concentration equivalent to a sucrose concentration between 52-58% (w/w) sucrose, and at least another sugar solution comprises sugar at a concentration equivalent to a sucrose concentration between 57-63% (w/w) sucrose.

In certain embodiments, at least one sugar solution comprises sugar at a concentration equivalent to a sucrose concentration between 49-51% (w/w) sucrose, at least another sugar solution comprises sugar at a concentration equivalent to a sucrose concentration between 54-56% (w/w) sucrose, and at least another sugar solution comprises sugar at a concentration equivalent to a sucrose concentration between 59-61% (w/w) sucrose.

In certain embodiments, at least one sugar solution comprises sugar at a concentration equivalent to a sucrose concentration greater than about 49% (w/w) sucrose, at least another sugar solution comprises sugar at a concentration equivalent to a sucrose concentration greater than about 54% (w/w) sucrose, and at least one sugar solution at a concentration equivalent to a sucrose concentration greater than about 49% (w/w) sucrose.

In certain embodiments, at least one sugar solution comprises sugar at a concentration equivalent to a sucrose concentration equal to or greater than about 50% (w/w) sucrose, at least another sugar solution comprises sugar at a concentration equivalent to a sucrose concentration equal to or greater than about 55% (w/w) sucrose, and at least one sugar solution at a concentration equivalent to a sucrose concentration equal to or greater than about 60% (w/w) sucrose.

In certain embodiments, at least one sugar solution comprises sugar at a concentration equivalent to a sucrose concentration of about 50% (w/w) sucrose, at least one sugar solution comprises sugar at a concentration equivalent to a sucrose concentration of about 55% (w/w) sucrose, and at least another sugar solution comprises sugar at a concentration equivalent to a sucrose concentration or about 60% (w/w).

In certain embodiments, the order of loading sequence can be first, the sugar solution comprising comprises a sugar at a concentration equivalent to a sucrose concentration between 47-53% (w/w) sucrose, then the sugar solution comprising comprises a sugar at a concentration equivalent to a sucrose concentration between 52-58% (w/w) sucrose, and then the sugar solution comprises a sugar at a concentration equivalent to a sucrose concentration between 57-63% (w/w) sucrose.

The order of loading sequence can be first the AAV fraction (e.g., a solution comprising AAV) followed by the lowest concentration of sugar solution, then followed by the next more concentrated sugar solution (e.g., first the sugar solution comprising a sugar at a concentration equivalent to a sucrose concentration between 47-53% (w/w) sucrose, then the sugar solution comprising a sugar at a concentration equivalent to a sucrose concentration between 52-58% (w/w) sucrose, and then the sugar solution comprising a sugar at a concentration equivalent to a sucrose concentration between 57-63% (w/w) sucrose).

In exemplary aspects, each of the AAV fraction and/or sugar solutions may comprise additional components, e.g., buffering agents, salts, and the like. In certain embodiments, each of the AAV fraction and/or sugar solutions comprises, individually, any buffer substance or combinations thereof to stabilize the pH from about 5.5 to about 8.5. Examples of acceptable buffering agents are well known in the art, and include, without limitation, phosphate buffers, histidine (e.g., L-histidine), sodium citrate, HEPES, Tris, Bicine, glycine, N-glycylglycine, sodium acetate, sodium carbonate, glycyl glycine, lysine, arginine, sodium phosphate, and mixtures thereof. In certain embodiments, the buffer is TrisHCl or TrisHCl/NaCl. The pH of the buffer/fraction/solution may be 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. The pH of the buffer/fraction/solution may be from 7.0 to 9.0, from 7.1 to 8.9, from 7.2 to 9.0, from 7.0 to 8.8, from 7.2 to 8.8, from 7.1 to 8.6, from 7.3 to 8.9, from 7.4 to 9.0, or from 7.4 to 8.5. In certain embodiments, each, individually, of the buffer, AAV fraction and/or sugar solutions have a pH of about 7.4. In certain embodiments, each, individually, of the buffer, AAV fraction and/or sugar solutions have a pH of about 8.0. In certain embodiments, each, individually, of the buffer, AAV fraction and/or sugar solutions have a pH of about 8.5.

In certain embodiments, the buffer can be TrisHCl/NaCl. In certain embodiments, TrisHCl is at a concentration of about 10 mM to about 100 mM or about 20 to about 50 mM. In certain embodiments, the TrisHCl is at a concentration of about 10 mM, about 20 mM, about 25 mM, about 30 mM, about 40 mM, about 50 mM, about 60 mM, about 70 mM, about 75 mM, about 80 mM, about 90 mM, or about 100 mM. In certain embodiments, NaCl is at a concentration of about 100 mM to about 1 M, about 150 mM to about 750 mM, about 150 mM to about 500 mM, or about 500 mM to about 750 mM. In certain embodiments, the concentration of NaCl is about 100 mM, about 120 mM, about 125 mM about 130 mM, about 136 mM, about 140 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, about 525 mM, about 550 mM, about 575 mM, about 600 mM, about 625 mM, about 650 mM, about 675 mM, about 700 mM, about 725 mM, about 750 mM, about 775 mM, about 800 mM, about 825 mM, about 850 mM, about 875 mM, about 900 mM, about 925 mM, about 950 mM, about 975 mM, or about 1 M. In certain embodiments, TrisHCl is at a concentration of about 10 mM to about 100 mM or about 20 mM to about 50 mM and NaCl is at a concentration of about 100 mM to about 1M, about 150 mM to about 750 mM, about 150 mM to about 500 mM, or about 500 mM to about 750 mM. In certain embodiments, TrisHCl is at a concentration of about 50 mM and NaCl is at a concentration of about 500 mM. In certain embodiments, TrisHCl is at a concentration of about 20 mM and NaCl is at a concentration of about 136 mM. In certain embodiments, TrisHCl is at a concentration of about 50 mM and NaCl is at a concentration of about 750 mM. In certain embodiments, the buffer is a TrisHCl/NaCl buffer with a pH or about 7.4. In certain embodiments, the buffer is a TrisHCl/NaCl buffer with a pH or about 8.0. In certain embodiments, the buffer is a TrisHCl/NaCl buffer with a pH or about 8.5.

In certain embodiments, the AAV fraction solution comprises about 50 mM TrisHCl and 500 mM NaCl at a pH of 8.5. In certain embodiments, the AAV fraction solution comprises about 50 mM TrisHCl and 750 mM NaCl at a pH of 8.0. In certain embodiments, the sugar solutions comprise about 20 mM TrisHCl and 136 mM NaCl at a pH of 7.4.

In exemplary aspects, the method comprises loading into a rotor an AAV fraction (e.g., a solution comprising AAV) comprising a buffered ethylene glycol solution and at least two sugar solutions, each sugar solution of which (a) has a different sugar concentration and (b) comprises a sugar at a concentration equivalent to a sucrose concentration ranging from about 45% (w/w) to about 65% (w/w) sucrose. In certain embodiments, the method comprises a sugar at a concentration equivalent to a sucrose concentration ranging from about 50% (w/w) to about 60% (w/w) sucrose or about 55% (w/w) to about 60% (w/w) sucrose. The range of sugar concentrations are the same as listed above. An advantage of using the buffered ethylene glycol solution is that shallow gradients can be performed. Without wishing to be bound by theory, the ethylene glycol solution may change the viscosity and/or density properties of the ultracentrifugation matrix. It was surprisingly found that the addition of ethylene glycol in combination with an increased processing time creates a shallow gradient, which allows the separation of the full capsids from empty capsids containing smaller vector DNA (e.g., 3 kb or 5 kb) from the empty capsids. As used herein, a "shallow gradient" is one in which the solution density or the gradient-forming-solute concentration changes (e.g., sucrose gradient) gradually versus distance. This is opposed to one in which the solution density or the gradient-forming-solute concentration changes rapidly versus distance. For example, AAV with a DNA vector having about 2.5 to about 5.0 kb can be resolved more efficiently when the loading buffer comprises about 45% to about 55% ethylene glycol solution. In certain embodiments, use of ethylene glycol in the AAV fraction solution allows for the separation of a DNA vector having between about 2.5 to about 3.0 kb. In certain embodiments, the method allows for a greater resolution of a DNA vector having about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0 kb. In certain embodiments, the enhanced resolution occurs with a sugar solution with at least three different sugar concentrations. In certain embodiments, the enhanced resolution occurs with a sugar solution with at least two different sugar concentrations. In certain embodiments, the enhanced resolution occurs with a sugar solution with two different sugar concentrations. In certain embodiments, the enhanced resolution occurs when using one sugar solution at a concentration equivalent to a sucrose concentration of 52-58% (w/w) sucrose, 53-57% (w/w) sucrose or about 55% (w/w) sucrose, and at least another sugar solution comprises sugar at a concentration equivalent to a sucrose concentration of 57-63% (w/w) sucrose, 58-62% (w/w) sucrose or about 60% (w/w) sucrose.

In exemplary aspects, the method comprises loading into a rotor an AAV fraction (e.g., a solution comprising AAV) with a buffered ethylene glycol solution and at least three sugar solutions, each sugar solution of which (a) has a different sugar concentration and (b) comprises a sugar at a concentration equivalent to a sucrose concentration ranging from about 45% (w/w) to about 65% (w/w) sucrose. In certain embodiments, the method comprises a sugar at a concentration equivalent to a sucrose concentration ranging from about 50% (w/w) to about 60% (w/w) sucrose. The range of sugar concentrations are the same as listed above.

The buffered ethylene glycol solution may comprise any buffer substance or combinations thereof to stabilize the pH from about 5.5 to about 8.5. Examples of acceptable buffering agents are well known in the art, and include without limitation, phosphate buffers, histidine, sodium citrate, HEPES, Tris, Bicine, glycine, N-glycylglycine, sodium acetate, sodium carbonate, glycyl glycine, lysine, arginine, sodium phosphate, and mixtures thereof. In certain embodiments, the buffer is TrisHCl or TrisHCl/NaCl. The pH of the buffer/solution may be 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. The pH of the buffer/solution may be from 7.0 to 9.0, from 7.1 to 8.9, from 7.2 to 9.0, from 7.0 to 8.8, from 7.2 to 8.8, from 7.1 to 8.6, from 7.3 to 8.9, from 7.4 to 9.0, or from 7.4 to 8.5. In certain embodiments, the buffer/solution has a pH of about 7.4. In certain embodiments, the buffer/solution has a pH of about 8.0. In certain embodiments, the buffer/solution has a pH of about 8.5.

In certain embodiments, the buffered ethylene glycol solution comprises TrisHCl/NaCl. In certain embodiments, TrisHCl is at a concentration of about 10 mM to about 100 mM or about 20 to about 50 mM. In certain embodiments, the TrisHCl is at a concentration of about 10 mM, about 20 mM, about 25 mM, about 30 mM, about 40 mM, about 50 mM, about 60 mM, about 70 mM, about 75 mM, about 80 mM, about 90 mM, or about 100 mM. In certain embodiments, NaCl is at a concentration of about 100 mM to about 1 M, about 150 mM to about 750 mM, or about 150 mM to about 500 mM. In certain embodiments, the concentration of NaCl is about 100 mM, about 120 mM, about 125 mM about 130 mM, about 136 mM, about 140 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, about 525 mM, about 550 mM, about 575 mM, about 600 mM, about 625 mM, about 650 mM, about 675 mM, about 700 mM, about 725 mM, about 750 mM, about 775 mM, about 800 mM, about 825 mM, about 850 mM, about 875 mM, about 900 mM, about 925 mM, about 950 mM, about 975 mM, or about 1 M. In certain embodiments, TrisHCl is at a concentration of about 10 mM to about 100 mM or about 20 mM to about 50 mM and NaCl is at a concentration of about 100 mM to about 1M, about 150 mM to about 750 mM, about 150 mM to about 500 mM, or about 500 mM to about 750 mM. In certain embodiments, TrisHCl is at a concentration of about 50 mM and NaCl is at a concentration of about 500 mM. In certain embodiments, TrisHCl is at a concentration of about 20 mM and NaCl is at a concentration of about 136 mM. In certain embodiments, TrisHCl is at a concentration of about 50 mM and NaCl is at a concentration of about 750 mM. In certain embodiments, the buffer is a TrisHCl/NaCl buffer with a pH or about 7.4. In certain embodiments, the buffer is a TrisHCl/NaCl buffer with a pH or about 8.0. In certain embodiments, the buffer is a TrisHCl/NaCl buffer with a pH or about 8.5.

The buffered ethylene glycol solution may comprise from 45% to 55% (w/w), from 46% to 54% (w/w), from 45% to 53% (w/w), from 47% to 55% (w/w), or from 48% to 52% (w/w) of the buffer (e.g., TrisHCl/NaCl). The buffered ethylene glycol solution may comprise 40% (w/w), 41% (w/w), 42% (w/w), 43% (w/w), 44% (w/w), 45% (w/w), 46% (w/w), 47% (w/w), 48% (w/w), 49% (w/w), 50% (w/w), 51% (w/w), 52% (w/w), 53% (w/w), 54% (w/w), 55% (w/w), 56% (w/w), 57% (w/w), 58% (w/w), 59% (w/w), or 60% (w/w) of the buffer (e.g., TrisHCl/NaCl). The buffered ethylene glycol solution may be aqueous.

In certain embodiments, the buffered ethylene glycol solution comprises 45-55% (w/w) ethylene glycol, 50 mM TrisHCl, and 750 mM NaCl at a pH of 8.0. In certain embodiments, the buffered ethylene glycol solution comprises 50% (w/w) ethylene glycol, 50 mM TrisHCl, and 750 mM NaCl at a pH of 8.0.

In certain embodiments, the volume of the ultracentrifuge rotor core is from about 800 ml to about 9000 ml. In certain embodiments, the volume of the ultracentrifuge rotor core is from about 800 ml to about 7700 ml. In certain embodiments, the volume of the ultracentrifuge rotor core is about 800 ml. In certain embodiments, the volume of the ultracentrifuge rotor core is about 1600 ml. In certain embodiments, the volume of the ultracentrifuge rotor core is about 3200 ml. In certain embodiments, the volume of the ultracentrifuge rotor core is about 7700 ml.

In certain embodiments, the sugar solutions are loaded with a constant flow rate. In certain embodiments, the constant flow rate is from about 0.25 L/hr to about 10 L/hr or about 1.5 L/hr to about 7 L/hr. In certain embodiments, the constant flow rate is about 0.25 L/hr, about 0.5 L/hr, about 0.75 L/hr, about 1 L/hr, about 1.25 L/hr, about 1.5 L/hr, about 1.75 L/hr, about 2 L/hr, about 2.5 L/hr, about 3 L/hr, about 3.5 L/hr, about 4 L/hr, about 4.5 L/hr, about 5 L/hr, about 5.5 L/hr, about 6 L/hr, about 6.5 L/hr, about 7 L/hr, about 7.5 L/hr, about 8 L/hr, about 8.5 L/hr, about 9 L/hr, about 9.5 L/hr, or about 10 L/hr.

In certain embodiments, the method comprises loading into a rotor about 45-55% (w/w) of an AAV fraction (with or without a buffered ethylene glycol solution) and about 45-55% (w/w) of the at least two sugar solutions. In exemplary embodiments, the method comprises loading into a rotor about 50% (w/w) of an AAV fraction (with or without a buffered ethylene glycol solution) and about 50% (w/w) of the at least two sugar solutions. In certain embodiments, the volume of the ultracentrifuge rotor core is from about 800 ml to about 3200 ml and the rotor is loaded with about 45-55% (w/w) of an AAV fraction (with or without a buffered ethylene glycol solution) and about 45-55% (w/w) of the at least two sugar solutions. In certain embodiments, the volume of the ultracentrifuge rotor core is from about 800 ml to about 3200 ml and the rotor is loaded with about 50% (w/w) of an AAV fraction (with or without a buffered ethylene glycol solution) and about 50% (w/w) of the at least two sugar solutions in total. For example, if the rotor core is 800 ml, the AAV fraction can be 400 ml and the total sugar solution portion is 400 ml.

In certain embodiments, the method comprises loading into a rotor about 65-85% (w/w) of an AAV fraction (with or without a buffered ethylene glycol solution) and 15-35% (w/w) of the at least two sugar solutions. In certain embodiments, the method comprises loading into a rotor about 70-80% (w/w) of an AAV fraction (with or without a buffered ethylene glycol solution) and about 20-30% (w/w) of the at least two sugar solutions. In exemplary embodiments, the method comprises loading into a rotor about 75% (w/w) of an AAV fraction (with or without a buffered ethylene glycol solution) and about 25% (w/w) of the at least two sugar solutions. In exemplary embodiments, the method comprises loading into a rotor about 74% (w/w) of an AAV fraction (with or without a buffered ethylene glycol solution) and about 26% (w/w) of the at least two sugar solutions. In certain embodiments, the volume of the ultracentrifuge rotor core is from about 7700 ml to about 9000 ml and the rotor is loaded with about 70-80% (w/w) of an AAV fraction (with or without a buffered ethylene glycol solution) and about 20-30% (w/w) of the at least two sugar solutions. In certain embodiments, the volume of the ultracentrifuge rotor core is from about 7700 ml to about 9000 ml and the rotor is loaded with about 75% (w/w) of an AAV fraction (with or without a buffered ethylene glycol solution) and about 25% (w/w) of the at least two sugar solutions. In certain embodiments, the volume of the ultracentrifuge rotor core is from about 7700 ml to about 9000 ml and the rotor is loaded with about 74% (w/w) of an AAV fraction (with or without a buffered ethylene glycol solution) and about 26% (w/w) of the at least two sugar solutions. For example, if the rotor core is 7700 ml, the AAV fraction can be 6100 ml and the total sugar solution portion can be 1600 ml.

In certain embodiments, the sugar solutions are added at roughly the same volumes. In certain embodiments, the method comprises loading at least two sugar solutions, and the sugar solution with the smallest sugar concentration is loaded in the rotor at a volume which is equal to the volume of the other sugar solutions in the rotor. In certain embodiments, the method comprises loading at least two sugar solutions, and the sugar solution with the smallest sugar concentration is loaded in the rotor at a volume which is twice the volume of one of the other sugar solutions in the rotor. In certain embodiments, the method comprises loading at least two sugar solutions, and the sugar solution with the smallest sugar concentration is loaded in the rotor at a volume which is about 1.6 times or about 2.6 times the volume of one of the other sugar solutions in the rotor. In certain embodiments, the method comprises loading at least two sugar solutions, and the sugar solution with the smallest sugar concentration is loaded in the rotor at a volume which is half the volume of one of the other sugar solutions in the rotor. In certain embodiments, the sugar solution with the smallest sugar concentration is loaded in the rotor at a volume which is twice the volume of the sugar solution with the largest sugar concentration, optionally, wherein the volume of the sugar solution with the largest sugar concentration is equal to the volume of the sugar solution with the intermediate sugar concentration. In certain embodiments, the sugar solution with the smallest sugar concentration is loaded in the rotor at a volume which is about 2.6 times the volume of the sugar solution with the largest sugar concentration, optionally, wherein the volume of the sugar solution with the intermediate sugar concentration is about 1.6 times the volume of the sugar solution with the largest sugar concentration. In certain embodiments, the sugar solution with the smallest sugar concentration is loaded in the rotor at a volume which is equal to the volume of the sugar solution with the largest sugar concentration, optionally, wherein the volume of the sugar solution with the largest sugar concentration is half the volume of the sugar solution with the intermediate sugar concentration. In certain embodiments, the sugar solution with the smallest sugar concentration is loaded in the rotor at a volume which is half the volume of the AAV fraction. In certain embodiments, the sugar solution with the smallest sugar concentration is loaded in the rotor at a volume which is three-quarters the volume of the AAV fraction. In certain embodiments, the ratio of the volume of the sugar solutions to the volume of the AAV fraction is less than or equal to one.

In certain embodiments, the method comprises loading two sugar solutions and the sugar solution with the smallest sugar concentration is loaded in the rotor at a volume which is equal to the volume of the largest sugar solution in the rotor. In certain embodiments, the sugar solution with the smallest sugar concentration is loaded in the rotor at a volume which is half the volume of the AAV fraction. In certain embodiments, the ratio of the volume of the sugar solutions to the volume of the AAV fraction is less than or equal to one.

In certain embodiments, the method comprises loading three sugar solutions and the sugar solution with the smallest sugar concentration is loaded in the rotor at a volume which is at least twice the volume of one of the other two sugar solutions in the rotor. In certain embodiments, the sugar solution with the smallest sugar concentration is loaded in the rotor at a volume which is twice the volume of the sugar solution with the largest sugar concentration, optionally, wherein the volume of the sugar solution with the largest sugar concentration is equal to the volume of the sugar solution with the intermediate sugar concentration. For example, the sugar solution with the smallest sugar solution can be at a volume of about 750 ml to about 900 ml or about 800 ml, the sugar solution with an intermediate sugar concentration can be at a volume of about 350 ml to about 450 ml or about 400 ml, and the sugar solution with the largest sugar concentration can be at a volume of about 350 ml to about 450 ml or about 400 ml. In certain embodiments, the sugar solution with the smallest sugar concentration is loaded in the rotor at a volume which is half the volume of the AAV fraction. In certain embodiments, the sugar solution with the smallest sugar concentration is loaded in the rotor at a volume which is three-quarters the volume of the AAV fraction. In certain embodiments, the ratio of the volume of the sugar solutions to the volume of the AAV fraction is less than or equal to one. In exemplary aspects, the rotor is a zonal rotor. In certain embodiments, the total volume of the sugar solutions and the AAV fraction is less than or equal to the volume of the zonal rotor. In certain embodiments, the volume of the total volume of the solutions in the zonal rotor is about 800 ml to 9 L. In certain embodiments, the volume of the sugar solutions is greater than or equal to about 50% of the volume of the zonal rotor. For example, the volume of the sugar solutions is greater than or equal to about 50% of the volume of a zonal rotor having a volume of less than about 3200 ml, e.g., about 3200 ml, about 1600 ml, or about 800 ml. In certain embodiments, the volume of the sugar solutions is less than or equal to about 25% of the volume of the zonal rotor, e.g., when a core of greater than 7 L, e.g., 7.7 L, is used.

In certain embodiments, the ratio of the volume of the total sugar gradient to volume of the AAV fraction loaded in the zonal rotor is from about 1:1 to about 1:5. In some embodiments, the volume of the total sugar gradient to volume of the AAV fraction loaded in the zonal rotor is about 1:1, about 1:1.25, about 1:1.5, about 1:1.75, about 1:2, about 1:2.25, about 1:2.5, about 1:2.75, about 1:3, about 1:3.25, about 1:3.5, about 1:3.75, about 1:4, about 1:4.25, about 1:4.5, about 1:4.75, or about 1:5.

In exemplary aspects, the method comprises loading into a zonal rotor the concentrated AAV fraction with at least two sugar solutions, each of which has a different sugar concentration and each of which comprises a sugar at a concentration equivalent to a sucrose concentration ranging from about 45% (w/w) to about 65% (w/w) sucrose (ranges as outlined above), wherein (A) the volume of the sugar solutions is greater than or equal to about 50% of the volume of the zonal rotor, (B) the total volume of the sugar solutions and the AAV fraction is less than or equal to the volume of the zonal rotor, (C) the ratio of the volume of the sugar solutions to the volume of the AAV fraction is less than or equal to one, or (D) a combination of (A), (B) and (C). In certain embodiments, the volume of the total volume of the solutions in the zonal rotor is about 800 ml to 9 L. In certain embodiments, the volume of the sugar solutions is greater than or equal to about 50% of the volume of the zonal rotor. For example, the volume of the sugar solutions is greater than or equal to about 50% of the volume of a zonal rotor having a volume of less than about 3200 ml, e.g., about 3200 ml, about 1600 ml, or about 800 ml. In certain embodiments, the volume of the sugar solutions is less than or equal to about 25% of the volume of the zonal rotor, e.g., when a core of greater than 7 L, e.g., 7.7 L, is used.

In exemplary aspects, each sugar solution comprises a soluble carbohydrate or a carbohydrate mixture. In certain embodiments, each sugar solution comprises a disaccharide (e.g., sucrose, maltose or lactose) and/or a trisaccharide. In certain embodiments, the density of the sugar solutions are equal to the density of sucrose solutions with a concentration ranging from about 45% (w/w) to about 65% (w/w). In certain embodiments, at least one of the sugar solutions has a density which is equal to about 60% sucrose at a given temperature. In certain embodiments, the ranges are as recited above.

For purposes herein, a sugar other than sucrose may be used provided that the sugar in the sugar solution has a concentration equivalent to a sucrose concentration within the specified range or at the specific amount (% (w/w)). The concentration of sucrose can be determined by a refractive index method, which determines the sugar content of an aqueous solution in degrees Brix ("° Bx"), wherein one degree Brix is 1 gram of sucrose in 100 grams of solution. Degrees Brix represents the strength of the solution as percentage by mass—if the solution contains dissolved solids other than pure sucrose, then the ° Bx only approximates the dissolved solid content. The concentration of sucrose also can be determined by density measurement, in the case of pure solutions. If a determination of both identity and concentration is needed, a commercially available enzymatic kit can be applied to determine concentration and discriminate sucrose from other disaccharides and carbohydrates. A sucrose assay kit, such as the one sold by Sigma-Aldrich (St. Louis, MO) as Catalog number SCA20 may be used.

In exemplary aspects, each sugar solution comprises sucrose. In exemplary aspects, the method comprises loading into a rotor (e.g., a zonal rotor) an AAV fraction (e.g., a solution comprising AAV) with at least two sucrose solutions, each sucrose solution of which (a) has a different sucrose concentration and (b) comprises sucrose at a concentration ranging from about 45% (w/w) to about 65% (w/w) sucrose. In certain embodiments, at least one solution comprises sucrose at a concentration of between 52-58% (w/w) sucrose, and at least another solution comprises sucrose at a concentration of between 57-63% (w/w) sucrose, and optionally at least another solution comprises sucrose at a concentration of between 47-53% (w/w) sucrose. In certain embodiments, at least one solution comprises sucrose at a concentration of between 54-56% (w/w) sucrose, and at least another solution comprises sucrose at a concentration of between 59-61% (w/w) sucrose, and optionally, at least another solution comprises sucrose at a concentration between 49-51% (w/w) sucrose. In certain embodiments, at least one solution comprises sucrose at a concentration greater than about 54% (w/w) sucrose, and at least another solution comprises sucrose at a concentration greater than about 59% (w/w) sucrose, and optionally, at least another solution comprises sucrose at a concentration greater than about 49% (w/w) sucrose. In certain embodiments, at least one solution comprises sucrose at a concentration equal to or greater than about 55% (w/w) sucrose, at least one solution comprises sucrose at a concentration equal to or greater than about 60% (w/w) sucrose, and optionally, at least one solution comprises sucrose at a concentration equal to or greater than about 50% (w/w) sucrose. In certain embodiments, at least one solution comprises sucrose at a concentration equal of about 55% (w/w) sucrose, at least one solution comprises sucrose at a concentration of about 60% (w/w) sucrose, and optionally, at least one solution comprises sucrose at a concentration of about 50% (w/w) sucrose. In certain embodiments, the solution comprising AAV is a buffered solution (e.g., TrisHCl/NaCl buffer). In certain embodiments, the solution comprising AAV is a buffered ethylene glycol solution as described above. In certain embodiments, the buffered ethylene glycol solution is an aqueous solution. In certain embodiments, the buffered ethylene glycol solution is an aqueous solution that comprises 45-55% (w/w) of ethylene glycol and a buffer comprising TrisHCl and NaCl. In certain embodiments, TrisHCl is at a concentration of about 20 to about 50 mM. In certain embodiments, NaCl is at a concentration of about 100 mM to about 750 mM or about 150 mM to about 500 mM. In certain embodiments, TrisHCl is at a concentration of about 20 to about 50 mM and NaCl is at a concentration of about 100 mM to about 750 mM, about 150 mM to about 500 mM, or about 500 mM to about 750 mM. In certain embodiments, the pH of the solution comprising AAV is from 7.4 to 8.5, 7.6 to 8.3, 7.8 to 8.5, 7.4 to 7.8, 7.6 to 8.0, 7.8 to 8.2, or 8.0 to 8.5.

In exemplary aspects, the method comprises loading into a rotor (e.g., a zonal rotor) an AAV fraction (e.g., a solution comprising AAV) with at least two sucrose solutions, each sucrose solution of which (a) has a different sucrose concentration and (b) comprises sucrose at a concentration ranging from about 50% (w/w) to about 60% (w/w) sucrose. In certain embodiments, at least one solution comprises sucrose at a concentration of between 52-58% (w/w) sucrose and at least another solution comprises sucrose at a concentration of between 57-63% (w/w) sucrose. In certain embodiments, at least one solution comprises sucrose at a concentration of between 54-56% (w/w) sucrose and at least another solution comprises sucrose at a concentration of between 59-61% (w/w) sucrose. In certain embodiments, at least one solution comprises sucrose at a concentration greater than about 54% (w/w) sucrose and at least another solution comprises sucrose at a concentration greater than about 59% (w/w) sucrose. In certain embodiments, at least one solution comprises sucrose at a concentration equal to or greater than about 55% (w/w) sucrose and at least one solution comprises sucrose at a concentration equal to or greater than about 60% (w/w) sucrose. In certain embodiments, at least one solution comprises sucrose at a concentration equal of about 55% (w/w) sucrose and at least one solution comprises sucrose at a concentration of about 60% (w/w) sucrose. In certain embodiments, the solution comprising AAV is a buffered solution (e.g., TrisHCl/NaCl buffer). In certain embodiments, the solution comprising AAV is a buffered ethylene glycol solution as described above.

In exemplary aspects, the method comprises loading into a rotor (e.g., a zonal rotor) an AAV fraction (e.g., a solution comprising AAV) with at least three sucrose solutions, each sucrose solution of which (a) has a different sucrose concentration and (b) comprises sucrose at a concentration ranging from about 45% (w/w) to about 65% (w/w) sucrose, optionally ranging from about 50% (w/w) to about 60% (w/w). In certain embodiments, at least one solution comprises sucrose at a concentration of between 47-53% (w/w) sucrose, at least another solution comprises sucrose at a concentration of between 52-58% (w/w) sucrose, and at least another solution comprises sucrose at a concentration of between 57-63% (w/w) sucrose. In certain embodiments, at least one solution comprises sucrose at a concentration of between 49-51% (w/w) sucrose, at least another solution comprises sucrose at a concentration of between 54-56% (w/w) sucrose, and at least another solution comprises sucrose at a concentration between 59-61% (w/w) sucrose. In certain embodiments, at least one solution comprises sucrose at a concentration greater than about 49% (w/w) sucrose, at least another solution comprises sucrose at a concentration greater than about 54% (w/w) sucrose, and at least another solution comprises sucrose at a concentration greater than about 59% (w/w) sucrose. In certain embodiments, at least one solution comprises sucrose at a concentration equal to or greater than about 50% (w/w) sucrose, at least one solution comprises sucrose at a concentration equal to or greater than about 55% (w/w) sucrose, and at least one solution comprises sucrose at a concentration equal to or greater than about 60% (w/w) sucrose. In certain embodiments, at least one solution comprises sucrose at a concentration equal of about 50% (w/w) sucrose, at least one solution comprises sucrose at a concentration of about 55% (w/w) sucrose, and at least one solution comprises sucrose at a concentration of about 60% (w/w) sucrose. In certain embodiments, the solution comprising AAV is a buffered solution (e.g., TrisHCl/NaCl buffer). In certain embodiments, the solution comprising AAV is a buffered ethylene glycol solution as described above.

In exemplary aspects, the method comprises loading into the rotor (e.g., zonal rotor) three, four, five, six, or more sucrose solutions, each sucrose solution of which (a) has a different sucrose concentration and (b) comprises sucrose at a concentration ranging from about 45% (w/w) to about 65% (w/w) sucrose, optionally ranging from about 50% (w/w) to about 60% (w/w), or optionally ranging from about 55% (w/w) to about 60% (w/w). The complete ranges of sucrose concentrations are as listed above with respect to the ranges of sugar solutions. The ratio of sucrose solutions to AAV fraction and/or other sugar solutions is as listed above.

In exemplary aspects, the volume of the sucrose solution with the lowest sucrose concentration and the volume of the sucrose solution with the highest sucrose concentration are about 20% to about 30% and about 20% to about 30% of the rotor volume, respectively. In certain embodiments, the volume of the sucrose solution with the lowest sucrose concentration, the volume of the sucrose solution with the intermediate sucrose concentration and the volume of the sucrose solution with the highest sucrose concentration are each about 25% of the rotor volume. In exemplary aspects, the volume of the sucrose solution with the lowest sucrose concentration, the sucrose solution with the intermediate sucrose concentration and the sucrose solution with the highest sucrose concentration are about 20% to about 30%, about 10% to about 15%, and about 10% to about 15% of the rotor volume, respectively. In certain embodiments, the volume of the sucrose solution with the lowest sucrose concentration, the sucrose solution with the intermediate sucrose concentration and the sucrose solution with the highest sucrose concentration are about 25%, about 12.5%, and about 12.5% of the rotor volume, respectively. In certain embodiments, the ultracentrifugation core volume or the rotor volume is within a range of about 200 mL to about 10,000 mL, within a range of about 700 mL to about 8500 mL, or within a range of about 700 mL to about 7,700 mL.

A wide variety of ultracentrifugation cores are available and known to those in the art. For example, the smallest ultracentrifugation core available is the 200 mL Hitachi CC40S, while the largest core is the 8,000 mL Hitachi CC40.

The CC40CT3 Core E all other continuous flow ultracentrifuges and cores from other suppliers may be used.

In exemplary aspects, the method comprises operating an ultracentrifuge comprising the rotor (e.g., a zonal rotor) in batch mode, whereupon a sugar gradient is formed. In certain embodiments, the ultracentrifuge is operated at a first rotational speed of less than 10,000 rpm. In certain embodiments, the first rotational speed is about 3,000 rpm to about 6,000 rpm (e.g., 4,000 rpm or 5,000 rpm) and the first rotation speed is achieved within about 15 to about 25 minutes. In certain embodiments, the ultracentrifuge is operated at a first rotational speed at a temperature between about 2° C. and about 10° C. In certain embodiments, the ultracentrifuge is operated at the first rotational speed for the purpose of ultimately achieving a higher rotational speed. In certain embodiments, the ultracentrifuge is accelerated to a second rotational speed, which is at least 2× or at least 3× greater than the first rotational speed. In certain embodiments, second rotational speed is achieved upon accelerating the ultracentrifuge for about 5 to about 60 min. In certain embodiments, the ultracentrifuge is operated at a second rotational speed greater than or about 30,000 rpm. In certain embodiments, the ultracentrifuge is operated at a second rotational speed greater than or about 30,000 rpm and less than or about 50,000 rpm. In certain embodiments, the second rotational speed is between about 30,000 rpm and about 40,000 rpm, e.g., about 35,000 rpm. In certain embodiments, ultracentrifuge is operated at a second rotational speed for at least or about 3 hours, at least or about 4 hours, at least or about 5 hours, or at least or about 6 hours, at least or about 10 hours, at least or about 12 hours, at least or about 14 hours, at least or about 16 hours, at least or about 18 hours, at least or about 20 hours, or at least or about 22 hours. In certain embodiments, ultracentrifuge is operated at a second rotational speed for at least or about 4 hours. In certain embodiments, ultracentrifuge is operated at a second rotational speed for about 16 to about 20 hours. In certain embodiments, ultracentrifuge is operated at a second rotational speed for at least or about 16 hours. In certain embodiments, the ultracentrifuge is operated at a second rotational speed at a temperature between about 15° C. and about 30° C., e.g., at least about 18° C., between about 20° C. and about 25° C. (e.g., about 22° C.). In certain embodiments, the ultracentrifuge is subsequently operated to decelerate the rotational speed, e.g., to the first rotational speed, e.g., about 4,000 rpm, optionally, over the course of about 5 to about 90 minutes. In certain embodiments, the deceleration occurs at a temperature less than about 18° C., between about 2° C. and about 10° C., or less than about 8° C. In certain embodiments, the ultracentrifuge is operated at a temperature less than about 8° C. at least 30 minutes before the ultracentrifuge is stopped.

Figure 8:
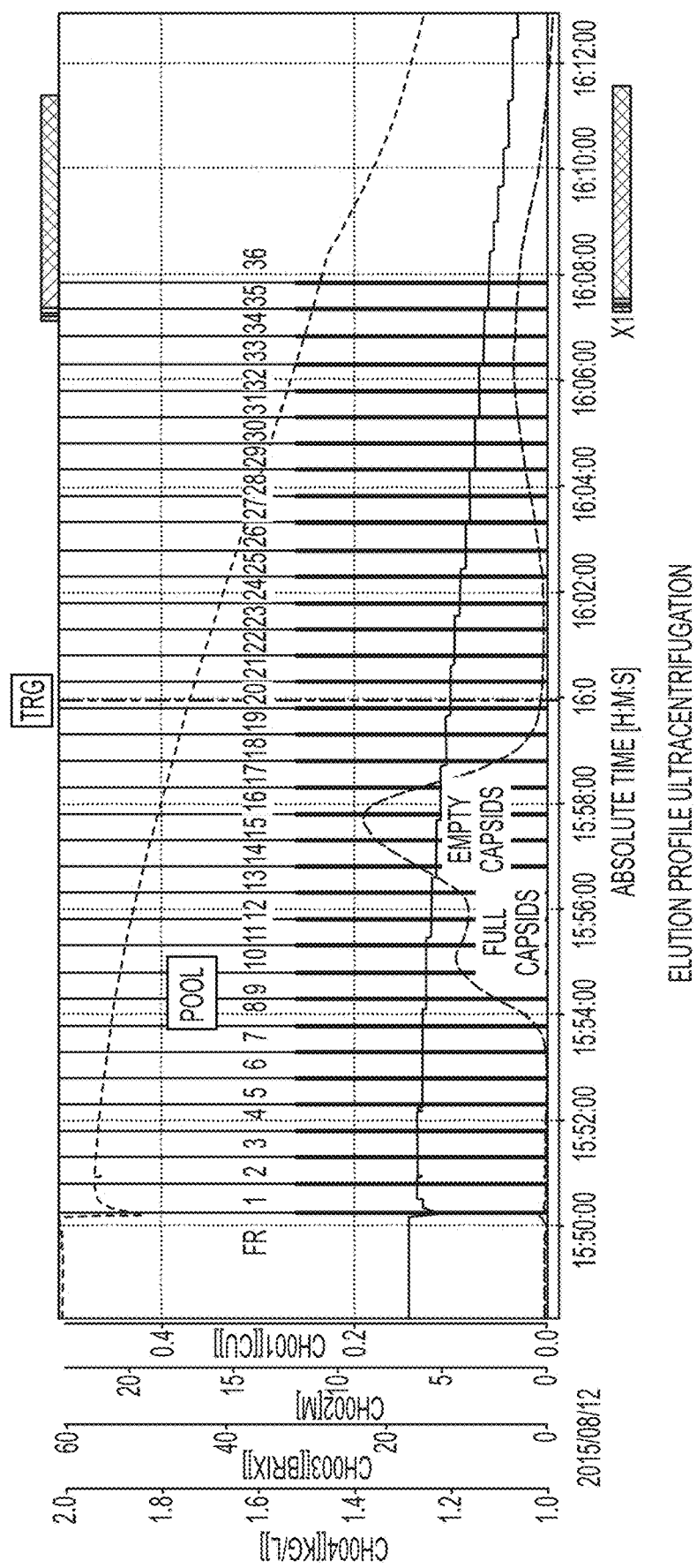
FIG. 8 is a graph of the ultracentrifugation elution profile separating the empty versus full capsids. The fractions were each 50 ml.

In exemplary aspects, the method comprises obtaining a fraction of the sugar gradient to obtain an AAV fraction. In certain embodiments, the obtained AAV fraction has greater than 60% of full capsids. In certain embodiments, the obtained AAV fraction has 70-80% of full capsids. In certain embodiments, one or more fractions of the sugar gradient are obtained, and, in certain embodiments, the fractions are obtained from the gradient containing higher density fractions. In certain embodiments, the fractions equivalent to fractions 7-11 as shown in FIG. 8 are obtained. In certain embodiments, the fractions equivalent to fractions 10-14 as described in Example 9 are obtained. In certain embodiments, the fractions equivalent to fractions 1-8 as described in Example 16 are obtained. In certain embodiments, any fraction containing full capsids from empty capsids are separated by their density difference as they elute from the rotor in the density gradient. The control of the separation can be achieved either by fractionating in small volumes followed by analytical testing [e.g., as described in Example 9], or by fractionating according to UV signals from inline measurement of UV signals (e.g. UV254 nm/UV280 nm signals and inline control of their ratio). In certain embodiments, the AAV fraction is obtained from the zone with higher sucrose density at step ultracentrifugation. In certain embodiments, the obtained AAV (e.g., AAV8) fraction is confirmed as being mostly full capsids (e.g., >60% full capsids) by the ratio of [the UV signal at 254 nm]/[the UV signal at 280 nm] independent from the volume of the UC core used. If this ratio (OD 254 nm/OD 280 nm)>1, then the fraction is full capsids.

In exemplary aspects, the methods of the present disclosures yield an AAV product wherein at least 50% of the AAV capsids are full AAV capsids. In certain embodiments, the methods of the present disclosures yield an AAV product wherein at least 55% of the AAV capsids are full AAV capsids. In certain embodiments, the methods of the present disclosures yield an AAV product wherein at least 60% of the AAV capsids are full AAV capsids. In certain embodiments, the methods of the present disclosures yield an AAV product wherein at least 70% of the AAV capsids are full AAV capsids. In certain embodiments, the methods of the present disclosures yield an AAV product wherein at least 80% of the AAV capsids are full AAV capsids. In certain embodiments, the methods of the present disclosures yield an AAV product wherein at least 90% of the AAV capsids are full AAV capsids. It will be appreciated that "at least 50%" refers to a range wherein 50% is the minimum percentage. The maximum percentage of such a range is, in various embodiments, 100%, although sub-ranges also are contemplated herein where the maximum percentage is, e.g., 99%, 98%, 95%, 80%, 85%, and the like. Suitable methods for measuring the amount of full capsids vs. empty capsids are known in the art and include, for example, negative stain transelectron microscopy and analytic anion exchanger chromatography using a detection set-up that allows discrimination between full and empty capsids. See, e.g., Lock et al., Human Gene Ther Part B 23:56-64 (2012); and Qu et al., J Virol Methods 140: 183-192 (2007).

In exemplary aspects, the sugar (e.g., sucrose) solutions differ in concentration by about 5% (w/w) to about 15% (w/w). In certain embodiments, the sugar solutions differ in sucrose-equivalent concentration by about 5% (w/w) to about 10% (w/w), about 4% (w/w) to about 8% (w/w), or about 2% (w/w) to about 3% (w/w). In certain embodiments, the sugar solutions comprise sucrose and differ in sucrose concentration by about 5% (w/w) to about 10% (w/w), about 4% (w/w) to about 8% (w/w), or about 2% (w/w) to about 3% (w/w).

In exemplary aspects, the method of purifying recombinant adeno-associated virus (rAAV) particles and/or the method of separating full viral particles from the empty capsids comprises ultracentrifuging a fraction comprising rAAV particles with two sucrose solutions, each sucrose solution comprising a different sucrose concentration, ranging from about 50% (w/w) to about 65% (w/w) at a first rotational speed of less than 10,000 rpm (e.g., 4,000 rpm) for about 15 min to about 45 min or about 17 min to about 25 min, and at a second rotational speed within the range of about 30,000 to about 40,000 rpm (e.g., 35,000 rpm) for at least 4 hours or about 16 to about 20 hours. In certain embodiments, one solution comprises sucrose at a concentration equal of about 55% (w/w) sucrose and one solution comprises sucrose at a concentration of about 60% (w/w) sucrose. In exemplary aspects, the ultracentrifugation step is carried out as essentially described in Example 6.

In exemplary aspects, the method of purifying recombinant adeno-associated virus (rAAV) particles and/or the method of separating full viral particles from the empty capsids comprises ultracentrifuging a fraction comprising rAAV particles with three sucrose solutions, each sucrose solution comprising a different sucrose concentration, ranging from about 45% (w/w) to about 65% (w/w), at a first rotational speed of less than 10,000 rpm (e.g., 4,000 rpm) for about 15 min to about 45 min or about 17 min to about 25 min, and at a second rotational speed within the range of about 30,000 to about 40,000 rpm (e.g., 35,000 rpm) for at least 4 hours or about 16 to about 20 hours. In certain embodiments, one solution comprises sucrose at a concentration equal of about 50% (w/w) sucrose, one solution comprises sucrose at a concentration of about 55% (w/w) sucrose, and one solution comprises sucrose at a concentration of about 60% (w/w) sucrose. In exemplary aspects, the ultracentrifugation step is carried out as essentially described in Examples 7 or 9.

Source of rAAV Particles

With regard to the methods of the present disclosure, the AAV may be of any AAV serotype. In certain embodiments, the AAV purified by the methods described herein are of AAV1 serotype, AAV2 serotype, AAV3 serotype, AAV4 serotype, AAV5 serotype, AAV6 serotype, AAV7 serotype, AAV8 serotype, AAV9 serotype, or AAV10 serotype. In certain embodiments, the AAV particles purified by the methods described herein are of AAV8 serotype. With regard to the methods of the invention, the AAV fraction which is loaded into the rotor is in exemplary aspects a concentrated AAV fraction. In certain embodiments, the AAV fraction loaded into the rotor comprises at least $1 \times 10^{10}$, $1 \times 10^{11}$ or $1 \times 10^{12}$ AAV capsids per mL. In certain embodiments, the AAV fraction loaded into the rotor comprises at least $1 \times 10^{12}$ AAV capsids per mL, wherein the AAV capsids include empty AAV capsids and full AAV capsids.

In certain embodiments, the AAV fraction represents an AAV fraction produced by transfected host cells. In certain embodiments, the AAV fraction represents a supernatant harvested from a cell culture comprising host cells transfected with a triple plasmid system, wherein one plasmid of the system comprises a gene or cDNA of interest, one plasmid encodes capsid protein VP1, capsid protein VP2 and/or capsid protein VP3. In certain embodiments, VP1, VP2, and/or VP3 are AAV8 VP1, AAV8 VP2, and/or AAV8 VP3. Triple plasmid transfection for purposes of rAAV production is known in the art. See, e.g., Qu et al., 2015, supra, and Mizukami et al., "A Protocol for AAV vector production and purification." PhD dissertation, Division of Genetic Therapeutics, Center for Molecular Medicine, 1998; and Kotin et al., Hum Mol Genet 20(R1): R2-R6 (2011). In certain embodiments, the transfection may be carried out using inorganic compounds, e.g., calcium phosphate, or organic compounds, polyethyleneimine (PEI), or non-chemical means, e.g., electroporation.

In certain embodiments, the host cells are adherent cells. In certain embodiments, the host cells are suspension cells. In certain embodiments, the host cells are HEK293 cells or Sf9 cells (e.g., baculovirus infected Sf9 cells). In certain embodiments, the cell culture comprises culture medium which is serum and protein free. In certain embodiments, the medium is chemically defined and is free of animal derived components, e.g., hydrolysates.

In certain embodiments, the fraction comprising rAAV particles represents a fraction comprising HEK293 cells transfected with a triple plasmid system. In certain embodiments, the fraction comprising rAAV particles represents a fraction of a supernatant harvested about 3 to about 5 days after transfection of the HEK293 cells or when the cell culture has a cell density of greater than or about $5 \times 10^6$ cells/mL and has a cell viability of greater than or about 50%. In certain embodiments, the fraction comprising rAAV particles represents a fraction comprising HEK293 cells as described in Example 1.

In certain embodiments, the AAV is prepared by a triple plasmid transfection followed by harvest from one to 5 days later. In certain embodiments, the AAV is prepared from cell disruption.

In certain embodiments, the AAV is prepared by the following: The HEK293 cells are adherent and grown in a commercially-available culture medium that may be chemically-defined and may be free of animal-derived components, e.g. serum and proteins. The cells are cultured to a cell density of about $3 \times 10^6$ to about 12 cells/ml, e.g., about $6 \times 10^6$ to about 10 cells/ml. The cells are then split in about a 1:2 ratio such that the cell density is about $3-5 \times 10^6$ cells/ml. After the split, the cells may be transfected with three plasmids that include (1) a helper plasmid capable of providing one or more helper viral functions essential AAV production, (2) a plasmid that encodes for one or more genes involved in capsid generation, replication and packaging of the virus, and (3) a plasmid comprising a gene of interest (GOI) to be packaged into the resulting rAAV particle. For example, the GOI may be a vector DNA comprising human coagulation Factor IX Padua in a single stranded self-complementary form, with the vector DNA having a full length of 2.6 kB. As another example, the GOI may be a vector DNA comprising human coagulation Factor IX Padua in a double stranded self-complementary form, with the vector DNA having a full length of 4.8 kB. As another example, the GOI may be a vector DNA comprising a B-domain deleted human coagulation Factor VIII in a single stranded self-complementary form, with the vector DNA having a full length of 4.8 kB. Other GOI may be used. Transfection may be carried out in a transient manner, such as by using cationic polymers. Before elution, the HEK293 cell line may be cultivated for at least about 3 days, e.g., 3-5 days, before harvesting.

Additional Steps

The methods of the present disclosure comprise any combination of steps disclosed herein, and may optionally be combined with one or more additional steps. Accordingly, in exemplary aspects, the methods of the present disclosure further comprise the step of transfecting host cells with a triple plasmid system as described herein. In exemplary aspects, the methods of the present disclosure comprise harvesting a supernatant from a cell culture comprising host cells, e.g., HEK293 cells or Sf9 (e.g., baculovirus infected Sf9 cells), transfected with a triple plasmid system. In exemplary aspects, the methods of the present disclosure comprise harvesting the supernatant about 3 to about 5 days after transfection of the HEK293 cells or when the cell culture has a cell density of greater than or about $5 \times 10^6$ cells/mL and has a cell viability of greater than 50%. In certain embodiments, the AAV is prepared from cell disruption. In exemplary aspects, the transfection and harvesting step occurs prior to the ultracentrifugation step described herein. The methods of the present disclosure may comprise yet other additional steps, which may further increase the purity of the AAV and remove other unwanted components and/or concentrate the fraction and/or condition the fraction for a subsequent step. The additional steps may occur before or after the ultracentrifugation step described above.

In exemplary aspects, the method comprises a depth filtration step. In exemplary aspects, the method comprises subjecting a fraction of a transfected HEK293 cell culture supernatant to depth filtration using a filter comprising cellulose and perlites and having a minimum permeability of about 500 L/m$^2$. In exemplary aspects, the method further comprises use of a filter having a minimum pore size of about 0.2 μm. In exemplary aspects, the depth filtration is followed by filtration through the filter having a minimum pore size of about 0.2 μm. In exemplary aspects, one or both of the depth filter and filter having a minimum pore size of about 0.2 μm are washed and the washes are collected. In exemplary aspects, the washes are pooled together and combined with the filtrate obtained upon depth filtration and filtration with the filter having a minimum pore size of about 0.2 μm. Example 2 provides an exemplary method of depth filtration and filtration through a filter having a minimum pore size of about 0.2 μm. In exemplary aspects, the depth filtration step and other filtration step occurs prior to the ultracentrifugation step described herein.

In certain embodiments, harvesting is conducted by the following: The supernatant of the cell culture is harvested at this time via depth filtration, e.g., by filtering about 150 to about 250 L of AAV-containing cell suspension through a depth filter element and a polyethersulfone element. The flow rate can be from about 40 kg/hour to about 280 kg/hour, or from about 60 kg/hour to 240 kg/hour. The total pressure is less than 1.7 bar. The two filters are flushed with about 10 to about 30 L of Tris Buffered Saline (TBS) buffer. The filtered fermentation broth, or harvest, is then collected. The depth filtration procedure can remove at least 70% of the protein and 60% of HEK293 cell DNA, while retaining at least 60% of 65% of the AAV particles.

In certain embodiments, the harvest containing the AAV fraction is subjected to ultrafiltration/diafiltration (UF/DF) and TFF to concentrate and condition the harvest as follows: The harvest is concentrated about 10-fold to about 20-fold to a target volume of about 10 L to about 15 L using TFF. The concentrated harvest is then subjected to two diafiltration steps to condition the concentrated harvest to a pH of about 8.3 to about 8.7 and a conductivity of about 13 mS/cm to about 17 mS/cm. Each diafiltration step may be performed via a 5-fold volume exchange with a diafiltration buffer, e.g., the first buffer comprises 50 mM TRIS and 500 mM NaCl, having a pH of 8.5±0.2, and at 25° C., and the second buffer comprises 50 mM TRIS and 125 mM NaCl, having a pH of 8.5±0.2, and at 25° C. TFF is then undertaken to concentrate the retentate to a final target volume of about 8 L to about 12 L. The concentrate is then filtered through a 0.2 μm filter element. The AAV yield may increase by flushing the filter element with about 1.5 to about 2.5 of the second diafiltration buffer.

In exemplary aspects, the methods of the present disclosure comprise one or more chromatography steps. In exemplary aspects, the methods comprise a negative chromatography step whereby unwanted components bind to the chromatography resin and the desired AAV does not bind to the chromatography resin. In exemplary aspects, the methods comprise a negative anion exchange (AEX) chromatography step, or an AEX chromatography step in the "non-binding mode". Example 4 describes such a step. Accordingly, in exemplary embodiments, the methods of purifying AAV particles comprise performing negative anion exchange (AEX) chromatography on a fraction comprising AAV particles by applying the fraction to an AEX chromatography column or membrane under conditions that allow for the AAV to flow through the AEX chromatography column or membrane and collecting AAV particles. In exemplary aspects, the fraction is applied to the AEX chromatography column or membrane with a loading buffer comprising about 100 mM to about 150 mM salt, e.g., NaCl, optionally, wherein the pH of the loading buffer is about 8 to about 9. In exemplary aspects, the loading buffer comprises about 115 mM to about 130 mM salt, e.g., NaCl, optionally, wherein the loading buffer comprises about 120 mM to about 125 mM salt, e.g., NaCl. In exemplary aspects, the negative AEX step occurs prior to the ultracentrifugation step described herein.

In exemplary aspects, the methods of the present disclosure comprise concentrating an AAV fraction using an ultra/diafiltration system. In exemplary aspects, the methods of the present disclosure comprise one more tangential flow filtration (TFF) steps. In exemplary aspects, the AAV fraction undergoes ultra-/dia-filtration. In exemplary aspects, the AAV fraction is concentrated with the ultra/diafiltration system before a step comprising performing negative AEX chromatography, after a step comprising performing negative AEX chromatography, or before and after comprising performing negative AEX chromatography. Examples 3 and 5 describe such TFF steps. In exemplary aspects, the TFF steps occur prior to the ultracentrifugation step described herein.

In certain embodiments, an additional TFF step is performed after negative AEX chromatography as follows: The AAV-containing flow through fraction obtained from AEX chromatography is concentrated and diafiltered against a buffer, e.g. one comprising about 500 mM NaCl, about 50 mM TrisHCl; at pH of about 8.3 to about 8.7, to condition the product for ultracentrifugation. A TFF step is then carried out.

In certain embodiments, empty and full AAV particles are separated from one another by "two sucrose protocol" ultracentrifugation as follows. A concentrate comprising AAV in a TrisHCl/NaCl buffer followed by a first sucrose solution comprising sucrose in a 55% (w/w) sucrose concentration and then a second sucrose solution comprising sucrose in a 60% (w/w) sucrose concentration. In certain embodiments, the AAV solution comprises about 50 mM TrisHCl, and about 500 mM NaCl. In certain embodiments, the sucrose solution comprises about 50 mM TrisHCl and about 136 mM NaCl. Ultracentrifugation is initially conducted at about 4,000 rpm at a temperature of 2-10° C., with the speed increased to about 33,000 rpm to about 37,000 rpm, the temperature increased to about 20° C. to about 25° C., and then held for about 4 hours, about 14 hours to about 20 hours, or from about 16 hours to about 20 hours. Fractions are then collected.

In certain embodiments, empty and full AAV particles are separated from one another by "two sugar protocol" ultracentrifugation as follows. A concentrate comprising AAV and a buffered ethylene glycol solution containing 45-50% (w/w) ethylene glycol in a TrisHCl/NaCl buffer followed by a first sucrose solution comprising sucrose in a 55% (w/w) sucrose concentration and then a second sucrose solution comprising sucrose in a 60% (w/w) sucrose concentration. In certain embodiments, the AAV solution comprises about 55% ethylene glycol, about 50 mM TrisHCl, and about 750 mM NaCl. In certain embodiments, the sucrose solution comprises about 50 mM TrisHCl and about 136 mM NaCl. Ultracentrifugation is initially conducted at about 4,000 rpm at a temperature of 2-10° C., with the speed increased to about 33,000 rpm to about 37,000 rpm, the temperature increased to about 20° C. to about 25° C., and then held for about 4 hours, about 14 hours to about 20 hours, or from about 16 hours to about 20 hours. Fractions are then collected.

In certain embodiments, empty and full AAV particles are separated from one another by "three sugar protocol" ultracentrifugation as follows. A concentrate comprising AAV in a TrisHCl/NaCl buffer followed by a first sucrose solution comprising sucrose in a 50% (w/w) sucrose concentration, a second sucrose solution comprising sucrose in a 55% (w/w) sucrose concentration, and a third sucrose solution comprising sucrose in a 60% (w/w) sucrose concentration. The first sucrose solution is loaded into the bottom of the rotor; followed by the second sucrose solution and the third sucrose solution. In certain embodiments, the AAV solution comprises about 50 mM TrisHCl, and about 500 mM NaCl. In certain embodiments, the sucrose solution comprises about 50 mM TrisHCl and about 136 mM NaCl. Ultracentrifugation is initially conducted at about 4,000 rpm at a temperature of 2-10° C., with the speed increased to about 33,000 rpm to about 37,000 rpm, the temperature increased to about 20° C. to about 25° C., and then held for about 3 hours to about 6 hours, from about 4 hours, about 14 hours to about 20 hours, or from about 16 hours to about 20 hours. Fractions are then collected.

In certain embodiments, empty and full AAV particles are separated from one another by "three sucrose protocol" ultracentrifugation as follows. A concentrate comprising AAV and a buffered ethylene glycol solution containing 45-50% (w/w) ethylene glycol in a TrisHCl/NaCl buffer followed by a first sucrose solution comprising sucrose in a 50% (w/w) sucrose concentration, a second sucrose solution comprising sucrose in a 55% (w/w) sucrose concentration, and a third sucrose solution comprising sucrose in a 60% (w/w) sucrose concentration. The first sucrose solution is loaded into the bottom of the rotor; followed by the second sucrose solution and the third sucrose solution. In certain embodiments, the AAV solution comprises about 55% ethylene glycol, about 50 mM TrisHCl, and about 750 mM NaCl. In certain embodiments, the sucrose solution comprises about 50 mM TrisHCl and about 136 mM NaCl. Ultracentrifugation is initially conducted at about 4,000 rpm at a temperature of 2-10° C., with the speed increased to about 33,000 rpm to about 37,000 rpm, the temperature increased to about 20° C. to about 25° C., and then held for about 3 hours to about 6 hours, from about 4 hours, about 14 hours to about 20 hours, or from about 16 hours to about 20 hours. Fractions are then collected.

In exemplary aspects, the methods of the present disclosure comprise treating a fraction comprising AAV particles with a solvent detergent to inactivate lipid enveloped viruses. Example 8 describes an exemplary method of lipid enveloped virus inactivation. In exemplary aspects, the solvent detergent treatment step occurs after the ultracentrifugation step described herein.

In exemplary aspects, the methods of the present disclosure comprise filtration of a fraction comprising rAAV particles to remove viruses of greater size than the rAAV particles in the fraction. In exemplary aspects, the method of the present disclosure comprises filtration of a fraction comprising AAV to remove viruses sized greater than or about 35 nm. In exemplary aspects, the pore size of the filter is in the nanometer range, and, in exemplary aspects, the method comprises nanofiltration. In exemplary aspects, the method of the present disclosure comprises use of a nanofilter of pore size in the range of 35 nanometer ±2 nanometer, as determined by a water flow method. An exemplary nanofilter having such pore size contains bundles of microporous hollow-fibers constructed of a natural hydrophilic cuprammonium regenerated cellulose. Classification of the type of filter is dependent on membrane structure, material, and vendor. In exemplary aspects, the nanofilter is tested with an integrity leakage test to confirm that the filter is free from pinholes or large defects and pre-washed with formulation buffer.

An exemplary nanofiltration is described herein as Example 10.

In exemplary aspects, the fraction comprising rAAV particles, e.g., an anion exchange eluate, is pre-diluted with elution buffer (PBS+600 mM NaCl) to adjust concentration of the virus particles.

In exemplary aspects, during the filtration step, a pressure difference over the filter is maintained. In exemplary aspects, the pressure (pressure drop across the filter) is about 0.02 MPa to about 0.1 MPa. In exemplary aspects, the pressure (e.g., pressure drop across the filter) is about 0.02 MPa to about 0.08 MPa. In case the filter is run in dead-end mode, the pressure difference can be effected by the feed pressure of the sample applied (i.e., by adjustment of a pump to a specific flow, which affects the feed pressure). In exemplary aspects, the filtration is conducted under constant pressure not exceeding 0.1 MPa in a dead-end mode through the nanofilter. In exemplary aspects, the filter is run in a tangential flow method. In exemplary aspects, the yield of recovered virus particles is increased by post-washing the nanofilter with buffer (e.g. formulation buffer). In exemplary aspects, post-integrity testing of the nanofilter is performed with a leakage test and/or a gold particle test to determine that the nanofilter pore size distribution does not change and that the nanofilter retains its integrity during filtration. In exemplary aspects, more than 50 L of solution is applied per $m^2$ filter area to increase the sample yield.

In exemplary aspects, the filtration step for removal of viruses larger than the rAAV particles occurs once during the process of the present disclosure. In exemplary aspects, the filtration step occurs twice during the process. In exemplary aspects, the filtration step for removal of viruses larger than the rAAV particles occurs after the ultracentrifugation step described herein. In exemplary aspects, the filtration step for removal of viruses larger than the rAAV particles occurs after a polish step.

In exemplary aspects, the methods of the present disclosure comprise a polish step comprising performing AEX chromatography, optionally with a column comprising tentacle gel. Example 8 describes an exemplary method comprising such a polish step. In exemplary aspects, the polish step occurs after the ultracentrifugation step described herein.

In exemplary aspects, the methods of the present disclosure comprise one or more quality control steps, e.g., steps to measure the potency. DNA/AAV ratio, or specific activity of the AAV fractions obtained after one or more steps (e.g., after each step) of the process. In exemplary aspects, the methods of the present disclosure comprise assaying for the presence of AAV in fractions by using qPCR, e.g., ITR qPCR. ITR qPCR is a quantitative PCR based assay to measure the amount of AAV Inverted Terminal Repeat (ITR) nucleic acid in the fraction. Other AAV-specific, or AAV8-specific sequences can be assayed by qPCR.

In exemplary aspects, the methods of the present disclosure comprise assaying for the presence of AAV in fractions by using ELISA. In exemplary aspects, the ELISA is a sandwich ELISA. In exemplary aspects, the sandwich ELISA comprises an antibody specific for an AAV epitope. In exemplary aspects, the AAV epitope is a conformational epitope present on assembled AAV capsids. A suitable method of testing DNA/AAV ratio is described herein as Example 12. As discussed herein, the ELISA may replace qPCR as a way to determine potency of an AAV fraction. In exemplary aspects, the methods of the present disclosure comprise testing an AAV fraction via an AAV-specific ELISA and the methods do not include a method of measuring potency via quantitative PCR. In exemplary aspects, the AAV-specific ELISA is sufficient to provide a representative reading on potency of the AAV fraction, because the majority of the capsids in the AAV fraction are full capsids.

In exemplary aspects, the methods of the present disclosure comprise an ELISA specific for AAV after one or more of the steps of the present disclosure. In exemplary aspects, the methods of the present disclosure comprise testing an AAV fraction obtained after ultracentrifugation via an AAV-specific ELISA to determine the DNA/AAV ratio of the AAV in that fraction. In exemplary aspects, the methods of the present disclosure comprise testing an AAV fraction obtained after depth filtration via an AAV-specific ELISA to determine the DNA/AAV ratio of the AAV in that fraction. In exemplary aspects, the methods of the present disclosure comprise testing an AAV fraction obtained after concentrating an AAV fraction using an ultra-/diafiltration system via an AAV-specific ELISA to determine the DNA/AAV ratio of the AAV in that fraction. In exemplary aspects, the methods of the present disclosure comprise testing an AAV fraction obtained after a tangential flow filtration (TFF) step via an AAV-specific ELISA to determine the DNA/AAV ratio of the AAV in that fraction. In exemplary aspects, the methods of the present disclosure comprise testing an AAV fraction obtained after negative anion exchange (AEX) chromatography via an AAV-specific ELISA to determine the DNA/AAV ratio of the AAV in that fraction. In exemplary aspects, the methods of the present disclosure comprise testing an AAV fraction obtained after a polish step via an AAV-specific ELISA to determine the DNA/AAV ratio of the AAV in that fraction.

In exemplary aspects, the method of the present disclosure comprises one or a combination of steps illustrated in FIG. 1. In exemplary aspects, the method of the present disclosure comprises all steps illustrated in FIG. 1.

An AAV product produced by a method of the present disclosures is further provided herein. In exemplary aspects, the AAV product comprises at least about $10^{12}$ virus particles (vp) produced from about 1000 L of starting material (e.g., cell culture) or at least about $10^{13}$ virus particles (vp) produced from about 1000 L of starting material (e.g., cell culture) and wherein at least 50% or at least 55% of the AAV capsids present in the AAV product are full AAV capsids. In exemplary aspects, the AAV product of the present disclosures is highly pure, highly potent and suitable for clinical use in humans. In exemplary aspects, the AAV product comprises AAV particles of a homogenous population and high purity. In exemplary aspects, the AAV product comprises full-length vector DNA. In exemplary embodiments, the AAV product is substantially free of unwanted contaminants, including but not limited to, AAV particles containing truncated or incomplete vector DNA, AAV particles with incomplete protein composition and oligomerized structures, or contaminating viruses, e.g., non AAV, lipid enveloped viruses. In exemplary embodiments, the AAV product contains a high amount of encoding cDNA of the protein of interest. In exemplary aspects, the AAV product of the present disclosure is suitable for administration to a human.

In exemplary aspects, the AAV product is sterile and/or of good manufacturing practice (GMP) grade. In exemplary aspects, the AAV product conforms to the requirements set forth in the U.S. Pharmacopeia Chapter 1046 or the European Pharmacopoeia on gene therapy medicinal products or as mandated by the U.S. Food and Drug Administration (USFDA) or the European Medicines Agency (EMA). In exemplary aspects, the AAV product is a ready-to-use product for direct administration to a human with little to no processing or handling.

The following examples are given merely to illustrate the present invention and not in any way to limit its scope.

EXAMPLES

Example 1

The following example describes an exemplary method of transfecting a HEK293 cell line with a triple plasmid system to produce rAAV particles comprising a nucleic acid encoding a protein of interest.

Adherent HEK293 cells are grown in suspension conditions in a commercially-available culture medium that is chemically-defined and free of animal-derived components, protein and serum. The cells are cultured to a cell density of approximately $6\text{-}10 \times 10^6$ cells/ml. Before transfection a split of about 1:2 is performed to reach a cell density of approximately $3\text{-}5 \times 10^6$ cells/ml.

The cells are transfected with three plasmids: (1) a helper plasmid, which provides helper viral functions essential for a productive AAV infection, (2) the repcap-plasmid, which carries all information regarding capsid generation, replication and packaging of the virus, and (3) a plasmid containing the gene of interest (GOI), which is packaged into the resulting rAAV particle. For example, the GOI can be a Factor IX Padua vector DNA (single stranded (~2.6 kb) or double stranded (~4.8 kb)) or Factor VIII single stranded vector DNA (~4.8 kb).

Transient transfection of the HEK293 cells is carried out using the cationic polymer, polyethylenimine (PEI). Briefly, PEI and plasmid DNA are incubated for more than 10 minutes at temperatures between 4 to 37° C. prior to blending the transfection mix with the cell culture, in order for pre-complex formation of PEI and plasmid DNA to take place. Pre-formed complexes are added to the cell culture along with the transfection mix for and incubated for about 3 to 4 hours at a temperature between 30° C. and 40° C., e.g., about 37° C. The transfection is stopped by adding a known stop medium comprising, for example, a medium, e.g., Hyclone™ CDM4HEK293, a chemically defined, animal component free and protein-free cell culture medium, including 0.6 g/L glutamine, into the transfected culture.

Figure 2:
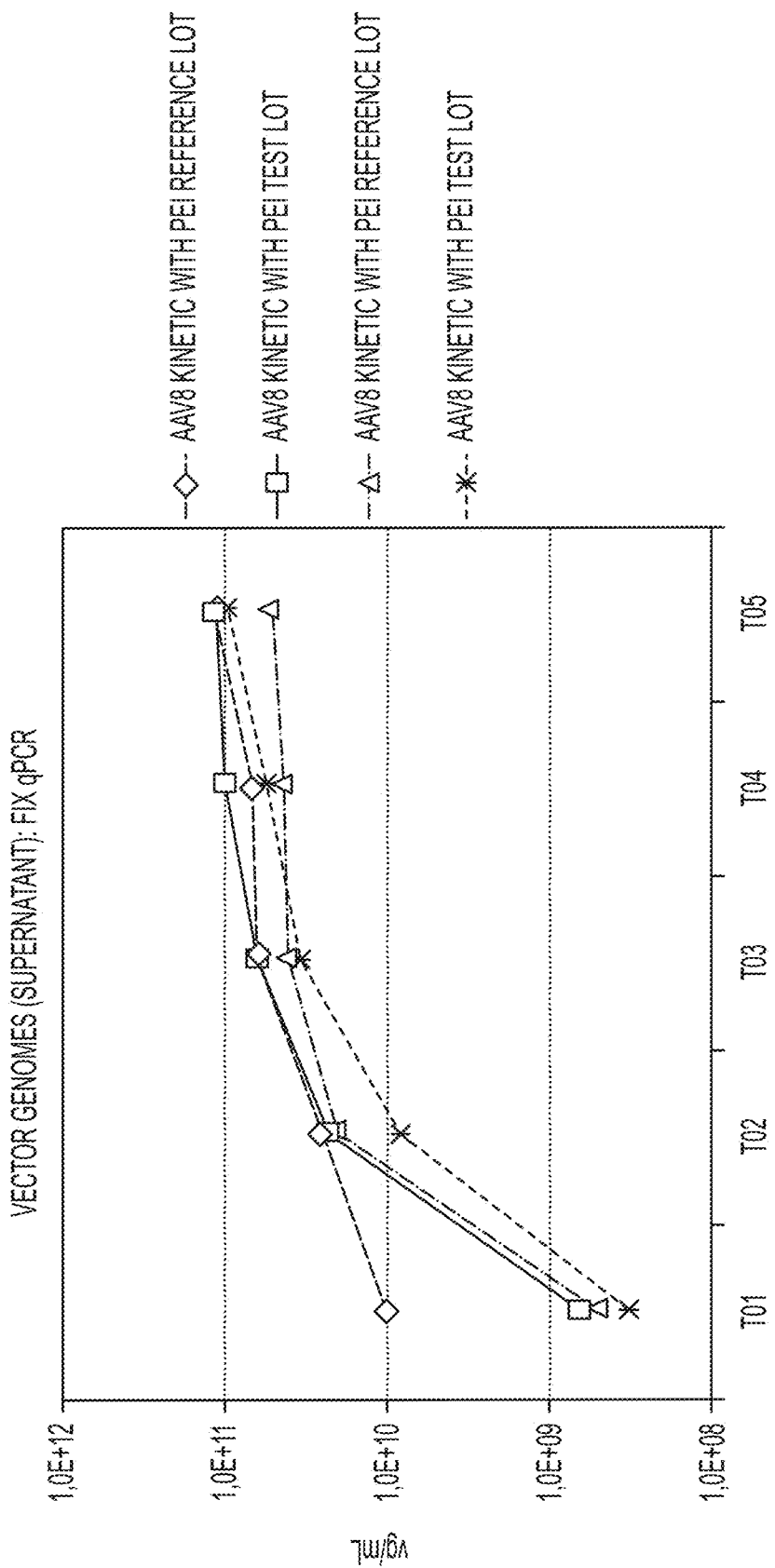
FIG. 2 is a graph of the amount of virus particles (viral grams) per ml of supernatant of a transfected cell culture plotted over a time course (days). Propagation of AAV8 in HEK293 cell cultures under established standard conditions (e.g. pH, Temp, agitation rate) in 2 L scale (4 parallel runs with two different PEI lots): increase of titer in cell culture supernatant over time measured by FIX specific qPCR (T01=transfection day 1, T02=transfection 2, etc.). The titer was measured by FIX specific qPCR in 3×2 L scale bioreactors.
Figure 3:
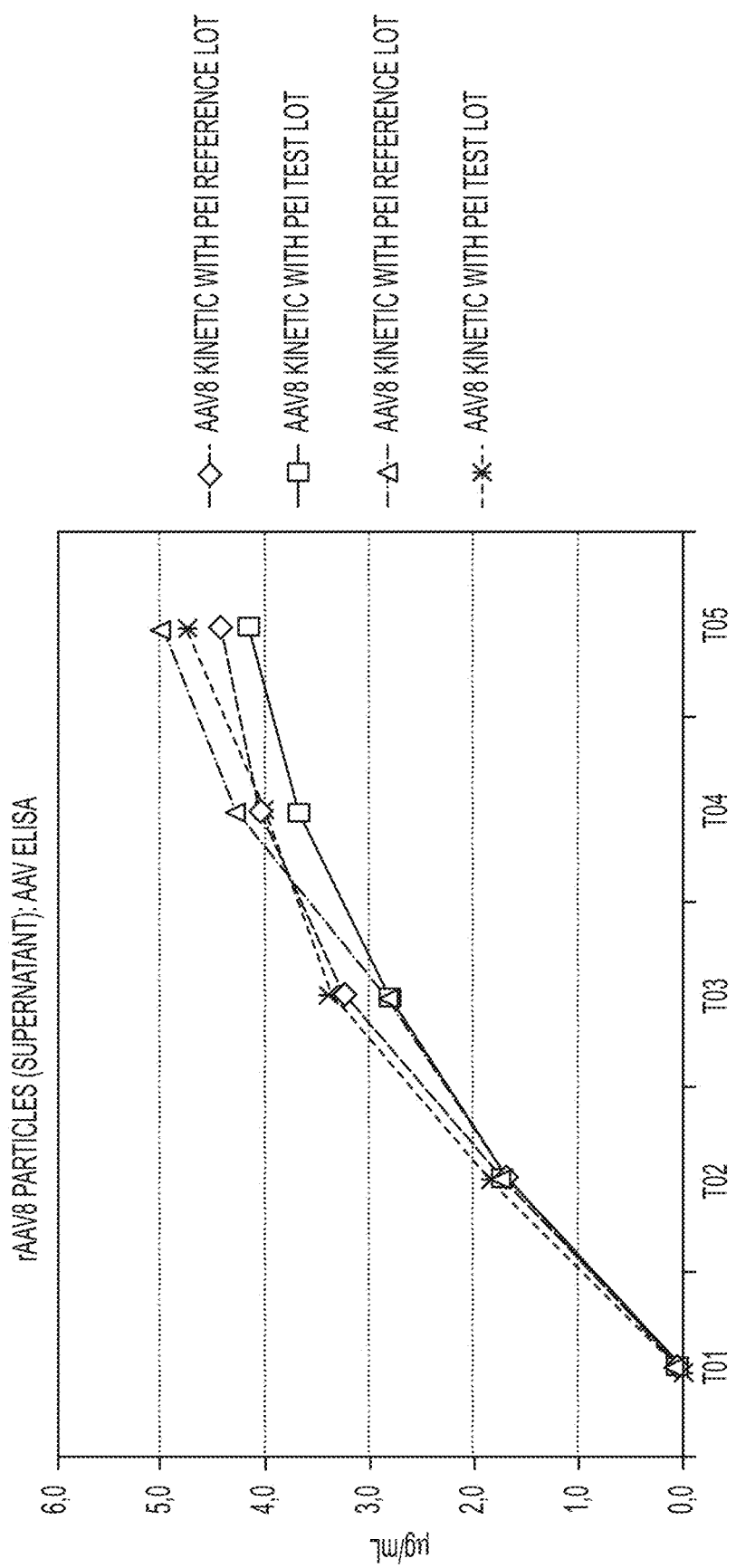
FIG. 3 is a graph of the amount of virus particles (viral grams) per ml of supernatant of a transfected cell culture plotted over a time course (days). Propagation of AAV8 in HEK293 cell cultures under established standard conditions (e.g. pH, Temp, agitation rate) in 2 L scale (4 parallel runs with two different PEI lots): increase of titer in cell culture supernatant over time measured by an AAV-specific ELISA (T01=transfection day 1, T02=transfection 2, etc.). The vector genome titer was measured by an AAV-specific ELISA in 3×2 L scale bioreactors.

The rAAV particles carrying the GOI are in the HEK293 cell line over a period of 3-5 days post-transfection. As shown in FIGS. 2 and 3, the HEK293 cell culture exhibits high cell densities (e.g., greater than about $5 \times 10^6$ cells/mL) with a viability of >50% at a time that is about 5 days post-transfection.

Example 2

The following example describes an exemplary method of harvesting the supernatant of a transfected HEK293 cell culture.

Figure 4:
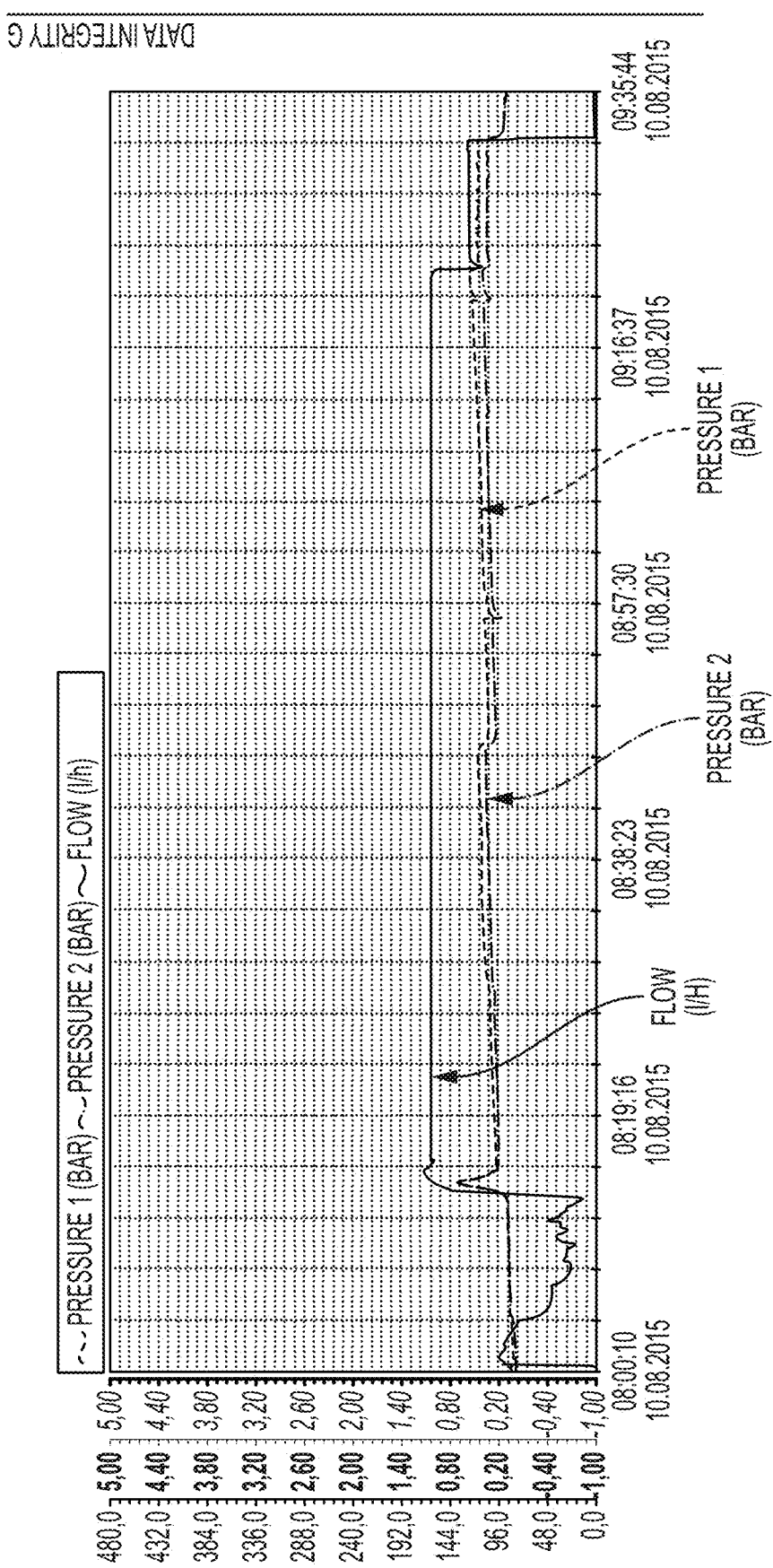
FIG. 4 is a graph of the pressure and flow rate during the depth filtration step, as measured continuously via two pressure sensors (pressure 1 before depth filtration, pressure 2 before membrane filter after depth filter; flow=flow rate as measured with flow meter).

As discussed in Example 1, rAAV production occurs within the first 3 to about 5 days after transfection. At the end of this timeframe, the HEK293 cell culture exhibits high cell densities (e.g., greater than about $5 \times 10^6$ cells/mL) with a viability of >50%. The supernatant of the cell culture was harvested at this time via depth filtration. The AAV particles were separated from cells and cell debris by filtering about 200 L (±20 L) AAV-containing cell suspension through a cellulose-based depth filter element (e.g. Pall, STAX K900P; 4 m$^2$) and a 0.2 µm polyethersulfon (PES) filter element (e.g. Pall, ECV; 2×5 inch, in parallel). The typical flow rate through the filters was 160±100 kg/hour and the total pressure was <1.7 bar. The two filters were flushed with about 10-30 L Tris Buffered Saline (TBS) buffer (20 mM Tris, 8 g/L NaCl, pH 7.4±0.2 at 25° C.). Together with the filter flush, the filtered fermentation broth is collected in a 500 L bag and is referred to as a harvest. Harvesting step parameters and characterization of the harvest (yield) after the harvesting step are found in Tables 1 and 2, respectively. FIG. 4 provides a continuous recording of pressure and flow rate of the harvest step.

TABLE 1

Harvest Step Parameters

| Process Stage | Parameter/Material | Value |
|---|---|---|
| Bioreactor conditions during harvest | Temperature for harvest start | 19-37° C. |
| | Working volume start filtration | 200 +/− 20 L |
| Depth filter | Membrane type | Pall, STAX K900P |
| | Membrane material | Cellulose based |
| | Area depth filter of K900 STAX | 4 (=2*2) m$^2$ |
| | Pre rinse volume (VE-water) | >50 L/m$^2$ |
| | Container between STAX and ECV | No, stax and ecv online |
| 0.2 µm filter | Filter type | Pall, Supor ECV |
| | Filter material | PES (Polyethersulfon) |
| | Pore size | 0.2 µm |
| | Number of filter elements | 2*5 inch |
| | Area 0.2 um filter (ECV; 5 inch) | 1.04 m$^2$ |
| Filtration parameters | Typical flow rate | 160 +/− 100 kg/hour |
| | Total pressure (depth + 0.2 µm) | <1.7 bar |
| | Filter flush | TBS buffer |
| | filter flush volume (depth + 0.2 µm) | 10-30 L |
| | Collection of filtrate and flush | Pall, 200 L Allegro Mixer |

TABLE 2

YIELD CHARACTERISTICS

| Sample code: | Volume [ml] | Turbidity [NTU] | Protein by Bradford | | ITR-qPCR | |
|---|---|---|---|---|---|---|
| | | | [µg/ml] | Total [mg] | [vg/ml] | Total (vg) |
| Load | 200.000 | n.d. | 597.5 | 119500− | 1.09E+12 | 2.18E+17− |
| STX_1 | — | 0.160 | 43 | — | 1.33E+11 | — |
| STX_2 | — | 1.450 | 79.34 | — | 3.95E+11 | — |
| STX_3 | — | 2.250 | 211 | — | 5.64E+11 | — |
| STX_F | — | 3.480 | 164 | — | 4.17E+11 | — |
| ECV_1 | — | 0.170 | 25 | — | 1.26E+11 | — |
| ECV_2 | — | 0.170 | 79 | — | 3.01E+11 | — |
| ECV_3 | — | 0.520 | 77 | — | 4.01E+11 | — |
| ECV_4 | — | 0.480 | 86 | — | 3.82E+11 | — |
| ECV_5 | — | 0.850 | 198 | — | 5.09E+11 | — |
| ECV_6 | — | 1.670 | 251 | — | 6.14E+11 | — |
| ECV_P | 201.800 | 2.530 | 169 | 34052 | 5.24E+11 | 1.06E+17 |

| Sample code: | AAV ELISA | | HEK DNA | | HEK293 HCP ELISA | |
|---|---|---|---|---|---|---|
| | [µg/ml] | Total [mg] | [ng/ml] | Total [µg] | [µg/ml] | Total [mg] |
| Load | 3.65 | 730− | 800.0 | 160000− | 69.2 | 13840− |
| STX_1 | 1.294 | — | <2.5 | — | 21.7 | — |
| STX_2 | 2.505 | — | 119.0 | — | 45.2 | — |
| STX_3 | 3.087 | — | 592.0 | — | 44.9 | — |
| STX_F | 1.479 | — | 512.0 | — | 24.6 | — |
| ECV_1 | 0.921 | — | <2.5 | — | 16.5 | — |
| ECV_2 | 1.867 | — | 33.0 | — | 31.4 | — |
| ECV_3 | 2.610 | — | 221.0 | — | 42.3 | — |
| ECV_4 | 2.862 | — | 280.0 | — | 42.8 | — |
| ECV_5 | 2.731 | — | 273.0 | — | 41.9 | — |
| ECV_6 | 3.526 | — | 784.0 | — | 45.2 | — |
| ECV_P | 2.404 | 485 | 295.0 | 59531 | 38.3 | 7729 |

TABLE 2-continued

YIELD CHARACTERISTICS

| Sample Code | Description |
| --- | --- |
| Load | Supernatant at 3 day after transfection (Time of harvest) |
| STX_1 | After depth filtration of 1/6 of the harvest |
| STX_2 | After depth filtration of 1/2 of the harvest |
| STX_3 | After depth filtration of 5/6 of the harvest |
| STX_F | After flushing depth filter with TBS buffer |
| ECV_1 | After 0.2 μm filtration of 1/12 of the harvest |
| ECV_2 | After 0.2 μm filtration of 1/4 of the harvest |
| ECV_3 | After 0.2 μm filtration of 5/12 of the harvest |
| ECV_4 | After 0.2 μm filtration of 7/12 of the harvest |
| ECV_5 | After 0.2 μm filtration of 3/4 of the harvest |
| ECV_6 | After 0.2 μm filtration of 11/12 of the harvest |
| ECV_P | Pool of harvest and flush |

As shown above in Table 2, over 70% of the protein and more than 62% of the HEK DNA found in the cell suspension prior to filtration was removed via this filtration step. The amount of AAV Inverted Terminal Repeat (ITR) nucleic acid in the pooled fraction containing the harvest and the filter flush (P) as measured by quantitative PCR (qPCR) was about half of that found in the cell suspension prior to filtration. Also, as measured by ELISA, greater than 65% of the AAV of the pre-filtration cell suspension was retained upon filtration.

Example 3

The following example describes an exemplary way of concentrating and conditioning a harvest via an ultrafiltration/diafiltration (UF/DF) tangential flow filtration (TFF) system.

Figure 7:
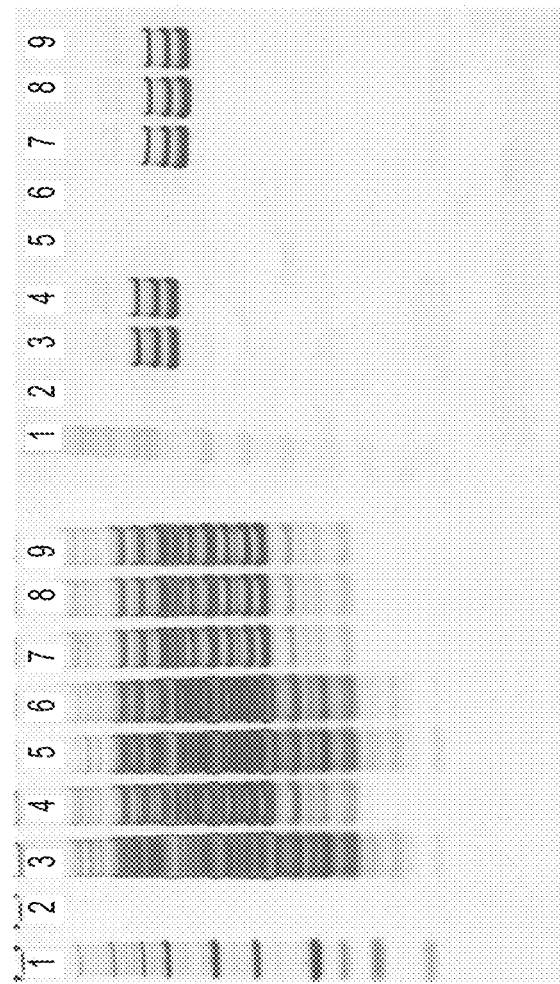
FIG. 7 is a silver stain (left) and a western blot (right) of the fractions indicated.

The harvest obtained in Example 2 was subjected to an UF/DF TFF system to concentrate and condition the harvest. In a first step, the harvest was concentrated approximately 16-fold to a target volume of 12 L by TFF using 3×0.5 m² Pall T-series Omega Centramate membranes 100 kDa (Part No.: OS100T06). The concentrated harvest was then subjected to two diafiltration steps to reduce media components and to condition the concentrated harvest to a pH of 8.5 and a conductivity of 15 mS/cm. The first diafiltration step was performed via a 5-fold volume exchange with Diafiltration Buffer 1 (DB1: 50 mM TRIS/500 mM NaCl/pH 8.5±0.2 at 25° C.). The second diafiltration step was conducted via a 5-fold volume exchange with Diafiltration Buffer 2 (DB2: 50 mM TRIS/125 mM NaCl/pH 8.5±0.2 at 25° C.). Each diafiltration step was carried out by using 3×0.5 m² Pall T-series Omega Centramate membranes 100 kDa (Part No.: OS100T06). After the second diafiltration step, the retentate was concentrated to a final target volume of 10 L by TFF as described above. The 10 L of concentrate was then filtered through a 0.2 μm filter element (5 inch, Pall ECV filter, Part No.: NP5LUECVP1S). In order to increase AAV8 yield, the UF/DF membranes, the UF/DF system and the 0.2 μm filter were flushed with approximately 2 L of DB2. The retentate and the filter flush were collected and mixed in a bag in order to prepare it for the subsequent capture step. FIG. 7 shows the intermediate steps of the TFF in silver stain (left) and Western blot (right). Parameters of the UF/DF TFF steps and characterization of the resulting conditioned concentrate [post UF/DF TFF steps] are found in Tables 3 and 4, respectively.

Description of Silver Stain
  NuPAGE 4-12% Bis-Tris Midi Gel 1.0 mm. 20 well
    Cat.Nr. WG1402BX10
  MES SDS Running Buffer. Invitrogen. Cat.Nr. NP0002
  SB+DTT Incubation 10 min bei 70° C.10 min cool down
    JAA treatment
Description of Western Blot
  NuPAGE 4-12% Bis-Tris Midi Gel 1.0 mm. 20 well
    Cat.Nr. WG1402BX10
  MES SDS Running Buffer. Invitrogen. Cat.Nr. NP0002
  SB+DTT Incubation 10 min bei 70° C.10 min cool down
    JAA treatment
  1st Antibody: Mab to VP1. VP2 and VP3 of AAV (Adeno-Associated Virus)
  Protein A affinity chromatography
  PROGEN61058
  2nd Antibody: GOAT anti Mouse ALP
  SIGMA A4656 1:2000 1 h

TABLE 3

| Step | Buffer | Volume | Pressure [bar] Feed | Pressure [bar] Retentate | Pressure [bar] Filtrate | TMP (transmembrane pressure) | Flux [l/h] Retentate | Flux [l/h] Filtrate | Conductivity [mS/cm] |
| --- | --- | --- | --- | --- | --- | --- | --- | --- | --- |
| Conditioning and Equilibration | Ultradiafiltration buffer | approx. 12 L | 0.7-1.1 | 0.0-0.3 | 0.0-0.2 | 0.20-0.40 | n.a. | n.a. | n.a. |
| Ultrafiltration (1st Concentration) | n.a. | to 12 L | 1.4-1.8 | 0.9-1.4 | 0.1-0.6 | 1.00-1.09 | 240-420 | 110-260 | 11.75 |
| 1st Ultradiafiltration | Ultradiafiltration buffer | 5 Volume changes | 1.4-1.5 | 0.8-1.0 | 0.1-0.2 | 1.00-1.06 | 401-425 | 92-118 | 48.1 |
| 2nd Ultradiafiltration | Ultradiafiltration buffer | 5 Volume changes | 1.4 | 0.8 | 0.1 | 0.99-1.02 | 439-447 | 82-94 | 15.57 |

TABLE 3-continued

| Step | Buffer | Volume | Pressure [bar] Feed | Pressure [bar] Retentate | Pressure [bar] Filtrate | TMP (transmembrane pressure) | Flux [l/h] Retentate | Flux [l/h] Filtrate | Conductivity [mS/cm] |
|---|---|---|---|---|---|---|---|---|---|
| Ultrafiltration (2nd Concentration) | n.a. | to 10 L | 1.4 | 0.8 | 0.1 | 0.99-1.02 | n.a. | n.a. | n.a. |
| Membrane flush | Ultradiafiltration buffer | ~2 L | 1.0 | n.a. | n.a. | n.a. | n.a. | n.a. | n.a. | n.a. . . . not applicable

TABLE 4

| Sample code: | Volume [ml] | Protein by Bradford [µg/ml] | Protein by Bradford Total [mg] | Protein by Bradford Yield (%) | ITR-qPCR [vg/ml] | ITR-qPCR Total (vg) | ITR-qPCR Yield (%) | AAV ELISA [µg/ml] | AAV ELISA Total [mg] | AAV ELISA Yield (%) | HEK293 HCP ELISA [µg/ml] | HEK293 HCP ELISA Total [mg] | HEK293 HCP ELISA Yield (%) |
|---|---|---|---|---|---|---|---|---|---|---|---|---|---|
| Load | 201800 | 149.9 | 30247.8 | 100.0 | 4.12E+11 | 8.31E+16 | 100.0 | 2.2 | 449.2 | 100.0 | 39.4 | 7950.9 | 100.0 |
| Retentate | 12000 | 1672.3 | 20067.0 | 66.3 | 5.64E+12 | 6.77E+16 | 81.4 | 34.3 | 411.4 | 91.6 | 368.0 | 4416.0 | 55.5 |
| Filtrate | 189800 | 47.5 | 9017.4 | 31.7 | 7.97E+08 | 1.51E+14 | 0.2 | <0.03125 | — | — | n.d. | — | — |
| Diaretentate 1 | 12000 | 1433.7 | 17203.8 | 56.9 | 5.25E+12 | 6.30E+16 | 75.8 | 35.1 | 420.8 | 93.7 | 271.0 | 3252.0 | 40.9 |
| Diafiltrate 1 | 60000 | 31.0 | 1857 | 6 | 6.18E+08 | 3.71E+13 | 0.0 | <0.03125 | — | — | n.d. | — | — |
| Diaretentate 2 | 12000 | 1621.4 | 19456.4 | 64.3 | 5.20E+12 | 6.24E+16 | 75.1 | 42.8 | 513.3 | 114.3 | 284.0 | 3408.0 | 42.9 |
| Diafiltrate 2 | 60000 | 13.4 | 802 | 3 | 8.88E+08 | 5.33E+13 | 0.1 | <0.03125 | — | — | n.d. | — | — |
| Retentate (2 × diafiltrated) pooled with flush Post 0.2 µm filtration | 11857 | 1202.0 | 14252.6 | 47.1 | 4.81E+12 | 5.70E+16 | 68.6 | 28.0 | 332.5 | 74.0 | 227.0 | 2691.5 | 33.9 | n.d. . . . not determined

As shown in Table 4, the volume of the resulting conditioned concentrate was about 6% of the initial volume, yet the percentage of AAV in the concentrate was 74%, as measured by ELISA.

Example 4

This example demonstrates an exemplary method of negative chromatography with an anion exchanger.

Figure 5:
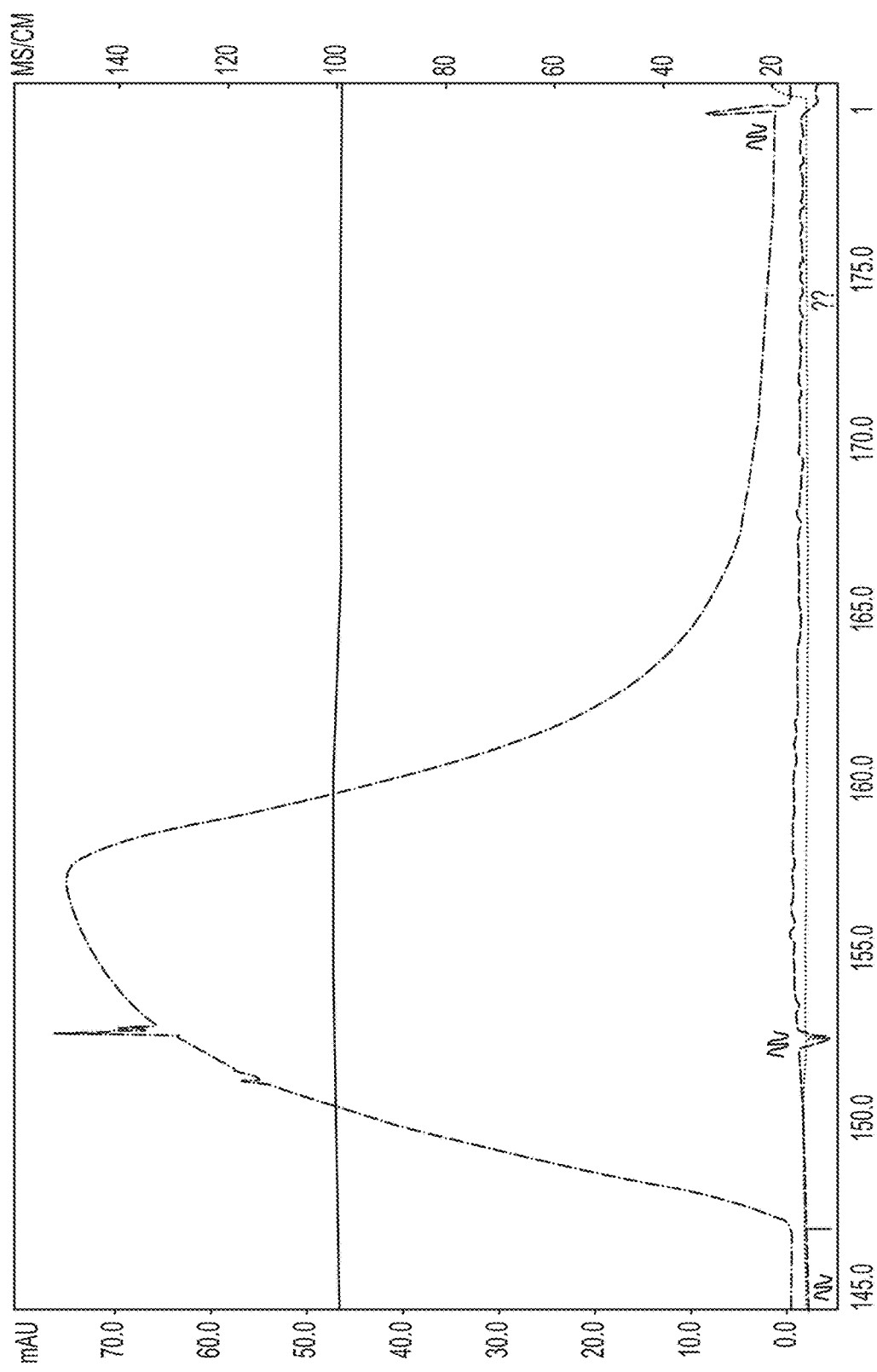
FIG. 5 is a graph of the flow through product of an AEX Mustang Q chromatography in negative (non-binding) mode.

After concentration and diafiltration of the harvest by TFF as described in Example 3, the AAV containing buffer is conditioned to 125 mM NaCl/50 mM TrisHCl/pH 8.5 for negative chromatography using a Mustang anion exchanger membrane (Pall Part Number XT5000MSTGQP1). At this condition, the AAV does not bind onto the anion exchanger membrane and, instead, flows through the column. After loading the column, two total volumes (equal to 2× the membrane capsule) of a flush buffer (125 mM NaCl/50 mM Tris HCl; pH 8.5) were used to flush any amount of nonbinding AAV8 out of the column. FIG. 5 provides the chromatogram of the flow through product of an AEX Mustang Q chromatography in negative (non-binding) mode. An elution was carried out to examine the bound proteins. Table 5 details the scheme of the negative chromatography step and Table 6 details the yield.

TABLE 5

| Step | Buffer | Inlet | Flowrate | CV | Col. Pos. | Outlet | Fraction |
|---|---|---|---|---|---|---|---|
| Equilibration 1 0.5M NaOH | 0.5M NaOH | B2 | 400 ml/min | 5 | 1 down 2 Bypass | F1 | Waste |
| Equilibration 2 2M NaOH | TWA-Buffer | A4 | 400 ml/min | 5 | 1 down 2 Bypass | F1 | Waste |
| Equilibration 3 | Equilibration buffer | A1 | 400 ml/min | 4 | 1 down 2 Bypass | F1 | Waste |
| Load with air sensor | Sample-Load: | S1 | 400 ml/min | — | 1 down 2 Bypass | 0-0.59CV F1 Ab0.59 CV F2 | Waste FT |
| Wash | Equilibration buffer | A1 | 400 ml/min | 3 | 1 down 2 Bypass | 0-1.68CV F2 1.68-3CV F1 | FT Waste |
| Elution | Elution buffer | B1 | 400 ml/min | 2.6 | 1 down 2 Bypass | 0-0.4CV F1 0.4-2.6CV F3 | Waste E |

Equilibration buffer: 50 mM Tris; 125 mM NaCl (pH 8.5 ± 0.1 bei 25° C.

Elution buffer: 20 mM Tris; 1000 mM NaCl (pH 9.0 ± 0.1 bei 25° C.

TABLE 6

| Code | Volume (S) | ITR qPCR vg/ml | Vg | % | AAV8 ELISA µg/ml | µg | % | AKT vg/µg |
|---|---|---|---|---|---|---|---|---|
| L | 11628.40 | 2.91E+12 | 3.38E+16 | 100 | 34.361 | 399563.45 | 100 | 8.47E+10 |
| FT | 22054.20 | 7.45E+11 | 1.64E+16 | 48.56 | 11.782 | 259842.58 | 65.03 | 6.32E+10 |
| E | 21009.20 | 8.31E+10 | 1.75E+15 | 5.16 | 1.055 | 22164.71 | 5.55 | 7.88E+10 |

| Code | In vitro biopotency | Protein by Bradford OR-1300443 µg/ml | mg | % | HEK293 HCP ELISA µg/ml | mg | % |
|---|---|---|---|---|---|---|---|
| L | 1.54 | 1295.98 | 15070.17 | 100.00 | 269 | 3128.04 | 100.00 |
| FT | 1.64 | 234.55 | 5172.81 | 34.32 | 107 | 2359.80 | 75.44 |
| E | — | 108.04 | 2269.83 | 15.06 | — | — | — |

L = Loaded fraction; FT = flow through fraction; E = eluted fraction

Figure 6:
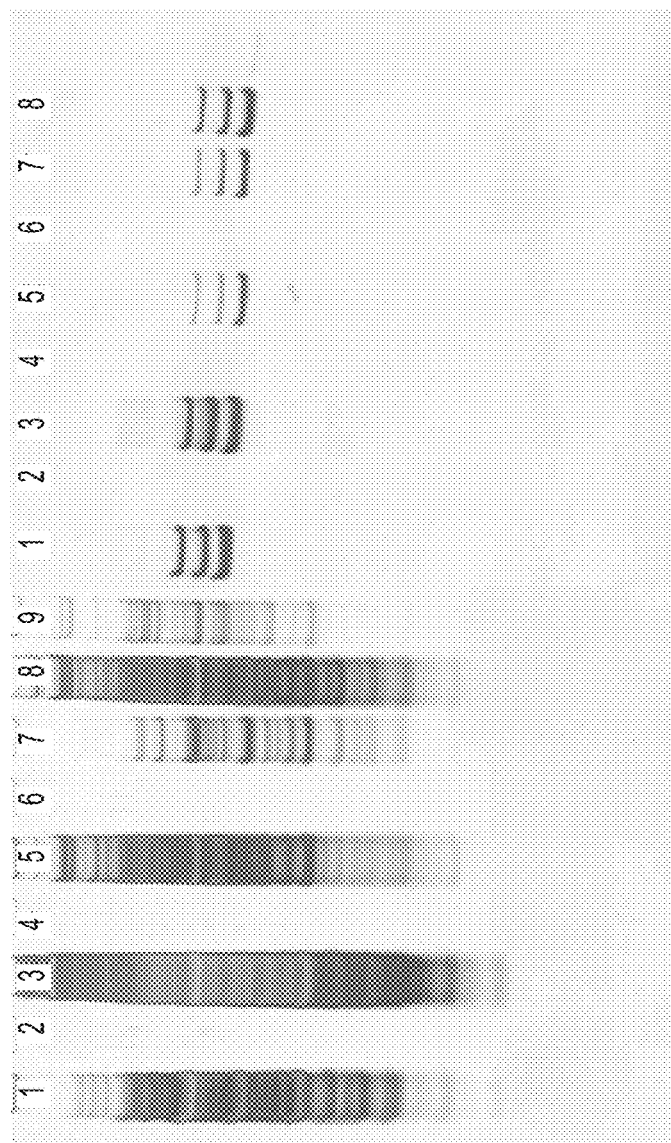
FIG. 6 is a silver stain (left) and a western blot (right) of the fractions indicated.

As shown in Table 6, the negative chromatography step successfully removed a substantial amount of total protein while retaining a significant amount of AAV. This increase of purity is also illustrated by the silver stain and Western blot in FIG. 6. The flow through fraction comprised about 65% of the initial amount of AAV, whereas less than 6% of the AAV was present in the eluted fraction. Also, the total protein amount of the flow-through fraction was significantly reduced. Only about 34% of total protein remained in the FT fraction.

Description of Silver Stain
NuPAGE 4-12% Bis-Tris Midi Gel 1.0 mm. 20 well Cat.Nr. WG1402BX10
MES SDS Running Buffer. Invitrogen. Cat.Nr. NP0002
SB+DTT Incubation 10 min bei 70° C.10 min cool down JAA treatment Description of Western Blot
NuPAGE 4-12% Bis-Tris Midi Gel 1.0 mm. 20 well Cat.Nr. WG1402BX10
MES SDS Running Buffer. Invitrogen. Cat.Nr. NP0002
SB+DTT Incubation 10 min bei 70° C.10 min cool down JAA treatment
1st Antibody: Mab to VP1. VP2 and VP3 of AAV (Adeno-Associated Virus)
Protein A affinity chromatography
PROGEN61058
$2^{nd}$ Antibody: GOAT anti Mouse ALP
SIGMA A4656 1:2000 1 h Example 5

This example demonstrates an exemplary method of a second TFF step.

The AAV8-containing flow through (FT) fraction obtained through negative chromatography (Example 4) was concentrated and diafiltered against a diafiltration buffer (DB1) comprising 500 mM NaCl/50 mM TrisHCl; pH 8.5 to condition the product for the following ultracentrifugation (UC) step (e.g., Example 6, 7, 9, 14, or 16). The second TFF step (TFF2) was carried out using 4×0.1 m² Pall T-Series Omega Centramate Membranes 100 kDa (4× Pall. Part No.: 05100T12) and the Pall UF/DF System CM500. After ultracentrifugation/diafiltration, the product was concentrated to a target volume of 1200 ml and drained from the system. In order to increase AAV8 yield the membrane and the UF/DF system were subsequently flushed with approx. 400 ml diafiltration buffer (10 min. recirculation on retentate side at 1 bar Feed pressure). The membrane flush and the concentrated product were pooled and filtered using 0.2 µm Filter (PALL Part No.: KA02EAVP2S) for bioburden reduction. Table 7 details the scheme of TFF2 and Table 8 details the yield of this step.

TABLE 7

| Step | Buffer | Volume | Pressure [bar] Feed | Retentate | Filtrate | TMP (transmembrane pressure) | Flux [l/h] Retentate | Filtrate | Conductivity [mS/cm] |
|---|---|---|---|---|---|---|---|---|---|
| Conditioning and Equilibration | Diafiltration buffer | approx. 2000 ml | 0.5-1.2 | 0.0-0.1 | 0.0 | 0.25-0.65 | n.a. | n.a. | n.a. |
| Ultrafiltration (Concentration) | n.a. | to 1600 ml | 1.6 | 0.1 | 0.0 | 0.85 | 188.4-190.8 | 61.0-77.5 | 14.84 |
| Diafiltration | Diafiltration buffer | 4-5 Volume changes | 1.5-1.6 | 0.1 | 0.0 | 0.80-0.85 | 184.2-186.0 | 61.3-63.8 | 46.92 |
| Ultrafiltration ($2^{nd}$ Concentration) | n.a. | to 1200 ml | 0.5-1.6 | n.a. | n.a. | n.a. | n.a. | n.a. | n.a. |
| Membrane flush | Diafiltration buffer | ~400 ml | 1.0 | n.a. | n.a. | n.a. | n.a. | n.a. | n.a. |

Diafiltration buffer = 50 mM Tris/500 mM NaCl, pH 8.5 ± 0.2 bei 25° C.

TABLE 8

| Step | Volume* [ml] | protein by Bradford OR-1300448 (µg/ml) | protein by Bradford (mg) | protein by Bradford Yield (%) | ITR qPCR (vg/ml) | ITR qPCR (vg) | ITR qPCR Yield (%) |
| --- | --- | --- | --- | --- | --- | --- | --- |
| Load | 22037.4 | 247 | 5437 | 100 | 4.61.E+11 | 1.02.E+16 | 100.00 |
| Retentate | 1600.0 | 1078 | 1725 | 32 | 5.88.E+12 | 9.41.E+15 | 92.61 |
| Filtrate | 20301.5 | 171 | 3480 | 64 | 7.73.E+08 | 1.57.E+13 | 0.15 |
| Diafiltrate | 7716.5 | 129 | 992 | 18 | 6.41.E+08 | 4.95.E+12 | 0.05 |
| Retentate (diafiltrated) | 1600.0 | 523 | 837 | 15 | 6.32.E+12 | 1.01.E+16 | 99.53 |
| Retentate (diafiltrated) pooled with flush Prior 0.2 µm filtration | 1671.4 | 523 | 875 | 16 | 6.32.E+12 | 1.06.E+16 | 103.98 |
| Retentate (diafiltrated) pooled with flush Post 0.2 µm filtration | 1686.0 | 534 | 901 | 17 | 6.76.E+12 | 1.14.E+16 | 112.19 |

| Step | AAV ELISA (µg/ml) | AAV ELISA total (mg) | AAV ELISA Yield (%) | HEK293 HCP ELISA (µg/ml) | HEK293 HCP ELISA Total (mg) | HEK293 HCP ELISA Yield (%) |
| --- | --- | --- | --- | --- | --- | --- |
| Load | 16.64 | 366.81 | 100 | 122 | 2689 | 100 |
| Retentate | 194.27 | 310.84 | 85 | 356 | 570 | 21 |
| Filtrate | <0.03125 | — | — | — | — | — |
| Diafiltrate | <0.03125 | — | — | — | — | — |
| Retentate (diafiltrated) | 187.07 | 299.31 | 82 | 101 | 162 | 6 |
| Retentate (diafiltrated) pooled with flush Prior 0.2 µm filtration | 174.57 | 291.78 | 80 | — | — | — |
| Retentate (diafiltrated) pooled with flush Post 0.2 µm filtration | 192.53 | 324.61 | 88 | 104 | 175 | 7 |

As shown in Table 8, the TFF2 step successfully reduced the volume to about 7.5% of the original volume (load volume) while retaining 88% of the initial AAV.

Example 6

This example demonstrates an exemplary method of separating empty from full AAV particles through ultracentrifugation using 50% (w/w) buffered ethylene glycol solution and 50% (w/w) sucrose gradient. This step additionally removes host cell proteins (e.g., HSP70). Product related impurities like "empty capsids" and host cell proteins such as HSP70 and LDH, also are eliminated via this step.

A 50% (w/w) ethylene glycol buffered solution in 50 mM TrisHCl/750 mM NaCl at pH 8.0 containing the AAV8 sample comprising vector DNA of human coagulation Factor IX Padua in a single stranded self-complementary form (2.6 kb), was loaded into the ultracentrifuge (UC) followed by two different sucrose solutions which vary in sucrose concentration. The sucrose solution loaded into the UC first had a 55% sucrose concentration. The sucrose solution loaded into the UC immediately after the first sucrose solution had a 60% sucrose concentration. The ratio of loaded sample to sucrose gradient is 1:1 and sucrose solutions were of equal volumes. The total core volume is 1,600 ml.

One kilogram of the buffered sucrose solution with a 55% sucrose concentration was prepared by mixing 2.42 g of Tris(hydroxymethyl)aminomethane (Trometamol) with 8.00 g sodium chloride and 550.00 g sucrose. WFI was added to near 1 kg, with 1 M NaOH and 25% HCl used to adjust the pH as needed. WFI was then added to 1 kg.

One kilogram of the buffered sucrose solution with a 60% sucrose concentration was prepared by mixing 2.42 g of Tris(hydroxymethyl)aminomethane (Trometamol) with 8.00 g sodium chloride and 600.00 g sucrose. WFI was added to near 1 kg, with 1 M NaOH and 25% HCl used to adjust the pH as needed. WFI was then added to 1 kg.

A density gradient forms during a first UC phase wherein rotational speed was set at 4,000 rpm and the temperature was maintained at 2-10° C. After the first phase, the rotational speed was increased to 35,000 rpm and the temperature was increased to 22° C. During this second phase at higher speed and temperature, full AAV particles were separated from the empty capsids. After 20 hours, the ultracentrifuge was stopped and the fractions containing the majority of full AAV particles were collected. Additional details relating to the UC step that was performed, including details about input parameters for building up the gradient, collecting the fraction containing the full particles, elution rate, etc., are provided below in Table 9.

TABLE 9

| Process Stage | Parameter/Material | Value |
|---|---|---|
| General | Equipment | CC40 |
| | Fermentation equivalent | 1/2 of 500 L |
| | core volume | 3.2 L |
| Loading | Loading sequence | AAV8 containing buffered ethylene glycol solution -> 55% Suc. -> 60% Suc. |
| | Volume of UFB-intermediate per one run | 1.6 L |
| | Feed Flowrate UFB-intermediate | 11.5 L/h |
| | Feed Flowrate Sucrose solutions | 4.8 L/h |
| | Volume of 55% Sucrose | Approx. 800 mL |
| | Volume of 60% Sucrose | Approx. 800 mL |
| | Concentration of Sucrose 55% Sucrose | 55% ± 1% |
| | Concentration of Sucrose 60% Sucrose | 60% ± 1% |
| | pH of sucrose buffers (55%. 60%) | 7.4 +/- 0.3 |
| Gradient build up | Rotation speed: Increase from | 0 rpm-4000 rpm |
| | Time for gradient build up | 17-25 min |
| | Chamber temperature during gradient build up | 2-10° C. |
| Acceleration | Rotation speed: Increase from | 4000-35000 rpm |
| | Time for acceleration | 5-60 min |
| | Chamber temperature during acceleration | 2-10° C. |
| Separation | Rotation speed | 35000 ± 2000 rpm |
| | Chamber Temperature during separation | Target: 22 +/- 2° C. |
| | Duration separation | 20 hours (can run 16-20 hours) |
| Deceleration | Rotation speed: Decrease from | 35000-4000 rpm |
| | Time for deceleration | 5-90 min |
| | Chamber temperature during deceleration | 2-10° C. |
| Fading out | Rotation speed: Decrease from | 4000-0 rpm |
| | Time for fading out | 15-30 min |
| | Chamber temperature during fading out | 2-10° C. |
| Fractionation | Elution flowrate | 6 L/h |
| | Mass of fraction | 100-600 g |
| | Mass of peak pool (per Fermentation batch) | 200-1800 g |
| | Holding time after UC - Temperature | 2-8° C. |

| Buffer | pH & Conductivity | Composition |
|---|---|---|
| 55% sucrose solution | pH 7.4 ± 0.2 at 25° C. | 20 mM Tris. 8 g/kg NaCl 55% sucrose |
| 60% sucrose solution | pH 7.4 ± 0.2 at 25° C. | 20 mM Tris. 8 g/kg NaCl 60% sucrose |

Figure 17:
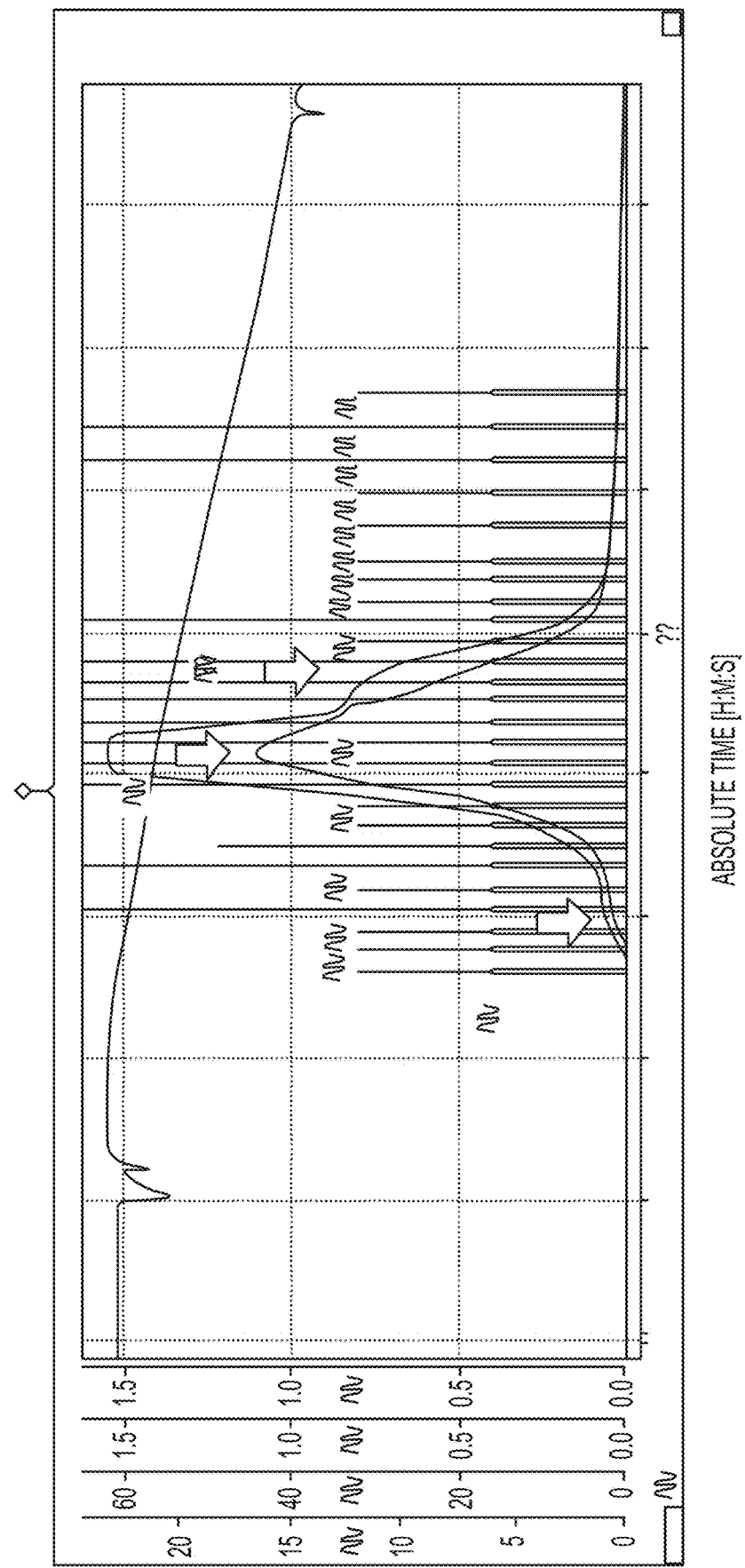
FIG. 17 is a graph of the ultracentrifugation elution profile in which AAV8 in a 50% (w/w) ethylene glycol buffered solution in Tris/NaCl is ultracentrifuged for 20 hours at 35,000 rpm in using a sucrose gradient with 55% and 60% sucrose solutions. The ratio of AAV8 loading sample to the sucrose gradient is 1:1. The vector DNA is human coagulation Factor IX Padua, single stranded self-complementary, full length (2.6 kB).

The results are shown in FIG. 17, in which empty capsids (at fraction 15) are resolved from the full capsids (at fraction 11).

Figure 18:
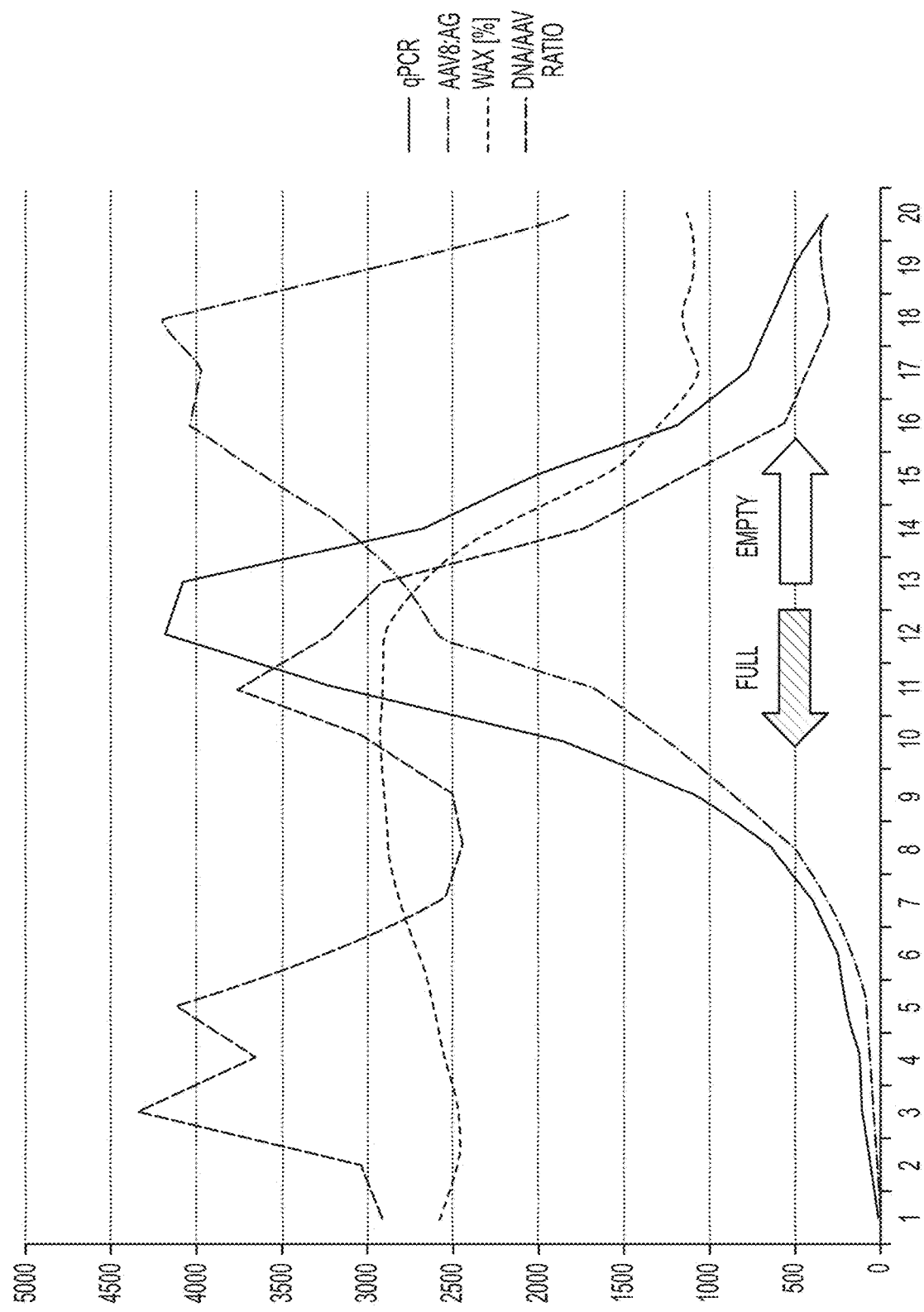
FIG. 18 is a graph of a separation of AAV8 containing single stranded vector DNA of human coagulation Factor IX Padua (2.6 kB) using ultracentrifugation with the 55-60% sugar layer protocol, where in the AAV8 sample is loaded in a 50% (w/w) ethylene glycol buffered solution in Tris/NaCl. Each Fraction is tested via: AAV8 ITR qPCR, AAV8 Antigen, WAX (Weak anion exchanger—full capsids), DNA/AAV ratio is a ratio of ITR qPCR vector genomes (vg/ml)/AAV8 capsid antigen ELISA (cp/ml). The data was normalized to allow the graphs to be presented on the same axes.

FIG. 18 shows the results of undertaking four different assays on each of the fractions shown in FIG. 17. qPCR refers to quantitative PCR of ITR of AAV8 (ITR-qPCR). AAV8:AG refers to ELISA against an AAV8 antigen. WAX % refers to the percentage of full capsids as quantified by weak anion exchange. DNA/AAV ratio (sometimes referred to as Spec. Act. or specific activity herein), refers to the ratio of total vector genomes (ITR-qPCR) to the total amount of rAAV8 particles (AAV8:AG), which gives an indication as to the proportion of DNA-containing capsids as well as full capsids. A higher DNA/AAV ratio is correlated with a higher amount of full capsids. The transition from full to empty capsids is seen by the abrupt decline in Spec. Act. from fraction 13 to fraction 15. The values for each assay were normalized to one another, as indicated by the Y axis.

TABLE 10

| Fraction Nr.: | Blue 06 qPCR vg/ml | AAV8:AG cp/ml | WAX [%] Full AAV8 | DNA/AAV Ratio vg/cp |
|---|---|---|---|---|
| 1 | 2.61E+11 | 8.9E+11 | 86 | 2.93E+10 |
| 2 | 6.05E+11 | 1.99E+12 | 82 | 3.04E+10 |
| 3 | 1.08E+12 | 2.47E+12 | 82 | 4.37E+10 |
| 4 | 1.21E+12 | 3.32E+12 | 85 | 3.64E+10 |
| 5 | 2.04E+12 | 4.94E+12 | 87 | 4.13E+10 |
| 6 | 2.51E+12 | 7.85E+12 | 90 | 3.20E+10 |
| 7 | 4E+12 | 1.57E+13 | 94 | 2.55E+10 |
| 8 | 6.41E+12 | 2.62E+13 | 96 | 2.45E+10 |
| 9 | 1.1E+13 | 4.4E+13 | 97 | 2.50E+10 |
| 10 | 1.86E+13 | 6.25E+13 | 98 | 2.98E+10 |
| 11 | 3.18E+13 | 8.4E+13 | 97 | 3.79E+10 |
| 12 | 4.19E+13 | 1.3E+14 | 97 | 3.22E+10 |
| 13 | 4.09E+13 | 1.395E+14 | 90 | 2.93E+10 |
| 14 | 2.69E+13 | 1.56E+14 | 76 | 1.72E+10 |
| 15 | 2.05E+13 | 1.79E+14 | 54 | 1.15E+10 |

TABLE 10-continued

| Fraction Nr.: | Blue 06 qPCR vg/ml | AAV8:AG cp/ml | WAX [%] Full AAV8 | DNA/AAV Ratio vg/cp |
|---|---|---|---|---|
| 16 | 1.18E+13 | 2.025E+14 | 42 | 5.83E+09 |
| 17 | 7.87E+12 | 1.985E+14 | 35 | 3.96E+09 |
| 18 | 6.28E+12 | 2.1E+14 | 39 | 2.99E+09 |
| 19 | 5.06E+12 | 1.43E+14 | 36 | 3.54E+09 |
| 20 | 3.1E+12 | 8.79E+13 | 38 | 3.53E+09 |

Example 7

This example demonstrates an exemplary method of separating empty from full AAV particles through ultracentrifugation using a sucrose gradient. This step additionally removed host cell proteins (e.g., HSP70). Product related impurities like "empty capsids" (as defined above) also were eliminated via this step.

The concentrated fraction containing vector DNA comprising single stranded DNA encoding B-Domain deleted human coagulation factor VIII obtained via TFF2 of Example 5 was loaded into the ultracentrifuge (UC) followed by three different sucrose solutions which vary in sucrose concentration. The sucrose solution loaded into the UC first had a 50% sucrose concentration. The sucrose solution loaded into the UC immediately after the first sucrose solution had a 55% sucrose concentration and the sucrose solution loaded into the UC last had a 60% sucrose concentration.

One kilogram of the buffered sucrose solution with a 50% sucrose concentration was prepared by mixing 2.42 g of Tris(hydroxymethyl)aminomethane (Trometamol) with 8.00 g sodium chloride and 500.00 g sucrose. WFI was added to near 1 kg, with 1 M NaOH and 25% HCl used to adjust the pH as needed. WFI was then added to 1 kg.

One kilogram of the buffered sucrose solution with a 55% sucrose concentration was prepared by mixing 2.42 g of Tris(hydroxymethyl)aminomethane (Trometamol) with 8.00 g sodium chloride and 550.00 g sucrose. WFI was added to near 1 kg, with 1 M NaOH and 25% HCl used to adjust the pH as needed. WFI was then added to 1 kg.

One kilogram of the buffered sucrose solution with a 60% sucrose concentration was prepared by mixing 2.42 g of Tris(hydroxymethyl)aminomethane (Trometamol) with 8.00 g sodium chloride and 600.00 g sucrose. WFI was added to near 1 kg, with 1 M NaOH and 25% HCl used to adjust the pH as needed. WFI was then added to 1 kg.

A density gradient formed during a first UC phase wherein rotational speed is set at 4000 rpm and the temperature was maintained at 2-10° C. After the first phase, the rotational speed was increased to 35000 rpm and the temperature increased to 22° C. During this second phase at higher speed and temperature, full AAV particles were separated from the empty capsids. After approximately 5 hours, the ultracentrifuge was stopped and the fractions containing the majority of full AAV particles were collected. Additional details relating to the UC step that was performed, including details about input parameters for building up the gradient, collecting the fraction containing the full particles, elution rate, etc., are provided below in Tables 11 and 12.

TABLE 11

| Process Stage | Parameter/Material | Value |
|---|---|---|
| General | Equipment | CC40S |
|  | Fermentation equivalent | 200 L |
|  | core volume | 3.2 L |
| Loading | Loading sequence | UFB-intermediate -> 50% Suc. -> 55% Suc. -> 60% Suc. |
|  | Volume of UFB-intermediate per one run | 1.6 L |
|  | Feed Flowrate UFB-intermediate | 6 L/h |
|  | Feed Flowrate Sucrose solutions | 1.5 L/h |
|  | Volume of 50% Sucrose | 400 ± 20 mL |
|  | Volume of 55% Sucrose | 200 ± 10 mL |
|  | Volume of 60% Sucrose | 200 ± 10 mL |
|  | Concentration of Sucrose 50% Sucrose | 50% ± 1% |
|  | Concentration of Sucrose 55% Sucrose | 55% ± 1% |
|  | Concentration of Sucrose 60% Sucrose | 60% ± 1% |
|  | pH of sucrose buffers (50%. 55%. 60%) | 7.4 +/- 0.3 |
| Gradient build up | Rotation speed: Increase from | 0 rpm-4000 rpm |
|  | Time for gradient build up | 17-25 min |
|  | Chamber temperature during gradient build up | 2-10° C. |
| Acceleration | Rotation speed: Increase from | 4.000-35.000 rpm |
|  | Time for acceleration | 5-60 min |
|  | Chamber temperature during acceleration | 2-10° C. |
| Separation | Rotation speed | 35.000 ± 2.000 rpm |
|  | Chamber Temperature during separation | Target: 22 +/- 2° C. |
|  | Duration separation | 300 ± 30 min |
| Deceleration | Rotation speed: Decrease from | 35.000-4.000 rpm |
|  | Time for deceleration | 5-90 min |
|  | Chamber temperature during deceleration | 2-10° C. |
| Fading out | Rotation speed: Decrease from | 4.000-0 rpm |
|  | Time for fading out | 15-30 min |
|  | Chamber temperature during fading out | 2-10° C. |
| Fractionation | Elution flowrate | 3 L/h |
|  | Volume of fraction | 25-50 mL |
|  | Volume of peak pool (per Fermentation batch) | 300-450 mL |

TABLE 11-continued

| | |
|---|---|
| Fraction start density Brix | 56.5-54 |
| Fraction start (UV 254) increase | >0.004 |
| Fraction end (UV 254) | after peak maximum of UV254 and no decrease of signal |
| Fraction end density Brix | 51 |
| Holding time after UC - Temperature | 2-8° C. |
| Holding time after UC - Time | max. 7 days |

| Buffer | pH & Conductivity | Composition |
|---|---|---|
| 50% sucrose solution | pH 7.4 ± 0.2 at 25° C. | 20 mM Tris. 8 g/kg NaCl 50% sucrose |
| 55% sucrose solution | pH 7.4 ± 0.2 at 25° C. | 20 mM Tris. 8 g/kg NaCl 55% sucrose |
| 60% sucrose solution | pH 7.4 ± 0.2 at 25° C. | 20 mM Tris. 8 g/kg NaCl 60% sucrose |

TABLE 12

| | | ITR qPCR | | | AAV ELISA | | | HEK293 HCP ELISA | | |
|---|---|---|---|---|---|---|---|---|---|---|
| Step | Volume [ml] | (vg/ml) | Total (vg) | Yield (%) | (µg/ml) | Total (mg) | Yield (%) | (µg/ml) | Total (mg) | Yield (%) |
| Load | 1600 | 7.8E+12 | 1.3E+16 | 100 | 206.4 | 330 | 100 | 95.9 | 153.44 | 100 |
| Forerun | 300 | — | — | — | 4.1 | 1 | 0 | — | — | — |
| Peak Pool | 250 | 1.6E+13 | 3.9E+15 | 31 | 83.7 | 21 | 6 | <0.5 | 0.125 | 0.08147 |
| Mostly empty capsids | 350 | — | — | — | 719.6 | 252 | 76 | — | — | — |
| Tail run | 2300 | — | — | — | 10.7 | 25 | 7 | — | — | — |

| | | HEK293 DNA PCR | | | In vitro | WAX |
|---|---|---|---|---|---|---|
| Step | Volume [ml] | (ng/ml) | Total (µg) | Yield (%) | Biopotency (BPU) | (Area % peak 2) |
| Load | 1600 | 5 | 8 | 100 | 0.65 | n.d. |
| Forerun | 300 | — | — | — | — | — |
| Peak Pool | 250 | 1.35 | 0.3375 | 0.10 | 1.25 | 82% |
| Mostly empty capsids | 350 | — | — | — | — | — |
| Tail run | 2300 | — | — | — | — | — |

Figure 9:
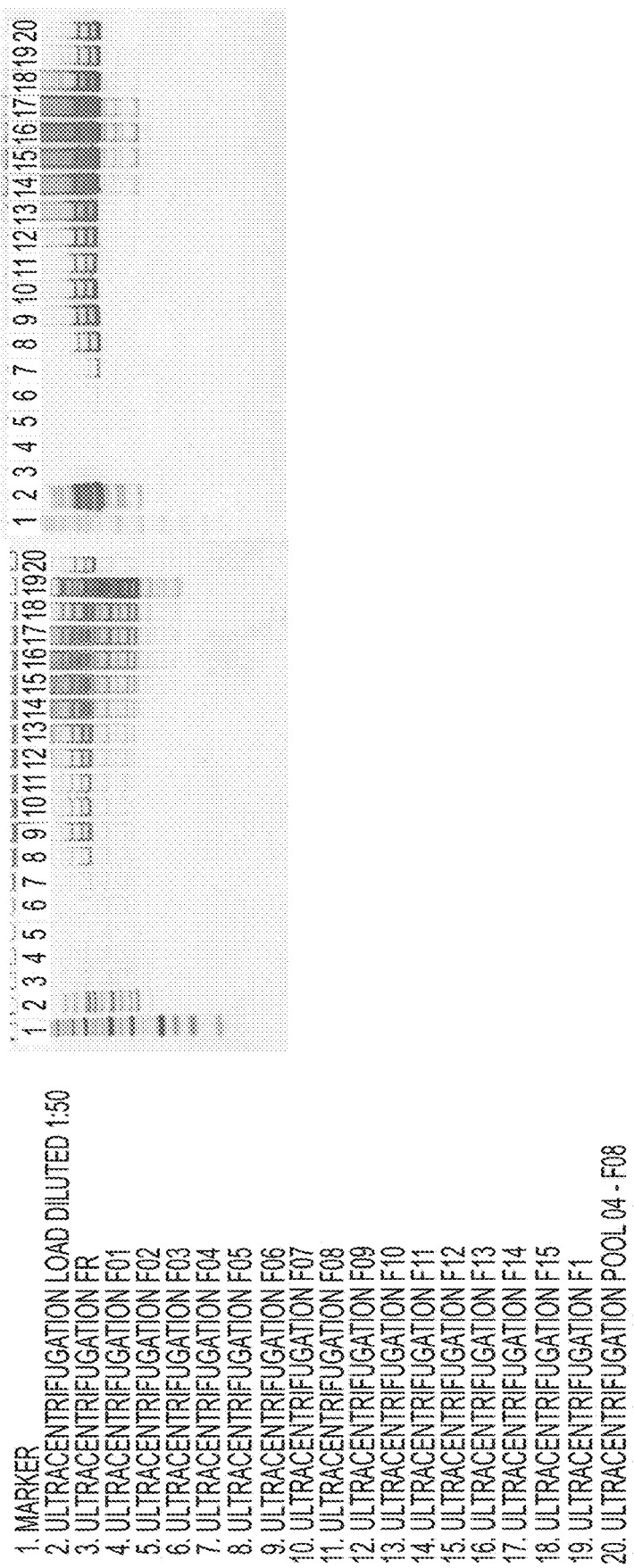
FIG. 9 is a silver stain (left) and a western blot (right) of the fractions indicated.

The elution pattern is presented in FIG. 8 and silver stain and western blots of the load and single fractions are presented in FIG. 9. As shown in Table 12, 82% of the particles in the peak pool are considered as full particles.
Description of Silver Stain
  NuPAGE 4-12% Bis-Tris Midi Gel 1.0 mm. 20 well Cat.Nr. WG1402BX10
  MES SDS Running Buffer. Invitrogen. Cat.Nr. NP0002
  SB+DTT Incubation 10 min at 70° C.10 min cool down JAA treatment
Description of Western Blot
  NuPAGE 4-12% Bis-Tris Midi Gel 1.0 mm. 20 well Cat.Nr. WG1402BX10
  MES SDS Running Buffer. Invitrogen. Cat.Nr. NP0002
  SB+DTT Incubation 10 min at 70° C.10 min cool down JAA treatment
  1$^{st}$ Antibody: Mab to VP1. VP2 and VP3 of AAV (Adeno-Associated Virus)
  Protein A affinity chromatography
  PROGEN61058
  2$^{nd}$ Antibody: GOAT anti Mouse ALP
  SIGMA A4656 1:2000 1 h Example 8

This example demonstrates an exemplary method of inactivating lipid enveloped viruses and a polish step.

Figure 10:
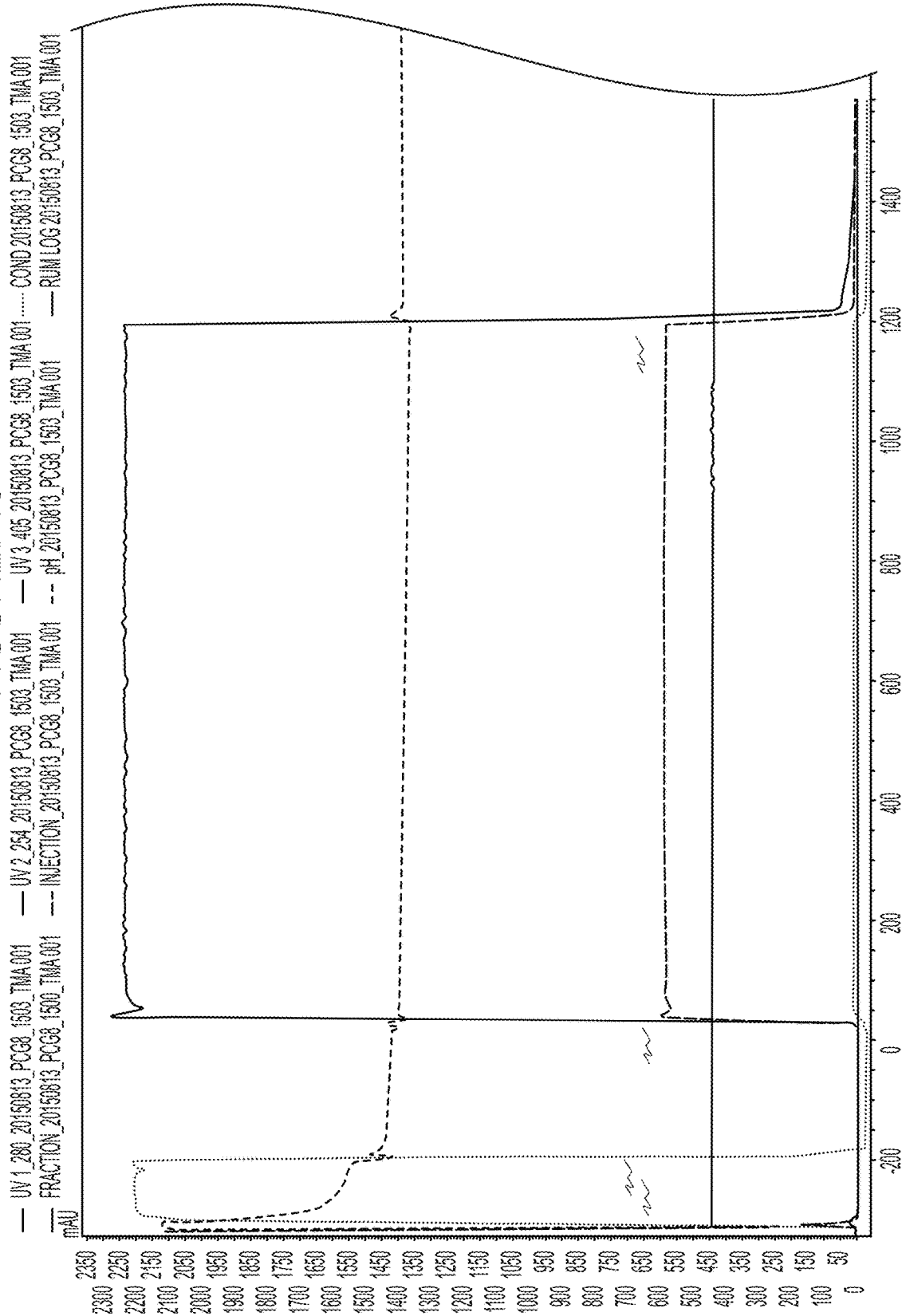
FIG. 10 is the final polishing of AAV8 on Fractogel TMAE.
Figure 10:
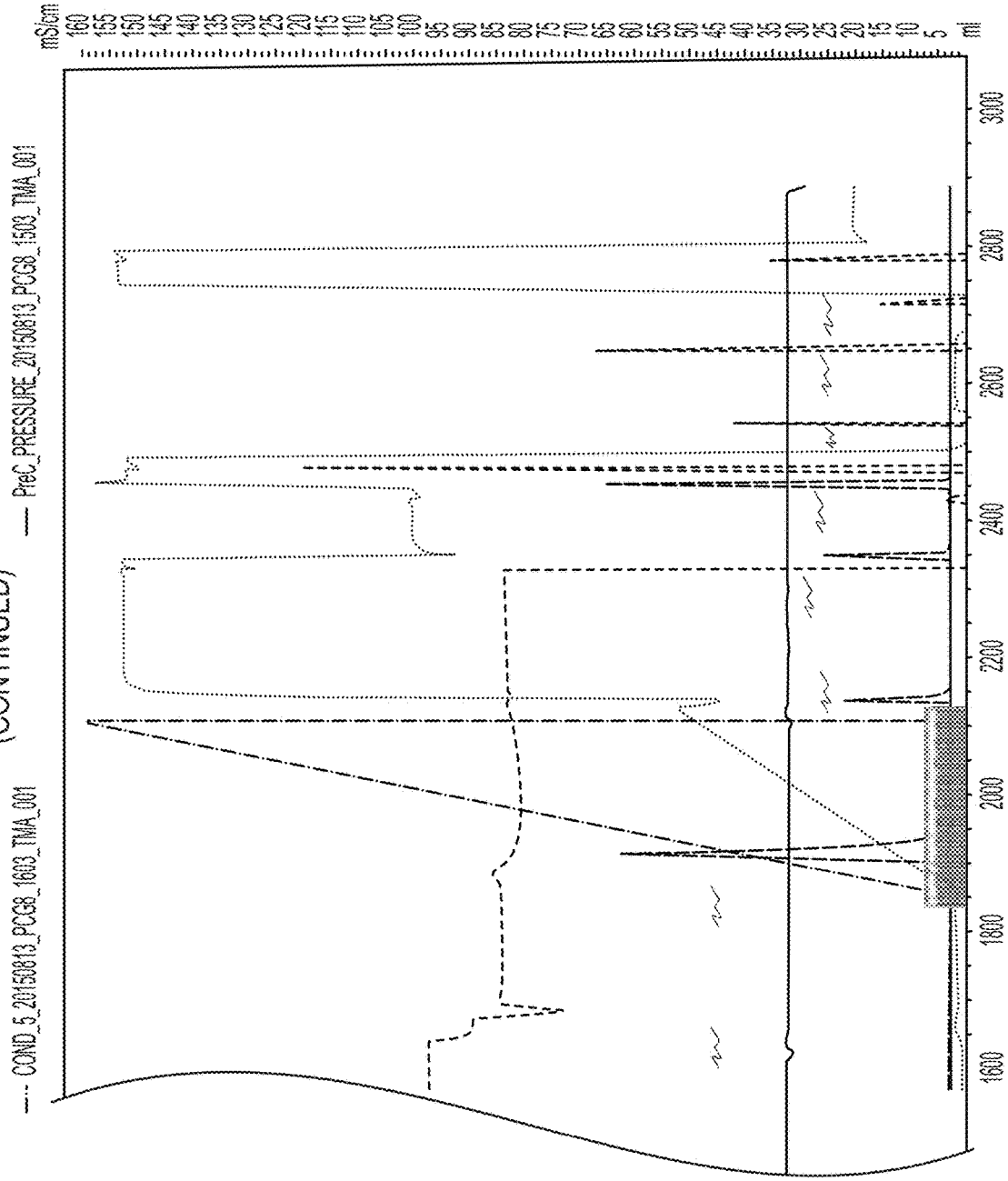

The AAV8-containing fractions obtained upon the UC step of Example 7 were pooled and diluted 1:2.5 with an equilibration buffer (50 mM Tris; pH 8.5±0.2). Treatment with a solvent detergent (0.3% Tri-n-butylphosphate; 1.0% Triton X100; 0.3% Polysorbate80) was performed. The conductivity of the solvent was subsequently adjusted to 3.6±0.2 mS/cm with a further 1:2 dilution. The resulting solution was loaded onto a chromatography column containing Fractogel® EMD TMAE (M) (Merck-Millipore Cat.: 116881) ID 22 mm bed height 57 mm (Merck-Millipore Vantage VL 22×250.Cat.Nr.: 96220250), and then washed with equilibration buffer (50 mM Tris pH 8.5±0.2). A second wash step was performed with a buffer (8.09 mM Na$_2$HPO$_4$; 1.47 mM KH$_2$PO$_4$; 2.68 mM KCl; 5% Sorbitol). The column elution was conducted by a NaCl gradient of 12 column volumes—from a first elution buffer comprising 8.09 mM Na$_2$HPO$_4$; 1.47 mM KH$_2$PO$_4$; 2.68 mM KCl; 5% Sorbitol to a last elution buffer comprising 8.09 mM Na$_2$HPO$_4$ 1.47 mM KH$_2$PO$_4$; 2.68 mM KCl; 5% Sorbitol+ 600 mM NaCl. The main amount of the AAV8 elutes as a distinct sharp peak and was collected as E2 (Eluate2) which represents the purified AAV8 product. The column was finally stripped with 2M sodium chloride followed by a regeneration procedure. Tables 13 and 14 detail these steps and the yield obtained after performing these steps. FIG. 10 is the final polishing of AAV8 on Fractogel TMAE.

TABLE 13

| Step | Buffer | Inlet | Flowrate | CV | Outlet | Fraction |
|---|---|---|---|---|---|---|
| Gel activation | TWA-buffer | A13 | 60 cm/h | 5 | F1 | Waste |
| Equilibration | T50EQ-buffer | A11 | | 10 | F1 | Waste |
| Sample load With air sensor | Sample-Load | A2 | | — | F3 | ABS |
| ReEquilibration | T50EQ-buffer | A11 | | 10 | F3 | ABS |
| Wash | Fractogel-equilibration buffer | A12 | | 10 | F4 | WASH |
| Elution: Gradient from A12 to B1 in 12CV | Fractogel-Equilibration buffer Elution buffer | A12 B1 | | 12 | F2 (Frac | diverse |
| Elution: | Elution buffer | B1 (100%) | | 3 | F2 (Frac) | diverse |

| BUFFER | |
|---|---|
| T50EQ-buffer | Equilibration buffer 50 mM Tris pH 8.5 ± 0.2 |
| Fractogel-Equilibration buffer | 20 mM Sodium phosphate/2.68 mM Potassium chloride/pH 8.0 ± 0.2 + 5% Sorbitol |
| Elution buffer | 15 mM Sodium phosphate/5 mM Potassium phosphate/2.68 mM Potassium chloride/600 mM NaCl/pH 7.4 ± 0.2 + 5% Sorbitol |

TABLE 14

YIELD

| | Volume | qPCR FVIII | | | AAV8 ELISA | | | DNA/AAV ratio |
|---|---|---|---|---|---|---|---|---|
| | (g) | vg/mL | vg | % | µg/mL | µg | % | vg/µg |
| L Dil | 611.91 | 3.25E+12 | 1.99E+15 | 100.00 | 17.542 | 10734.04 | 100.00 | 1.85E+11 |
| E | 32.86 | 4.59E+13 | 1.51E+15 | 75.84 | 273.857 | 8998.94 | 83.84 | 1.68E+11 |
| Bulk | 59.34 | 1.89E+13 | 1.12E+15 | 74.36 | 122.89 | 7292.29 | 81.04 | 1.54E+11 |

| | Volume | HEK293 HCP ELISA | | | HEK-DNA | DNA/AAV ratio |
|---|---|---|---|---|---|---|
| | (g) | µg/mL | µg | % | ng/mL | vg/µg |
| L Dil | 611.91 | <0.2 | <122.38 | — | — | <0.01 |
| E | 32.86 | — | — | — | — | — |
| Bulk | 59.34 | <0.1 | <5.93 | — | 2.8 | <0.01 |

L Dil: is the diluted pool from ultracentrifugation prior the SD treatment and the final dilution rate; E is the Eluate from the AEX column; Bulk is the 1:2 diluted Eluate from the AEX column. Bulk is the formulated product prior dilution to the final drug product(FDP)

Example 9

This example demonstrates an exemplary method of purifying AAV from unpurified fractions comprising an ultracentrifugation step during which a density gradient forms.

Figure 11:
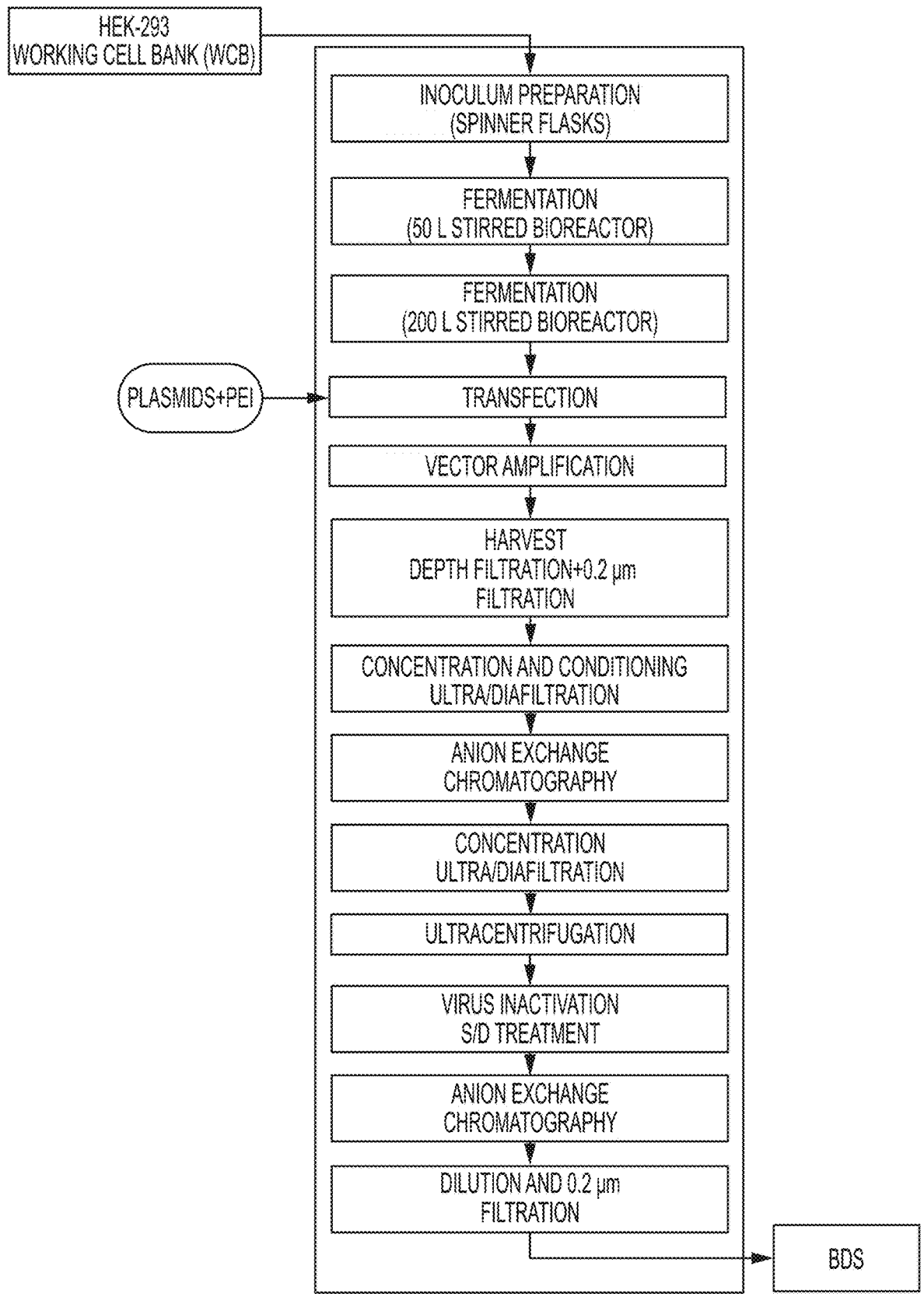
FIG. 11 is a schematic of an exemplary method of the present disclosure.

FIG. 11 is a schematic of the steps carried out in the exemplary method. The ultracentrifugation step was performed using a core with a capacity for 3.2 L volume (1.6 L product+1.6 L gradient/TBS buffer).

With the UC in standstill, the 1.6 L starting material (intermediate product from the previous process step=UFB) was loaded into the rotor with a constant flow rate of 6 L/h followed by the load of 3 sucrose solutions of varying density. The sucrose solutions were loaded with a constant flow rate of 1.5 L/h in the following order: 800 mL of 50% sucrose, 400 mL of 55% sucrose and 400 mL of 60% sucrose.

The filled rotor was accelerated from 0 up to 4000 rpm in order to achieve the zonal mode to build up a sucrose gradient with increasing density, followed by a second acceleration from 4000 up to 35000 rpm. The UC runs at 35000 rpm (approx. 90000 g-force) for 5 hours. Once the final speed was achieved, the temperature was shifted from +4° C. to +22° C. The AAV8 particles contained in the starting material moves into the sucrose gradient until they reach a point at which their density matches with the density of the surrounding gradient. As full and empty capsids differ in their density, this feature is used for the separation of full from empty virus capsids. One hour before the centrifugation step was finished, the temperature was manually shifted from +22° C. to +4° C. Stopping the UC from 35,000 to 0 rpm was performed in 2 steps: from 35,000 to 4,000 rpm by deceleration and from 4,000 rpm to 0 rpm by letting the rotor fade out.

The product was recovered with a flow rate of 6 L/h by collecting 25 mL fractions as well as a waste fraction at the end of the elution.

Figure 12:
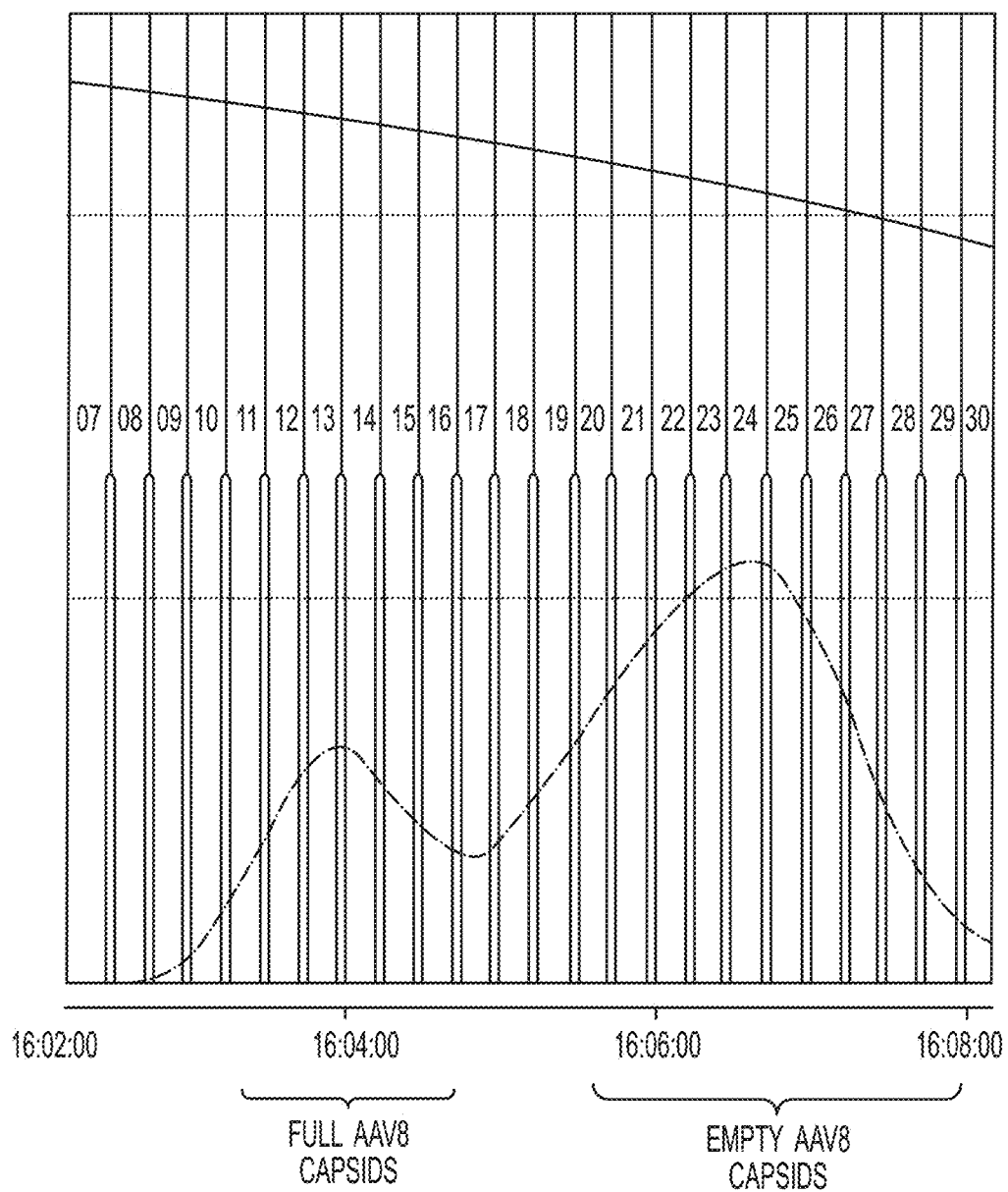
FIG. 12 is a curve showing ultracentrifugation of separated full and empty AAV8 particles using the 50-55-60% protocol in aqueous solution, including particles containing different DNA sequence variants. The VectorDNA was Human Coagulation Factor IX Padua, double stranded, Full length approx. 4.8 kB. Single fractions as indicated in the UC profile were processed on a 4 ml AEX-TMAE column and formulated to a final product. Each of the formulated fraction was analyzed. Fraction 10 to 14 were pooled and represents the homologous end product that contains AAV8 with full length vector DNA. Fraction 15 to 21 and additionally fraction 25 and 26 are processed separately and show decreasing length of the vector DNA encapsulated in the AAV8 particles. This is shown in the xDNA-Agarose gels of FIGS. 14 and 15 and in the data of the analytical ultracentrifugation (AUC) shown in FIG. 16.
Figure 13:
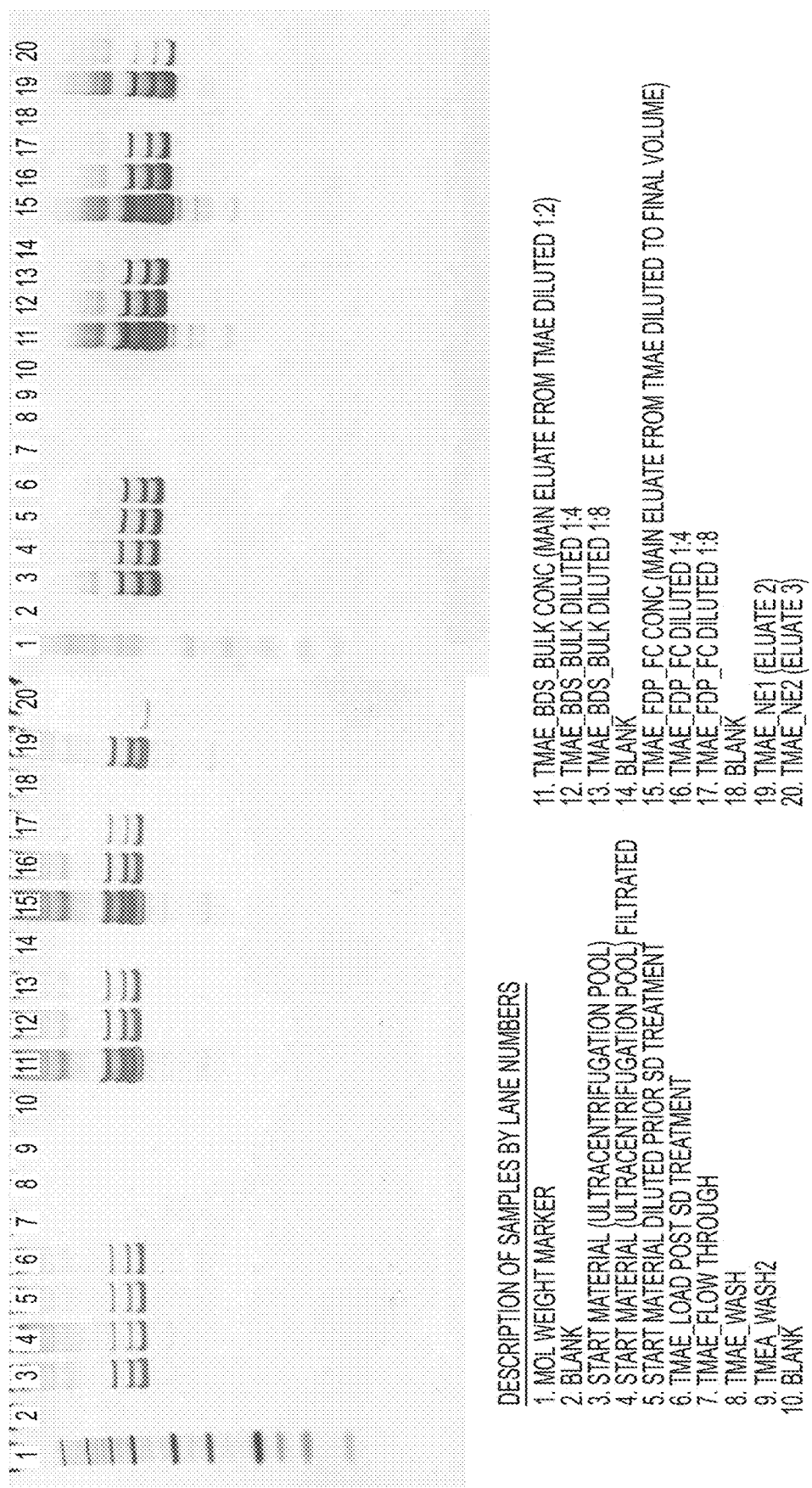
FIG. 13 is a silver stain (left) and western blot (right) of the fractions indicated.

The collection of fractions 25 mL each starts with fraction 7 and ends at the beginning of the waste peak. The first peak in FIG. 12 at a higher sucrose density represents the "Full capsids". The second peak represents the "mostly empty capsids".

Fractions F10 to F14 were pooled and further purified on Fractogel® EMD TMAE (M) as standard AAV8 "Full capsids" in the same way as the other AAV8 containing fractions. Table 15 provides details of the TMAE chromatography step and Table 16 details the buffers used.

TABLE 15

| | Step | Buffer | Amount | Flow rate |
|---|---|---|---|---|
| 1 | Equilibration 1 | TWA (2M NaCl) | 5 | 100 |
| 2 | Equilibration 2 | T50EQ | 10 | 100 |
| | | | 100-300 mL | 100 |
| 3 | Product load | diluted SD treated UC pool | Cond: 2.5-4.5 mS/cm pH 8.3-8.7 No filtration | |
| 4 | Wash 1 | | 20 | 100 |
| 5 | Wash 2 | | 10 | 60 |
| 6 | Elution | Gradient 0-100% Chat_EL in Chat_A Pool collecting | 12 Start: UV280 >0.02 AU, End at 17% of peak max (UV280) decreasing | 60 |
| 7 | Regeneration | | x | |

TABLE 16

| Buffer | Buffer content | pH | Conductivity |
|---|---|---|---|
| Equilibration 1 | 2 mol NaCl | n.d | 140-172 mS/cm/25° C. |
| Equilibration 2 and Wash 1 | 50 mM TrisHCl | 8.5 ± 0.2 | 1-2 mS/cm/25° C. |
| Wash 2 | 8.09 mM Na2HPO4, 1.47 mM KH2PO4, 2.68 mM KCl, 5% Sorbitol | 7.4 ± 0.2 | 1-2 mS/cm/25° C. |
| Elution | 8.09 mM Na2HPO4, 1.47 mM KH2PO4, 2.68 mM KCl, 5% sorbitol + 600 mM NaCl | 7.4 ± 0.2 | 51-55 mS/cm/25° C. |

Approximately 25 ml of a single ultracentrifugation fraction was applied separately to a 4 ml TMAE Column by dilution of 1:2.5 with the equilibration buffer 50 mM Tris, pH 8.5±0.2. After the solvent detergent treatment in the presence of 0.3% Tri-n-butylphosphate, 1% Triton X-100 and 0.3% Polysorbate 80 the conductivity was adjusted to 3.6±0.2 mS/cm with a further 1:2 dilution and the AAV8 containing solution was applied to a chromatography column containing Fractogel® EMD TMAE (M) (Merck-Millipore, cat. no. 116881) ID 10 mm, bed height 50 mm±5 mm (Merck-Millipore Vantage VL 10×250 or similar) followed by a first wash step with equilibration buffer 50 mM Tris, pH 8.5±0.2 and a second wash step with 8.09 mM $Na_2HPO_4$, 1.47 mM $KH_2PO_4$, 2.68 mM KCl, 5% sorbitol, pH 7.4. The elution is conducted by a gradient of 12 column volumes from 8.09 mM $Na_2HPO_4$, 1.47 mM $KH_2PO_4$, 2.68 mM KCl, 5% sorbitol, pH 7.4 to 8.09 mM $Na_2HPO_4$, 1.47 mM $KH_2PO_4$, 2.68 mM KCl, 5% sorbitol+600 mM NaCl, pH 7.4. The main amount of the AAV8 elutes as a distinct sharp peak and was collected as E2 (Eluate2) which represents the purified AAV8 product. The obtained AAV8 containing eluate E2 (Eluate2) was diluted 1:2 with 8.09 mM $Na_2HPO_4$, 1.47 mM $KH_2PO_4$, 2.68 mM KCl, 5% sorbitol+600 mM NaCl pH 7.4 to adjust to the matrix of the formulation buffer (8.09 mM $Na_2HPO_4$, 1.47 mM $KH_2PO_4$, 2.68 mM KCl, 5% sorbitol+350 mM NaCl, pH 7.4). The column was finally stripped with 2 M sodium chloride followed by a regeneration procedure. The chromatography system was placed at an ambient temperature of +18° C. to +25° C.

Figure 14:
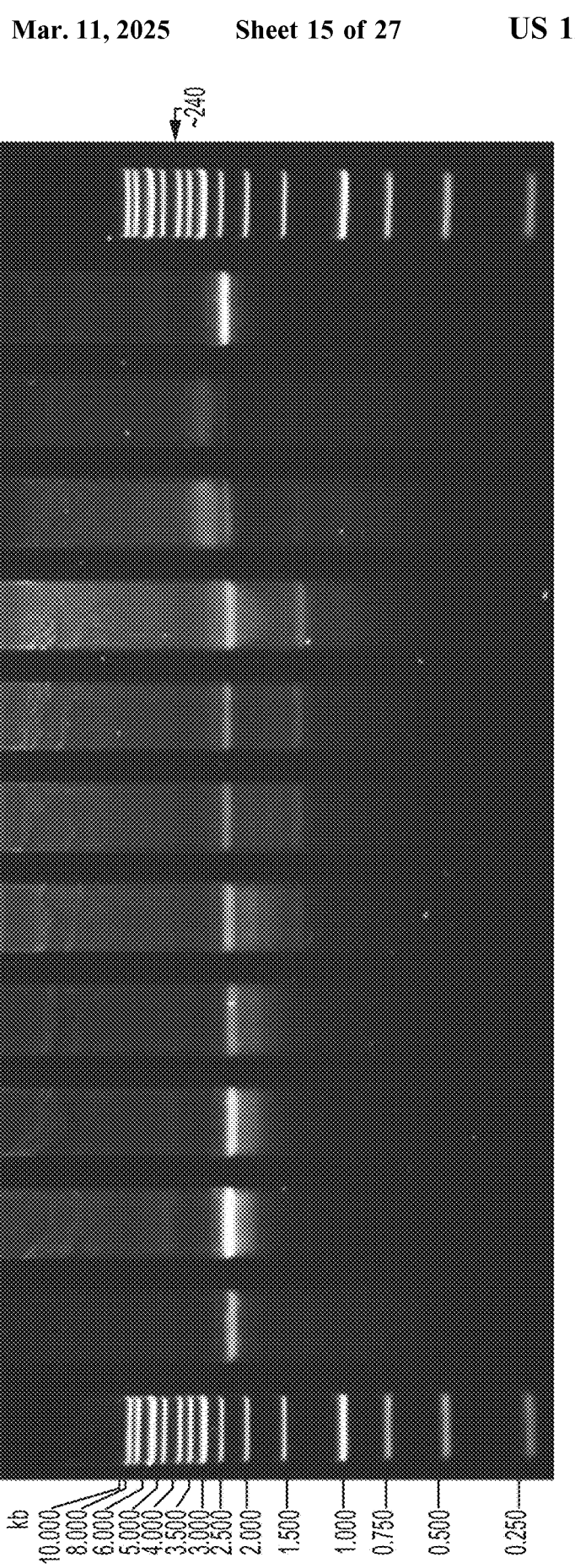
FIG. 14 is a photograph of a 1% agarose gel of the following samples taken from the ultracentrifugation of AAV8 particles described in Example 9: Lane 1=Marker; Lane 2=PV007 (AAV8 derived from the original Chatham process); Lane 3=Fraction 15; Lane 4=Fraction 16; Lane 5=Fraction 17; Lane 6=Fraction 18; Lane 7=Fraction 19; Lane 8=Fraction 20; Lane 9=Fraction 21; Lane 10=Fraction 25; Lane 11=Fraction 26; Lane 12=product AAV8 for clinical administration; and Lane 13=Marker. BDS=bulk drug substance (final diluted TMAE-Eluate). This figure shows that pooled fractions 10 to 14 of the UV peak obtained at higher sucrose density in the ultracentrifugation contain a highly pure single DNA band without any further hint to smaller DNA variants of the vector DNA.
Figure 15:
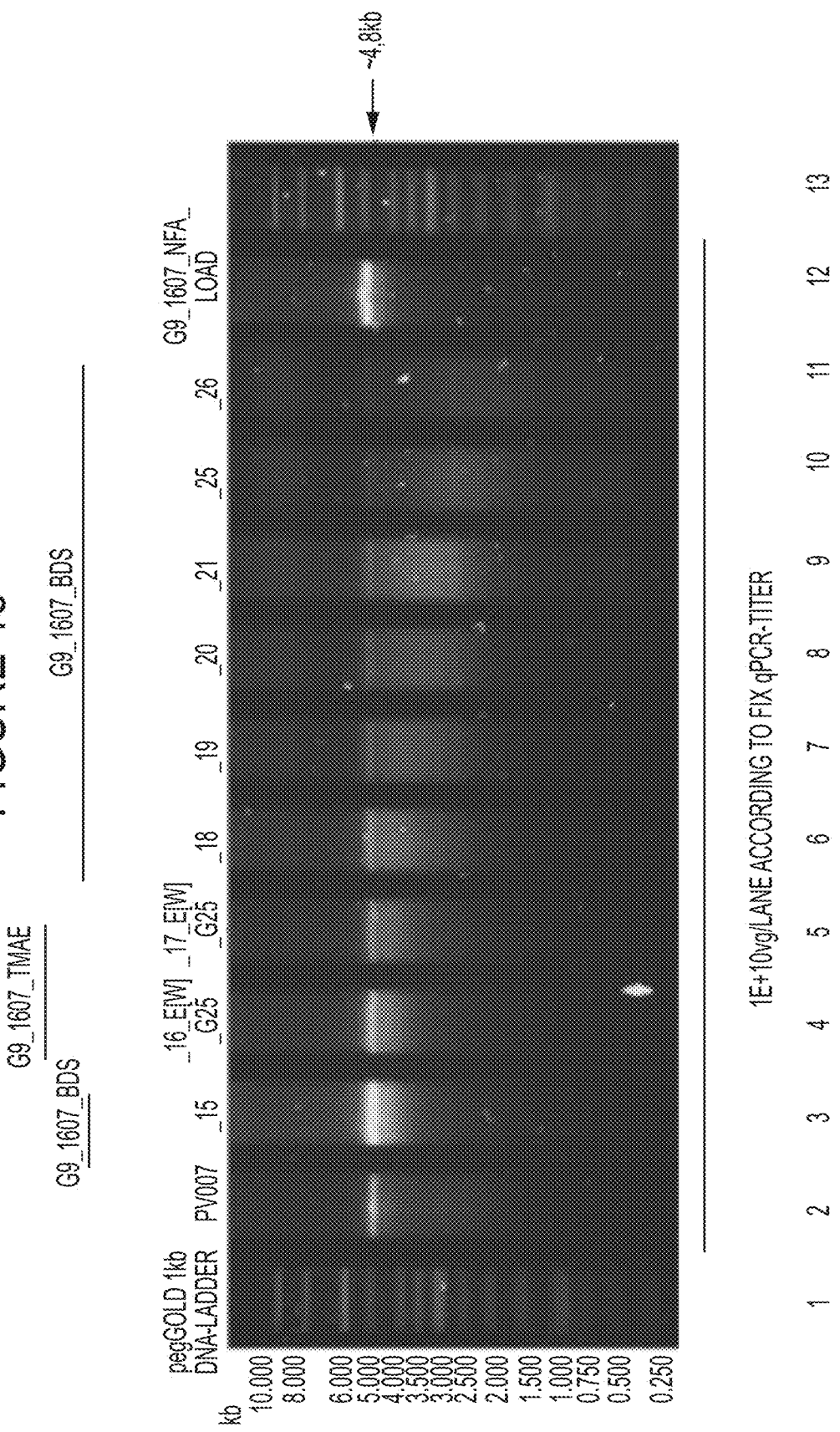
FIG. 15 is a photograph of a 0.8% alkaline agarose gel of the following samples taken from the ultracentrifugation of AAV8 particles described in Example 9: Lane 1=Marker; Lane 2=PV007 (AAV8 derived from previous production processes); Lane 3=Fraction 15; Lane 4=Fraction 16; Lane 5=Fraction 17; Lane 6=Fraction 18; Lane 7=Fraction 19; Lane 8=Fraction 20; Lane 9=Fraction 21; Lane 10=Fraction 25; Lane 11=Fraction 26; Lane 12=product AAV8 for clinical administration; and Lane 13=Marker. BDS=bulk drug substance (final diluted TMAE-Eluate). This figure shows that pooled fractions 10 to 14 of the UV peak obtained at higher sucrose density in the ultracentrifugation contain a highly pure single DNA band without any further hint to smaller DNA variants of the vector DNA.

Fractions 10 to 21 were analyzed with analytical ultracentrifugation (AUC) and DNA-Analysis of AAV8-vectors (Containing Factor IX Padua double stranded (4.8 kb)) was performed by native agarose gel electrophoresis and alkaline agarose gel electrophoresis. FIGS. 13-16 show analytical data of single fractions obtained by UC after polishing on TMAE. FIG. 14 is a photo of an Agarose 1% native and FIG. 15 is a photo of an Agarose 0.8% alkaline. As shown in FIG. 15, the pooled fractions ×10 to ×14 of the UV peak obtained at higher sucrose density in the ultracentrifugation contained a highly pure single DNA band without any further hint to smaller DNA variants of the vector DNA.

Data of analytic UC is provided in Table 17.

TABLE 17

| Fraction Number | empty (50S) | partially filled | filled (80S) |
|---|---|---|---|
| F10-14 | 4% | 0% | 96% |
| F15 | 6% | 1% | 93% |
| F16 | 16% | 0% | 85% |
| F17 | 21% | 0% | 79% |
| F18 | 29% | 23% | 48% |
| F19 | 41% | 35% | 24% |
| F20 | 52% | 43% | 5% |
| F21 | 60% | 38% | 3% |
| F25 | 82% | 17% | 1% |
| F26 | 81% | 18% | 2% |

Fraction Nos. 22, 23 and 24 not analyzed

As shown in Table 17, Fractions 10-15 contained the highest amounts of filled AAV capsids. While substantial amounts of full capsids are found in Fractions 16 and 17, the amounts were slightly less and the amount of empty capsids rises, relative to Fractions 10-15. A further decrease in the amount of full capsids and further increase in empty capsids were observed in Fractions 19 and 20.

FIG. 16 shows data for single BDS from indicated UC fractions. These results show a homogenous AAV8 product from UC fraction 10 to 15 with no detection of incomplete vector DNA content in AUC and agarose gel electrophoresis. Incomplete vector DNA appears from fraction 17 and was detected in later fractions of the "mostly empty capsids" zone. The detection of incomplete vectors was surprising because one would not expect to have such a wide range of resolution. Thus, the developed separation method is not limited to resolving capsids that are completely empty (i.e. no DNA) from those comprising "full", but it surprisingly also allows the separation of vector DNA of varying lengths that cannot be resolved from one another. It is also an indication that there is a meaningful separation of "full capsids" from "empty capsids" regardless of the length of the DNA in the "empty capsid" population. In other words, this method allows a depletion of empty vectors (including truncated and incomplete DNA) to obtain AAV with a high content of full AAV capsids.

Example 10

This method describes an exemplary method of nanofiltration for removal of viruses larger than AAV and larger than the pore size of the nanofilter applied.

An Asahi PLANOVA 35 nm filter, which contains bundles of micro-porous hollow-fibers constructed of natural hydrophilic cuprammonium regenerated cellulose with a narrow pore size range of 35 nm+/−2 nm, is tested with an integrity leakage test to confirm that the filter is free from pinholes or large defects and pre-washed with formulation buffer. Then anion exchange eluate is taken and filtered under constant pressure not exceeding 0.1 MPa in a dead-end mode through the nanofilter. Alternatively the filter could be run also in tangential flow method. Anion exchange eluate may be pre-diluted with elution buffer (PBS+600 mM NaCl) to adjust concentration of the virus particles. In order to recover all virus particles the nanofilter is post-washed with buffer (e.g. formulation buffer). Post-integrity testing of the nanofilter is performed with the leakage test and a gold particle test to prove that the nanofilter pore size distribution has not changed and the nanofilter remained its integrity during filtration. Higher sample load results in higher yield. Therefore, typically more than 50 L of solution per m² filter area is applied.

Example 11

This method describes an exemplary method of nanofiltration for removal of viruses larger than AAV and larger than the pore size of the nanofilter applied.

An Asahi PLANOVA 35 nm filter, which contains bundles of micro-porous hollow-fibers constructed of natural hydrophilic cuprammonium regenerated cellulose with a narrow pore size range of 35 nm+/−2 nm, was tested with an integrity leakage test to confirm that the filter is free from pinholes or large defects and pre-washed with formulation buffer. Then, 4.05 ml of the pooled fractions comprising 2870.98 μg/ml AAV-8 (concentration determined by ELISA) was first diluted in 4.05 of a buffer of 1.47 mM $KH_2PO_4$, 2.68 mM KCl, 8.09 mM $Na_2HPO_4$, 600 mM NaCl and 5% Sorbitol, at pH 7.4. The dilution factor was 1:2. Then, 8.10 grams of the first dilution was diluted in 61.57 grams of a buffer of 1.47 mM $KH_2PO_4$, 2.68 mM KCl, 8.09 mM $Na_2HPO_4$, 350 mM NaCl and 5% Sorbitol, at pH 7.4 to yield a load buffer. The dilution factor of the load buffer was 1:8.6 as compared to the first dilution, and 1:17.2 as compared to the pooled fractions.

The nanofilter was conditioned with 25 ml of a buffer comprising 1.47 mM $KH_2PO_4$, 2.68 mM KCl, 8.09 mM $Na_2HPO_4$, 350 mM NaCl and 5% Sorbitol, at pH 7.4. During the conditioning, 10 ml of the buffer was used to purge the filter without pressure applied and with the retentate outlet open. Then, about 15 ml of the buffer was filtrated through the hollow fibers, with 0.9 bar of constant pressure applied and the retentate outlet closed.

Then, 9 ml of a flushing buffer was applied to the reservoir tank under 0.9 bar of constant pressure. The flushing buffer comprised 1.47 mM $KH_2PO_4$, 2.68 mM KCl, 8.09 mM $Na_2HPO_4$, 350 mM NaCl and 5% Sorbitol, at pH 7.4. Samples were then taken after flushing. After samples were taken, 60 grams of the above load buffer was then filtered under constant pressure of 0.9 bar in a dead-end mode through the nanofilter.

Data from the filtration is presented in Table 18 below. The yield of AAV from filtration is at least 77%.

TABLE 18

| Sample code: | Volume [g] or [ml] | AAV ELISA Gatternig Total (μg) | AAV ELISA Gatternig Yield (%) | AAV ELISA Weber (particles/ml) | AAV ELISA Weber (particles) | AAV ELISA Weber Yield (%) | Load AAV [mg] bzw. [g/m²] |
|---|---|---|---|---|---|---|---|
| AV_meC_NFA_04A_POOL | 4.05 | 10955.747 | — | 9.19E+14 | 3.72E+15 | — | — |
| AV_meC_NFA_04A_LOAD | 60.00 | 10111.686 | 100.00 | 5.35E+13 | 3.21E+15 | 100.00 | 10.112 |
| AV_meC_NFA_04A_NF | 60.25 | 7659.631 | 75.75 | 4.13E+13 | 2.49E+15 | 77.52 | — |
| AV_meC_NFA_04A_FLUSH | 9.34 | 601.920 | 5.95 | 2.09E+11 | 1.95E+12 | 0.06 | — |
| AV_meC_NFA_04A_BULK | 66.63 | 8392.144 | 82.995 | 3.73E+13 | 2.49E+15 | 77.424 | — |

Example 12

The following example describes an exemplary method of testing biopotency of an AAV8 product.

In the in-vitro biopotency assay, the viral vector AAV8-FIX transfect a hepatic target cell line, which subsequently secretes functional, measurable FIX protein into the medium.

In a first step HepG2 target cells are transduced by AAV8-FIX. During incubation time FIX is released into cell supernatant. In a second step, the factor IX-activity of the cell culture supernatant is directly measured by a FIX chromogenic assay. The measurement of an AAV8-FIX sample is given as percentage relative to a reference material. The method allows a quantitative assessment of the biologic function of the AAV8-FIX gene therapy vector.

Example 13

This example demonstrates an AAV-specific ELISA.

In the foregoing examples, an AAV-specific ELISA was carried out after steps of the process of the present disclosure to identify AAV-containing fractions and to calculate the DNA/AAV ratio or "Specific activity" of the AAV which is represented by the ratio of qPCR to μg AAV8. The DNA/AAV ratio reflects the vector DNA encapsulated in the AAV particles.

AAV8 ELISA was carried out with an AAV-8 titration ELISA Kit (Art. No. PRAAV8; Progen (Heidelberg, Germany) on a TECAN Roboter system. Briefly, a monoclonal antibody specific for a conformational epitope on assembled AAV8 capsids (ADK8) was coated onto microtiter strips and was used to capture AAV8 particles from the AAV fraction. The capture AAV8 particles were detected by two steps. In a first step, a biotin-conjugated monoclonal antibody specific for the ADK8 antibody was bound to the immune complex (of ADK8 and ADK8 antibody). Streptavidin peroxidase conjugates were added to the immune complexes bound to the biotin-conjugated monoclonal antibody and the streptavidin peroxidase conjugates reacted with the biotin. A peroxidase substrate solution was added and a color reaction which is proportional to the amount of bound AAV particles occurs. The color reaction is measured photometrically at 450 nm.

The ELISA determines the amount of AAV8 particles present in the tested fraction.

Example 14

This example demonstrates an exemplary method of separating empty from full AAV particles through ultracentrifugation using a 50% ethylene glycol buffered loading solution and 50% sucrose gradient (i.e., 1:1 ratio). Product related impurities like "empty capsids" and host cell proteins such as HSP70 and LDH, are eliminated via this step.

The buffered ethylene glycol solution (50% (w/w) in TrisHCl/NaCl) comprising AAV8, with human coagulation Factor VIII (full length ~4.8 kb), was loaded into the ultracentrifuge (UC) followed by a sucrose gradient formed of two different sucrose solutions which vary in sucrose concentration. The ratio of loaded sample to sucrose gradient is 1:1. The sucrose solution loaded into the UC first had a 55% sucrose concentration. The sucrose solution loaded into the UC immediately after the first sucrose solution had a 60% sucrose concentration.

One kilogram of the buffered sucrose solution with a 55% sucrose concentration was prepared by mixing 2.42 g of Tris(hydroxymethyl)aminomethane (Trometamol) with 8.00 g sodium chloride and 550.00 g sucrose. WFI was added to near 1 kg, with 1 M NaOH and 25% HCl used to adjust the pH as needed. WFI was then added to 1 kg.

One kilogram of the buffered sucrose solution with a 60% sucrose concentration was prepared by mixing 2.42 g of Tris(hydroxymethyl)aminomethane (Trometamol) with 8.00 g sodium chloride and 600.00 g sucrose. WFI was added to near 1 kg, with 1 M NaOH and 25% HCl used to adjust the pH as needed. WFI was then added to 1 kg.

In this example, a 3,200 ml core was used, wherein the 50% ethylene glycol buffered solution containing AAV8 was 1,600 ml, the 55% (w/w) sucrose solution was 800 ml, and the 60% (w/w) sucrose solution was 800 ml.

A density gradient forms during a first UC phase wherein rotational speed was set at 4000 rpm and the temperature was maintained at 2-10° C. After the first phase, the rotational speed was increased to 35000 rpm and the temperature was increased to 22° C. During this second phase at higher speed and temperature, full AAV particles were separated from the empty capsids. After 20 hours, the ultracentrifuge was stopped and the fractions containing the majority of full AAV particles were collected.

Figure 19:
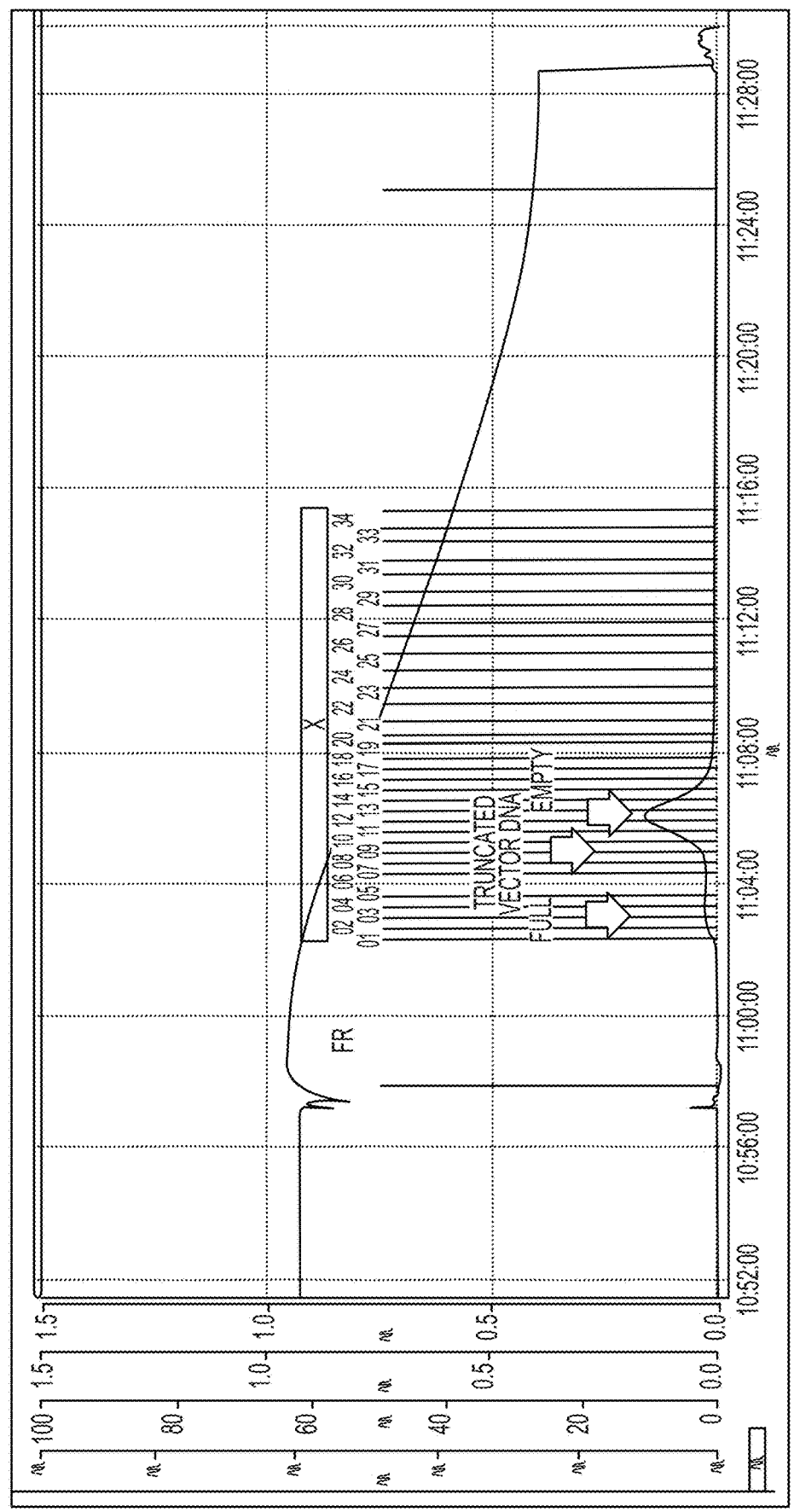
FIG. 19 is a graph of the ultracentrifugation elution profile in which AAV8 in a 50% (w/w) ethylene glycol in Tris/NaCl buffer is ultracentrifuged for 20 hours at 35000 rpm in through a sucrose gradient with 55% and 60% sucrose solutions. The ratio of AAV8 loading sample to the sucrose gradient is 1:1, with a core volume of 3,200 ml. The vector DNA is human coagulation Factor VIII, full length (~4.8 kB).

The results are shown in FIG. 19, in which full capsids (fractions 1-6) are resolved from the empty capsids (fractions 8-17).

Figure 20:
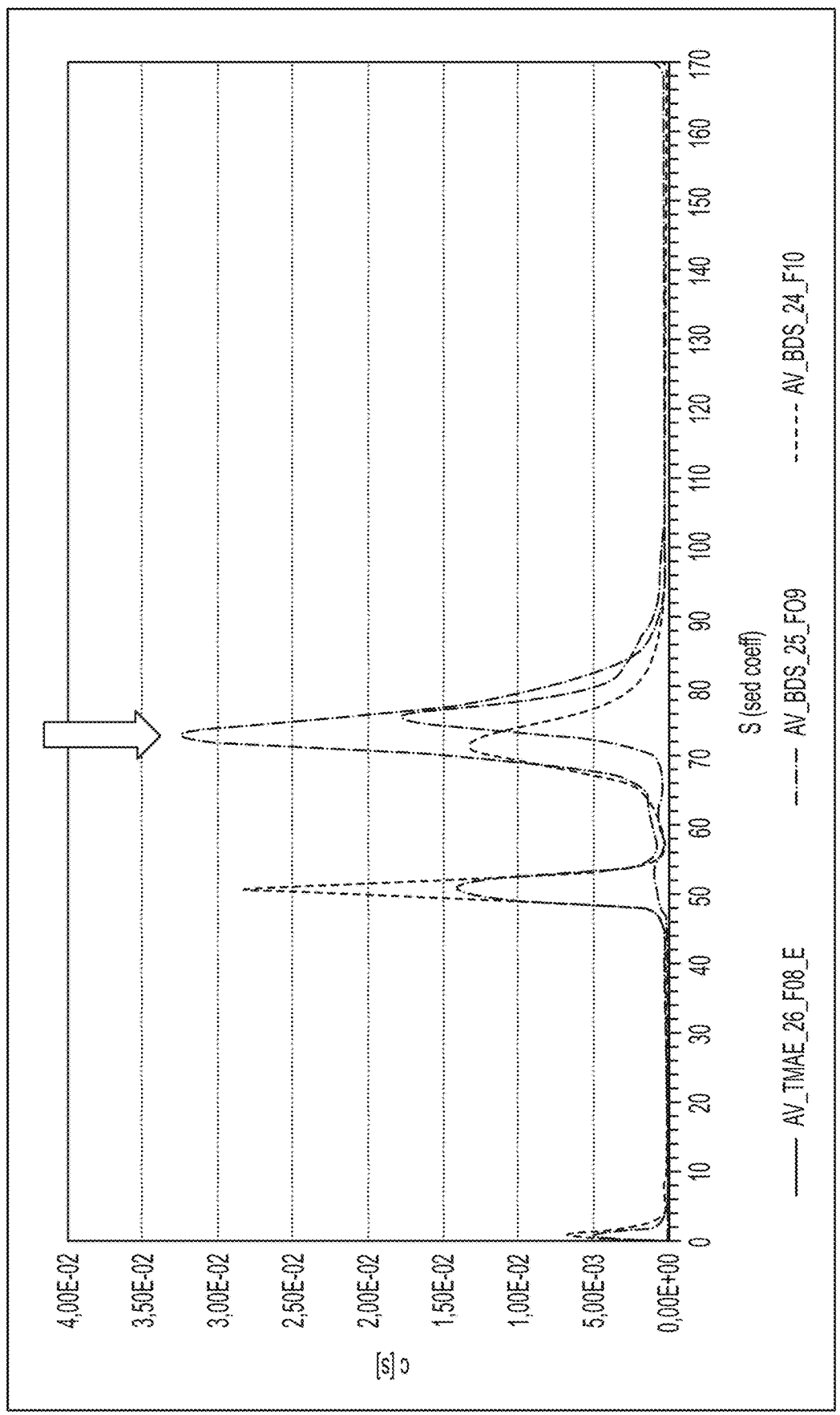
FIG. 20 is an overlay of sedimentation coefficient graphs from Fractions 8-10 (see FIG. 19) demonstrating subspecies separation. The arrow denotes a shift towards AAV8 with lower weight from fractions with higher density to lower density in the UC-gradient. Fraction 8>Fraction 9>Fraction 10.

FIG. 20 is an overlay of sedimentation coefficient graphs from Fractions 8-10 demonstrating subspecies (i.e., incomplete vector DNA) separation. The arrow denotes a shift towards AAV8 with lower weight from fractions with higher density to lower density in the UC-gradient (i.e., density: Fraction 8>Fraction 9>Fraction 10). This is further demonstration that vector DNA can be separated based on size with appropriate resolution with this protocol. See also, Table 19.

Example 15

Figure 21:
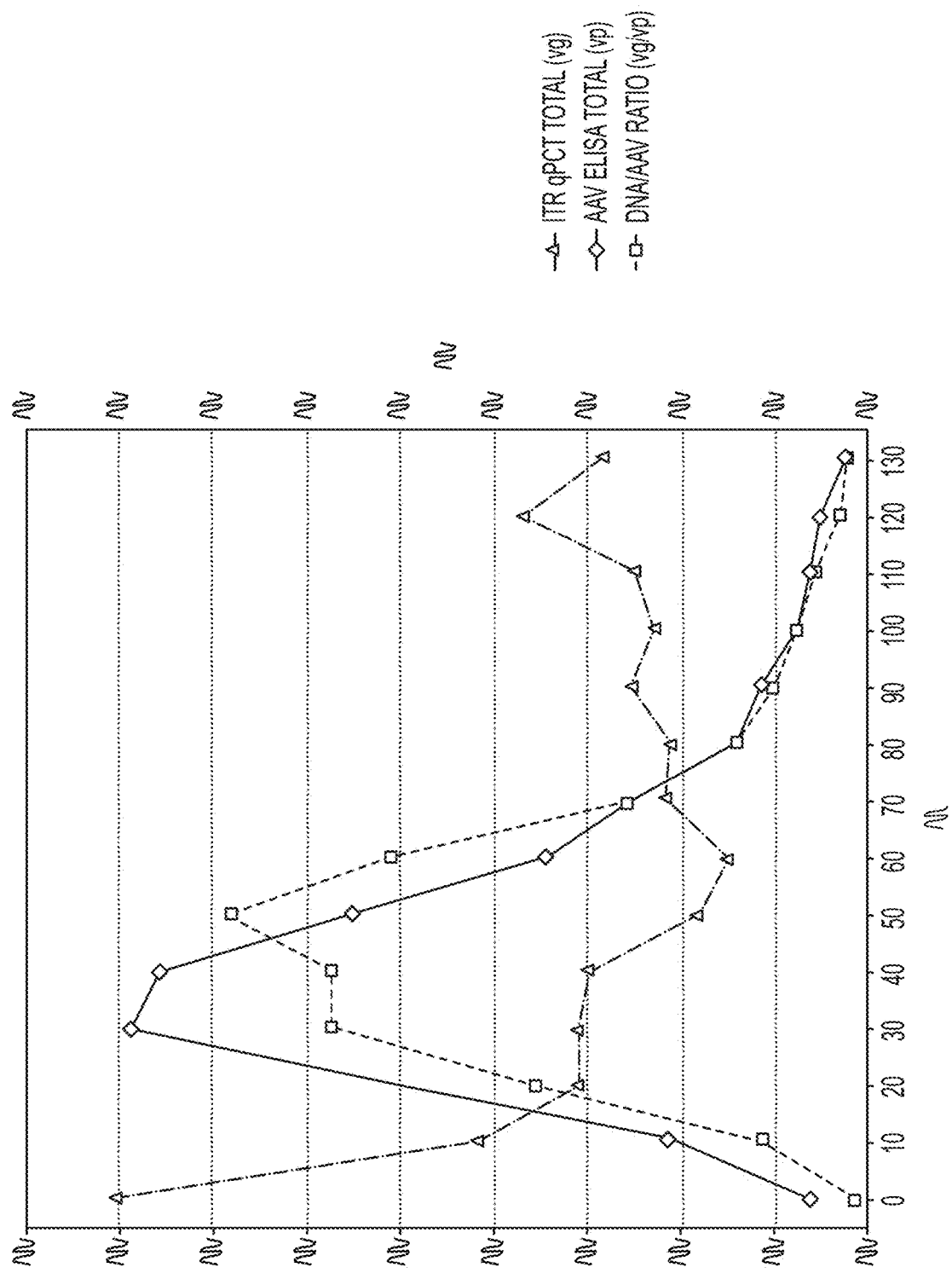
FIG. 21 is a graph of a separation of AAV8 containing single stranded vector DNA of human coagulation Factor IX Padua (2.6 kB) using ultracentrifugation with the 50-55-60% sugar layer protocol, where the AAV8 sample is loaded in a TrisHCl/NaCl buffered solution. Each Fraction is tested via: AAV8 ITR qPCR and ELISA. DNA/AAV ratio is a ratio of ITR qPCR vector genomes (vg/ml)/AAV8 capsid antigen ELISA (cp/ml). The data was normalized to allow the graphs to be presented on the same axes.

This example demonstrates ultracentrifugation using a sucrose gradient, using the 50-55-60 sucrose solution method. The method is the same as indicated in Example 7, except the AAV8 particles contained single stranded vector DNA of human coagulation Factor IX Padua (2.6 kB). As indicated in FIG. 21, the separation between full versus empty capsids is not as resolved as indicated by the overlap of the ITR pPCR and AAV ELISA.

Example 16

Figure 22:
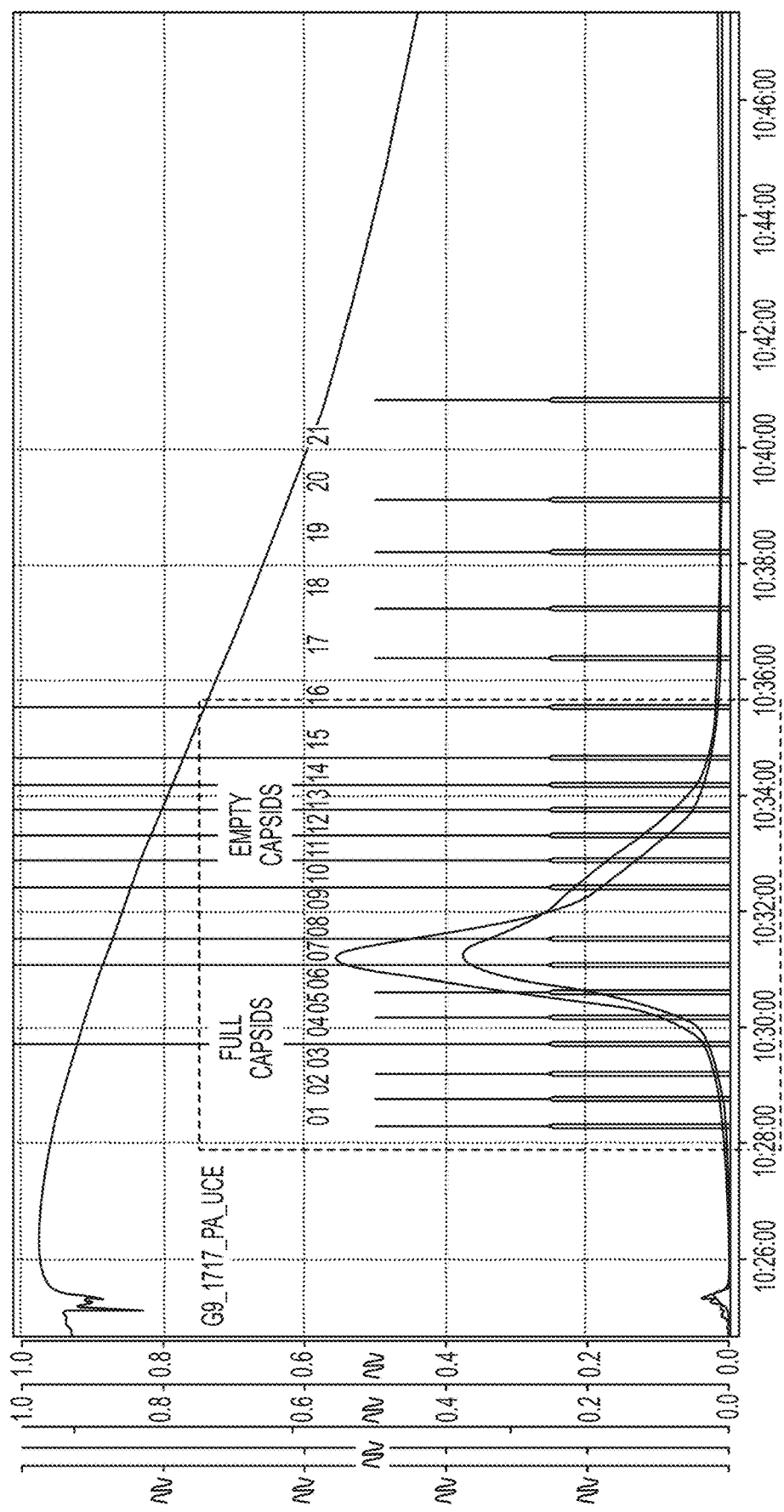
FIG. 22 is a graph of the ultracentrifugation elution profile in which AAV8 in a 50% (w/w) ethylene glycol in Tris/NaCl buffer is ultracentrifuged for 20 hours at 35000 rpm in through a sucrose gradient with 55% and 60% sucrose solutions. The ratio of AAV8 loading sample to the sucrose gradient is 1:1, with a core volume of 7,700 ml. The vector DNA is human coagulation Factor IX Padua, single stranded self-complementary, full length (~2.6 kB).

This example demonstrates ultracentrifugation using a sucrose gradient, using the 55-60 sucrose solution method as described in Example 6, except using a total of 7,700 ml core volume. Thus, the load volume was 6,100 ml in 50% ethylene glycol TrisHCl buffered solution, the 55% sucrose solution volume was 800 ml, and the 60% sucrose solution was also 800 ml. The ultracentrifugation elution profile is depicted in FIG. 22. Here there are no "waste peaks" because the AAV is highly purified. Full AAV8 is collected from Fractions 1-8 (50 ml each). The "empty" AAV is collected from Fractions 9-15 (50 ml each). Further fractions, 15-21 are also collected (100 ml each). The first peak in FIG. 22 at a higher sucrose density represents the "Full capsids". The second peak represents the "empty capsids".

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification

TABLE 19

|  | WAX [%] full | WAX [%] empty | AUC Area empty [%] (50S) | AUC Area [%] intermediate1 (60S) | AUC Area [%] Full (70-80S) |
|---|---|---|---|---|---|
| Pool Fraction 01 to 06 | 95 | 5 | 5.6 | 4.3 | 79.2 |
| Fraction 08 | 80 | 20 | 1.5 | 7.4 | 87.5 |
| Fraction 09 | 65 | 35 | 16.7 | 2.2 | 81.1 |
| Fraction 10 | 40 | 60 | 57.6 | 1.8 | 40.6 | should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method of producing an adeno-associated virus (AAV) product comprising:
   (i) transfecting host cells with a plasmid comprising a gene of interest to be packaged into AAV,
   (ii) culturing the transfected host cells in a cell culture,
   (iii) collecting a supernatant of the cell culture, wherein the supernatant comprises AAV particles,
   (iv) loading into a zonal rotor a) the supernatant and b) at least two sugar solutions, each of which has a different sugar concentration and each of which comprises a sugar at a concentration equivalent to a sucrose concentration ranging from about 45% (w/w) to about 65% (w/w) sucrose,
   (v) operating an ultracentrifuge comprising the zonal rotor in batch mode to separate full AAV capsids from empty AAV capsids, whereupon a sugar gradient is formed, and
   (vi) obtaining an AAV fraction wherein at least or about 60% of AAV particles in the AAV fraction are full AAV capsids.

2. The method of claim 1, wherein each sugar solution comprises a sugar at a concentration equivalent to a sucrose concentration ranging from about 50% (w/w) to about 60% (w/w) sucrose.

3. The method of claim 1, wherein each sugar solution comprises a sugar at a concentration equivalent to a sucrose concentration ranging from about 55% (w/w) to about 60% (w/w) sucrose.

4. The method of claim 1, wherein at least one of the sugar solutions comprises:
   (a) sugar at a concentration equivalent to a sucrose concentration greater than about 50% (w/w) sucrose;
   (b) sugar at a concentration equivalent to a sucrose concentration greater than about 55% (w/w) sucrose;
   (c) sugar at a concentration equivalent to a sucrose concentration ranging from about 60% (w/w) to about 65% (w/w) sucrose; or
   (d) any one of (a)-(c).

5. The method of claim 1, wherein one sugar solution comprises a sugar at a concentration equivalent to a sucrose concentration ranging from about 52% (w/w) to about 58% (w/w) sucrose, wherein a second sugar solution comprises a sugar at a concentration equivalent to a sucrose concentration ranging from about 57% (w/w) to about 63% (w/w) sucrose, and optionally wherein a third sugar solution comprises a sugar at a concentration equivalent to a sucrose concentration ranging from about 47% (w/w) to about 53% (w/w) sucrose.

6. The method of claim 1, wherein two sugar solutions are loaded into the zonal rotor.

7. The method of claim 6, wherein two sugar solutions are loaded into the zonal rotor and wherein one sugar solution comprises a sugar at a concentration equivalent to a sucrose concentration ranging from about 52% (w/w) to about 58% (w/w) sucrose and a second sugar solution comprises a sugar at a concentration equivalent to a sucrose concentration ranging from about 57% (w/w) to about 63% (w/w) sucrose.

8. The method of claim 1, wherein at least three sugar solutions are loaded into the zonal rotor.

9. The method of claim 8, wherein three sugar solutions are loaded into the zonal rotor.

10. The method of claim 8, wherein three sugar solutions are loaded into the zonal rotor and wherein one sugar solution comprises a sugar at a concentration equivalent to a sucrose concentration ranging from about 47% (w/w) to about 53% (w/w) sucrose, a second sugar solution comprises a sugar at a concentration equivalent to a sucrose concentration ranging from about 52% (w/w) to about 58% (w/w) sucrose, and a third sugar solution comprises a sugar at a concentration equivalent to a sucrose concentration ranging from about 57% (w/w) to about 63% (w/w) sucrose.

11. The method of claim 1, wherein in step (i), the supernatant is loaded before a sugar solution comprising a sugar at a concentration equivalent to a sucrose concentration ranging from about 52% (w/w) to about 58% (w/w) sucrose, and wherein the sugar solution comprising a sugar at a concentration equivalent to a sucrose concentration ranging from about 52% (w/w) to about 58% (w/w) sucrose is loaded before a sugar solution comprising a sugar at a concentration equivalent to a sucrose concentration ranging from about 57% (w/w) to about 63% (w/w) sucrose.

12. The method of claim 1, wherein in step (i), the supernatant is loaded before a sugar solution comprising a sugar at a concentration equivalent to a sucrose concentration ranging from about 47% (w/w) to about 53% (w/w) sucrose, wherein the sugar solution comprising a sugar at a concentration equivalent to a sucrose concentration ranging from about 47% (w/w) to about 53% (w/w) sucrose is loaded before a sugar solution comprising a sugar at a concentration equivalent to a sucrose concentration ranging from about 52% (w/w) to about 58% (w/w) sucrose, and wherein the sugar solution comprising a sugar at a concentration equivalent to a sucrose concentration ranging from about 52% (w/w) to about 58% (w/w) sucrose is loaded before a sugar solution comprising a sugar at a concentration equivalent to a sucrose concentration ranging from about 57% (w/w) to about 63% (w/w) sucrose.

13. The method of claim 1, wherein each sugar solution is loaded in the zonal rotor at equal volumes.

14. The method of claim 1, wherein the sugar solution with the smallest sugar concentration is loaded in the zonal rotor at a volume which is twice the volume of at least one of the other sugar solutions in the zonal rotor.

15. The method of claim 1, wherein the sugar solution with the smallest sugar concentration is loaded in the zonal rotor at a volume which is at least the volume of all other sugar solutions combined in the zonal rotor.

16. The method of claim 1, wherein three sugar solutions are loaded into the zonal rotor, wherein the sugar solution with the smallest sugar concentration is loaded in the zonal rotor at a volume which is at least twice the volume of the sugar solution with the largest sugar concentration, optionally, wherein the volume of the sugar solution with the largest sugar concentration is equal to the volume of the sugar solution with the intermediate sugar concentration.

17. The method of claim 1, wherein at least two sugar solutions are loaded into the zonal rotor, wherein the sugar solution with the smallest sugar concentration is loaded in the zonal rotor at a volume which is at least twice the volume of at least one other sugar solution in the zonal rotor.

18. The method of claim 1, wherein at least two sugar solutions are loaded into the zonal rotor, wherein the sugar solution with the smallest sugar concentration is loaded in the zonal rotor at a volume which is the same volume of at least one other sugar solution in the zonal rotor.

19. The method of claim 1, wherein the ratio of the volume of the sugar gradient to the volume of the supernatant loaded in the zonal rotor is from about 1:1 to about 1:5.

20. The method of claim 1, wherein the supernatant loaded in the zonal rotor comprises an AAV buffered solution.

21. The method of claim 20, wherein each of the sugar solutions and/or the AAV buffered solution comprises TrisHCl at a concentration of about 10 mM to about 100 mM and NaCl at a concentration of about 100 mM to about 1M.

22. The method of claim 21, wherein the TrisHCl is at a concentration of 20 mM to 50 mM and wherein the NaCl is at a concentration of 150 mM to 750 mM.

23. The method of claim 21, wherein the TrisHCl is at a concentration of 20 mM to 50 mM and wherein the NaCl is at a concentration of 150 mM to 500 mM.

24. The method of claim 20, wherein each of the sugar solutions and/or the AAV buffered solution has a pH of about 7.0 to about 9.0 or about 7.4 to about 8.5.

25. The method of claim 24, wherein the AAV buffered solution has a pH of about 7.4.

26. The method of claim 20, wherein each of the sugar solutions and/or the AAV buffered solution comprises 45-55% (w/w) ethylene glycol.

27. The method of claim 20, wherein each of the sugar solutions and/or AAV buffered solution comprises 40%, 41%, 42%, 43%, 44%, 45%, 46%, 47%, 48%, 49%, 50%, 51%, 52%, 53%, 54%, 55%, 56%, 57%, 58%, 59%, or 60% (w/w) ethylene glycol.

28. The method of claim 1, wherein each sugar solution comprises one or more disaccharides or trisaccharides.

29. The method of claim 28, wherein the one or more disaccharides comprise sucrose, maltose, lactose, and combinations thereof.

30. The method of claim 1, wherein each sugar solution comprises sucrose.

31. The method of claim 1, comprising operating the ultracentrifuge at a first rotational speed of less than 10,000 rpm for less than 60 minutes, and at a second rotational speed within the range of about 30,000 to about 40,000 rpm for at least 12 hours.

32. The method of claim 1, comprising operating the ultracentrifuge at a first rotational speed of less than 10,000 rpm for less than 60 minutes, and at a second rotational speed within the range of about 30,000 to about 40,000 rpm for at least 4 hours.

33. The method of claim 32, wherein the first rotational speed is about 3,000 rpm to about 6,000 rpm, optionally, about 4,000 rpm.

34. The method of claim 32, wherein the second rotational speed is:
(a) about 35,000 rpm and optionally is maintained for about 4 to about 6 hours or
(b) about 35,000 rpm and optionally is maintained for about 16 to about 20 hours.

35. The method of claim 33, wherein the first rotational speed is maintained for about 15 to about 25 minutes.

36. The method of claim 32, further comprising accelerating the ultracentrifuge from the first rotational speed to the second rotational speed, wherein the acceleration is maintained for a duration of about 5 minutes to about 60 minutes.

37. The method of claim 32, further comprising decelerating the ultracentrifuge from the second rotational speed to the first rotational speed, wherein the deceleration is maintained for a duration of about 5 minutes to about 90 minutes.

38. The method of claim 37, further comprising:
maintaining the ultracentrifuge at a temperature of 8° C. or less for a duration of at least 30 minutes; and
stopping the ultracentrifuge after 30 minutes.

39. The method of claim 32, wherein the ultracentrifuge is operated at the first rotational speed to maintain a temperature between about 2° C. and about 10° C.

40. The method of claim 32, wherein the ultracentrifuge is operated at the second rotational speed to maintain a temperature between about 20° C. and about 25° C.

41. The method of claim 1, wherein the supernatant loaded into the zonal rotor comprises at least $1 \times 10^{12}$ AAV capsids per mL.

42. The method of claim 1, wherein prior to step (iv) the method further comprises (a) applying the supernatant to an anion exchange (AEX) chromatography column under conditions that allow for the AAV to flow through the AEX chromatography column and (b) collecting flow-through comprising the AAV.

43. The method of claim 1, further comprising at least one of:
(a) inactivating lipid-enveloped viruses of the AAV fraction with a solvent and/or detergent;
(b) nanofiltering the AAV fraction to remove viruses greater than 35 nm;
(c) conducting a polish step comprising performing AEX chromatography with a column comprising tentacle gel; and
(d) the host cells are HEK293 cells.

44. The method of claim 1, wherein the AAV is AAV1, AAV2, AAV3, AAV4, AAV5, AAV6, AAV7, AAV8, AAV9, or AAV10.

45. The method of claim 1, wherein (A) the volume of the sugar solutions is greater than or equal to about 50% of the volume of the zonal rotor, (B) the volume of the sugar solutions and the supernatant loaded in the zonal rotor is less than or equal to the volume of the zonal rotor, (C) the ratio of the volume of the sugar solutions to the volume of the supernatant loaded in the zonal rotor is less than or equal to one, or (D) a combination thereof.

46. The method of claim 1, wherein the AAV is AAV8.

47. The method of claim 1, wherein the AAV is AAV9.

48. The method of claim 1, wherein in step (i), the host cells are transfected with one or more plasmids for AAV production.

49. The method of claim 1, wherein after step (ii) and prior to step (iii) the transfected host cells are disrupted.

50. The method of claim 1, wherein in step (iii), the supernatant is further processed.

51. The method of claim 50, wherein the supernatant is further processed in one or both of the steps of:
(a) concentrating the supernatant using an ultra/diafiltration system; and
(b) filtering the supernatant via depth filtration.

* * * * *